United States Patent
Goodall et al.

(10) Patent No.: US 10,695,570 B2
(45) Date of Patent: Jun. 30, 2020

(54) PROMPTING SYSTEM AND METHOD FOR ENHANCING LEARNING WITH NEURAL MODULATION

(71) Applicant: Elwha LLC, Bellevue, WA (US)

(72) Inventors: Eleanor V. Goodall, Seattle, WA (US); Roderick A. Hyde, Redmond, WA (US); Eric C. Leuthardt, St. Louis, MO (US); Stephen L. Malaska, Snoqualmie, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 280 days.

(21) Appl. No.: 15/381,252

(22) Filed: Dec. 16, 2016

(65) Prior Publication Data

US 2018/0169411 A1 Jun. 21, 2018

(51) Int. Cl.
| | |
|---|---|
| *A61N 1/36* | (2006.01) |
| *A61N 1/372* | (2006.01) |
| *A61N 1/04* | (2006.01) |
| *A61N 1/05* | (2006.01) |

(52) U.S. Cl.
CPC ....... *A61N 1/37247* (2013.01); *A61N 1/0456* (2013.01); *A61N 1/0541* (2013.01); *A61N 1/36025* (2013.01); *A61N 1/36036* (2017.08); *A61N 1/36092* (2013.01); *A61H 2205/027* (2013.01)

(58) Field of Classification Search
CPC ................. A61N 1/36014; A61N 1/36053
See application file for complete search history.

(56) References Cited

U.S. PATENT DOCUMENTS

| | | | |
|---|---|---|---|
| 5,324,316 A | 6/1994 | Schulman et al. |
| 5,515,848 A | 5/1996 | Corbett, III et al. |
| 6,104,956 A | 8/2000 | Naritoku et al. |
| 6,456,866 B1 | 9/2002 | Tyler et al. |
| 7,797,042 B2 | 9/2010 | Dietrich et al. |
| D628,990 S | 12/2010 | Pedersen |
| D630,621 S | 1/2011 | Pedersen |
| D634,306 S | 3/2011 | Pedersen |
| 8,170,658 B2 | 5/2012 | Dacey, Jr. et al. |
| 8,204,786 B2 | 6/2012 | LeBoeuf et al. |
| 8,506,469 B2 | 8/2013 | Dietrich et al. |
| 8,612,008 B2 | 12/2013 | Kirsch et al. |
| 8,630,436 B2 | 1/2014 | Berg |
| 8,849,407 B1 | 9/2014 | Danilov et al. |
| 8,976,995 B2 | 3/2015 | Berg |

(Continued)

OTHER PUBLICATIONS

U.S. Appl. No. 15/381,447, Goodall et al.
(Continued)

*Primary Examiner* — Michael J D Abreu

(57) ABSTRACT

Systems and related methods for enhancing learning of an activity by a subject are described. A prompt for causing the subject to perform the activity is delivered repeatedly, in combination with a neural stimulus, with timing of delivery of prompts and neural stimuli controlled by electrical control circuitry. Neural stimuli are delivered with a transcutaneous neural stimulator located fitted in or on at least a portion of an ear of the subject. The system is implemented in connection with a personal computing device such as a smart phone or tablet computer.

33 Claims, 41 Drawing Sheets

(56) References Cited

U.S. PATENT DOCUMENTS

| | | | |
|---|---|---|---|
| 9,025,800 | B2 | 5/2015 | Kidmose et al. |
| D744,456 | S | 12/2015 | Pedersen |
| 9,358,374 | B2 | 6/2016 | Dacey, Jr. et al. |
| 9,415,220 | B1 | 8/2016 | Spinelli et al. |
| 2003/0195588 | A1 | 10/2003 | Fischell et al. |
| 2005/0165460 | A1 | 7/2005 | Erfan |
| 2006/0094974 | A1 | 5/2006 | Cain |
| 2007/0016265 | A1 | 1/2007 | Davoodi et al. |
| 2007/0136093 | A1 | 6/2007 | Rankin et al. |
| 2007/0256551 | A1 | 11/2007 | Knapp et al. |
| 2010/0278364 | A1 | 11/2010 | Berg |
| 2012/0086551 | A1 | 4/2012 | Lowe et al. |
| 2012/0090446 | A1 | 4/2012 | Moreno |
| 2012/0177233 | A1 | 7/2012 | Kidmose et al. |
| 2013/0041419 | A1 | 2/2013 | Kilgard et al. |
| 2013/0072996 | A1 | 3/2013 | Kilgard et al. |
| 2013/0289653 | A1 | 10/2013 | Kilgard et al. |
| 2013/0296637 | A1 | 11/2013 | Kilgard et al. |
| 2014/0105431 | A1 | 4/2014 | Berg |
| 2014/0228908 | A1 | 8/2014 | Kilgard et al. |
| 2014/0257132 | A1 | 9/2014 | Kilgard et al. |
| 2014/0257430 | A1 | 9/2014 | Kilgard et al. |
| 2015/0065838 | A1 | 3/2015 | Wingeier et al. |
| 2015/0066104 | A1 | 3/2015 | Wingeier et al. |
| 2015/0073492 | A1 | 3/2015 | Kilgard et al. |
| 2015/0126845 | A1 | 5/2015 | Jin et al. |
| 2015/0150498 | A1 | 6/2015 | George et al. |
| 2015/0150499 | A1 | 6/2015 | George et al. |
| 2015/0150501 | A1 | 6/2015 | George et al. |
| 2015/0215693 | A1 | 7/2015 | Sandanger |
| 2015/0281822 | A1 | 10/2015 | Berg |
| 2015/0312665 | A1 | 10/2015 | Berg |
| 2015/0360030 | A1* | 12/2015 | Cartledge .......... A61N 1/36036 607/60 |
| 2016/0015280 | A1 | 1/2016 | Hyde et al. |
| 2016/0015972 | A1 | 1/2016 | Hyde et al. |
| 2016/0022981 | A1 | 1/2016 | Wingeier et al. |
| 2016/0058644 | A1 | 3/2016 | Cheatham, III et al. |
| 2016/0100676 | A1 | 4/2016 | Sandanger |
| 2016/0120733 | A1 | 5/2016 | Ishikawa et al. |
| 2016/0120734 | A1 | 5/2016 | Ishikawa et al. |
| 2016/0205456 | A1 | 7/2016 | Berg |
| 2016/0220808 | A1 | 8/2016 | Hyde et al. |
| 2016/0279435 | A1* | 9/2016 | Hyde ................ A61N 1/36036 |

OTHER PUBLICATIONS

U.S. Appl. No. 15/381,360, Goodall et al.

Anthony, Sebastian; "Foc.us: The first commercial tDCS headset that lets you safely overclock your brain"; ExtremeTech.com; Jul. 30, 2013; pp. 1-2; located at https://www.extremetech.com/extreme/162581-foc-us-the-first-commercial-tdcs-headset-that-lets-you-safely-overclock-your-brain.

Boasso et al.; "Transdermal electrical neuromodulation of the trigeminal sensory nuclear complex improves sleep quality and mood"; Mar. 15, 2016; pp. 1-16; located at: http://dx.doi.org/10.1101/043901.

Buchanan et al.; "Neuromusculoskeletal Modeling: Estimation of Muscle Forces and Joint Moments and Movements From Measurements of Neural Command"; J Appl Biomech; Nov. 2004; pp. 367-395; vol. 20, No. 4.

Bulling et al.; "Eye Movement Analysis for Activity Recognition Using Electrooculography"; IEEE Transactions on Pattern Analysis and Machine Intelligence; Apr. 2011; pp. 741-753; vol. 33, No. 4; IEEE.

Cogiamanian et al.; "Improved isometric force endurance after transcranial direct current stimulation over the human motor cortical areas"; European Journal of Neuroscience; Jul. 2007; pp. 242-249; vol. 26, Issue 1 (Abstract Only).

Dawson et al.; "Safety, Feasibility, and Efficacy of Vagus Nerve Stimulation Paired With Upper-Limb Rehabilitation After Ischemic Stroke"; Stroke; Jan. 2016; pp. 143-150.

De Ridder et al.; "Safety and Efficacy of Vagus Nerve Stimulation Paired With Tones for the Treatment of Tinnitus: A Case Series"; Neuromodulation: Technology at the Neural Interface; Feb. 2014; pp. 170-179; vol. 17, Issue 2; International Neuromodulation Society (Abstract Only).

Engineer et al.; "Reversing pathological neural activity using targeted plasticity"; Nature; Feb. 3, 2011; pp. 101-104; vol. 470, No. 7332; Macmillan Publishers Limited.

Fritsch et al.; "Direct Current Stimulation Promotes BDNF-Dependent Synaptic Plasticity: Potential Implications for Motor Learning"; Neuron; Apr. 29, 2010; pp. 198-204; vol. 66; Elsevier Inc.

Ganguly et al.; "Activity-Dependent Neural Plasticity from Bench to Bedside"; Neuron; Oct. 30, 2013; pp. 729-741; vol. 80; Elsevier Inc.

Guse et al.; "Cognitive effects of high-frequency repetitive transcranial magnetic stimulation: a systematic review"; J Neural Transm; 2010; pp. 105-122; vol. 117; Springer-Verlag.

Gutterman, Amanda; "Nervana: This Startup Gets You High on Dopamine, No Exercise Required"; Futurism.com; Jan. 12, 2016; pp. 1-9; located at https://futurism.com/this-startup-gets-you-high-on-dopamine-no-exercise-required/.

Halo Neuroscience; "A Real-World Investigation into the Benefits of Transcranial Direct Current Stimulation to the Primary Motor Cortex on Muscular Performance in Elite Athletes"; Feb. 10, 2016; pp. 1-8.

Halo Neuroscience; "Bihemispheric Transcranial Direct Current Stimulation with Halo Neurostimulation System over Primary Motor Cortex Enhances Fine Motor Skills Learning in a Complex Hand Configuration Task"; Feb. 10, 2016; pp. 1-6.

Halo Neuroscience; "Bihemispheric Transcranial Direct Current Stimulation with Halo Neurostimulation System over Primary Motor Cortex Enhances Rate of Force Development in an Isometric Lateral Pinch Force Task"; Feb. 10, 2016; pp. 1-7.

Halo Neuroscience; "Safety of Non-Invasive Brain Stimulation delivered via the Halo Neurostimulation System in Healthy Human Subjects"; Feb. 10, 2016; pp. 1-5.

Halo Neuroscience; "Science FAQ's"; printed on Apr. 29, 2016; pp. 1-5; located at https://www.halocuro.com/science-faqs.

Hays et al.; "Targeting Plasticity with Vagus Nerve Stimulation to Treat Neurological Disease"; Chapter 11 from Progress in Brain Research, vol. 207; 2013; pp. 1-26; Elsevier.

Hummel et al.; "Effects of non-invasive cortical stimulation on skilled motor function in chronic stroke"; Brain; 2005; pp. 490-499; vol. 128; Oxford University Press.

Julian et al.; "The Effects of Mechanical Stimulation on Some Electrical Properties of Axons"; The Journal of General Physiology; Nov. 1, 1962; pp. 297-313; vol. 46, No. 2.

Kim et al.; "Facilitative effect of high frequency subthreshold repetitive transcranial magnetic stimulation on complex sequential motor learning in humans"; Neuroscience Letters; Sep. 2, 2004; pp. 181-185; vol. 367, Issue 2; Elsevier Ireland Ltd. (Abstract Only).

Legon et al.; "Pulsed Ultrasound Differentially Stimulates Somatosensory Circuits in Humans as Indicated by EEG and fMRI"; PLOS ONE; Dec. 2012; pp. 1-14; vol. 7, Issue 12, No. e51177.

Lewis et al.; "Design and Evaluation of a Wearable Self-Applied Therapeutic Ultrasound Device for Chronic Myofascial Pain"; Ultrasound in Med. & Biol.; 2013; pp. 1429-1439; vol. 39, No. 8; World Federation for Ultrasound in Medicine & Biology.

Lozano, Andres M.; "Harnessing Plasticity to Reset Dysfunctional Neurons"; The New England Journal of Medicine; Apr. 7, 2011; pp. 1367-1368; vol. 364, No. 14.

McIntyre et al.; "Interacting Brain Systems Modulate Memory Consolidation"; Neurosci Biobehav Rev.; Aug. 2012; pp. 1750-1762; vol. 36, No. 7; Elsevier Ltd.

Medical Xpress; "New disposable biosensor may help physicians determine which patients can safely be fed following surgery"; Aug. 7, 2014; pp. 1-4; located at http://medicalxpress.com/news/2014-08-disposable-biosensor-physicians-patients-safely.html.

Nelson et al.; "The Effects of Transcranial Direct Current Stimulation (tDCS) on Multitasking Throughput Capacity"; Frontiers in Human Neuroscience; Nov. 29, 2016; pp. 1-13; vol. 10, Article 589.

(56) References Cited

OTHER PUBLICATIONS

Neuroscientist News; "Neuroscientists working to test brain training claims"; Apr. 5, 2016; pp. 1-6; located at http://www.neuroscientistnews.com/clinical-update/neuroscientists-working-test-brain-training-claims.

Nitsche et al.; "Excitability changes induced in the human motor cortex by weak transcranial direct current stimulation"; J Physiol.; Sep. 15, 2000; pp. 633-639; vol. 527, Pt. 3 (Abstract Only).

Nitsche et al.; "Facilitation of Implicit Motor Learning by Weak Transcranial Direct Current Stimulation of the Primary Motor Cortex in the Human"; Journal of Cognitive Neuroscience; 2003; pp. 619-626; vol. 15, No. 4; Massachusetts Institute of Technology.

Priori et al.; "Polarization of the human motor cortex through the scalp"; Neuroreport; Jul. 13, 1998; pp. 2257-2260; vol. 9, No. 10 (Abstract Only).

Reis, et al.; "Noninvasive cortical stimulation enhances motor skill acquisition over multiple days through an effect on consolidation"; PNAS; Feb. 3, 2009; pp. 1590-1595; vol. 106, No. 5; The National Academy of Sciences of the USA.

Rogers, Bruce; "Daniel Chao's Halo Neuroscience Builds Headset to Train Your Brain"; Forbes.com; Apr. 29, 2016; pp. 1-4; located at: http://www.forbes.com/sites/brucerogers/2016/04/29/daniel-chaos-halo-neuroscience-builds-headset-to-train-your-brain/#2b603f832bc4.

Rong et al.; "Transcutaneous vagus nerve stimulation for the treatment of depression: a study protocol for a double blinded randomized clinical trial"; BMC Complementary and Alternative Medicine; 2012; pp. 1-6.

Sellaro et al.; "Transcutaneous Vagus Nerve Stimulation Enhances Post-error Slowing"; Journal of Cognitive Neuroscience; 2015; pp. 2126-2132; vol. 27, No. 11; Massachusetts Institute of Technology.

Song et al.; "Electrooculogram Signals Analysis for Process Control Operator Based on Fuzzy c-Means"; International Journal of Advanced Computer Science and Applications; 2015; pp. 138-142; vol. 6, No. 9.

Tanaka et al.; "Enhancement of pinch force in the lower leg by anodal transcranial direct current stimulation"; Exp Brain Res; 2009; pp. 459-465; vol. 196; Springer.

Terney et al.; "Increasing Human Brain Excitability by Transcranial High-Frequency Random Noise Stimulation"; The Journal of Neuroscience; Dec. 24, 2008; pp. 14147-14155; vol. 28, No. 52; Society for Neuroscience.

Udina, et al.; "Effects of activity-dependent strategies on regeneration and plasticity after peripheral nerve injuries"; Annals of Anatomy; 2011; pp. 347-353; Elsevier GmbH.

Vanderbilt School of Engineering; "Alum's Nervana earbuds use nerve stimulation for blissful listening; debut to rave reviews"; Apr. 28, 2016; pp. 1-6; located at: http://engineering.vanderbilt.edu/news/2016/alums-nervana-earbuds-use-nerve-stimulation-for-blissful-listening-debut-to-rave-reviews/.

Velstra et al.; "Prediction and stratification of upper limb function and self-care in acute cervical spinal cord injury with the graded redefined assessment of strength, sensibility, and prehension (GRASSP)"; Neurorehabil Neural Repair; Sep. 2014; pp. 632-642; vol. 28, No. 7 (Abstract Only).

Waters-Metenier et al.; "Bihemispheric Transcranial Direct Current Stimulation Enhances Effector-Independent Representations of Motor Synergy and Sequence Learning"; The Journal of Neuroscience; Jan. 15, 2014; pp. 1037-1050; vol. 34, No. 3.

Wilson-Pauwels et al.; "Cranial Nerves in Health and Disease, Second Edition"; 2002 pp. i-ix, 1-245, cover, and back cover, BC Decker Inc.; Hamilton, Ontario, Canada.

\* cited by examiner

FIG. 13

1300 A computer program product

1302 A non-transitory computer-readable medium 1304
one or more instructions for generating, under control of electrical control circuitry, a least one stimulus control signal for controlling delivery of a transcutaneous neural stimulus to a peripheral neural structure located at least in part in or on an ear of a subject via a neural stimulator fitted in or on at least a portion of the ear of a subject;

one or more instructions for delivering, via a prompting system under control of the electrical control circuitry, at least one prompt for prompting the subject to repeatedly perform a specific activity;

one or more instructions for controlling a timing of delivery of the transcutaneous neural stimulus with respect to the at least one prompt; and one or more instructions for controlling a number of repetitions of the specific activity that the subject is prompted to perform by the at least one prompt.

1306 a recordable medium

FIG. 16
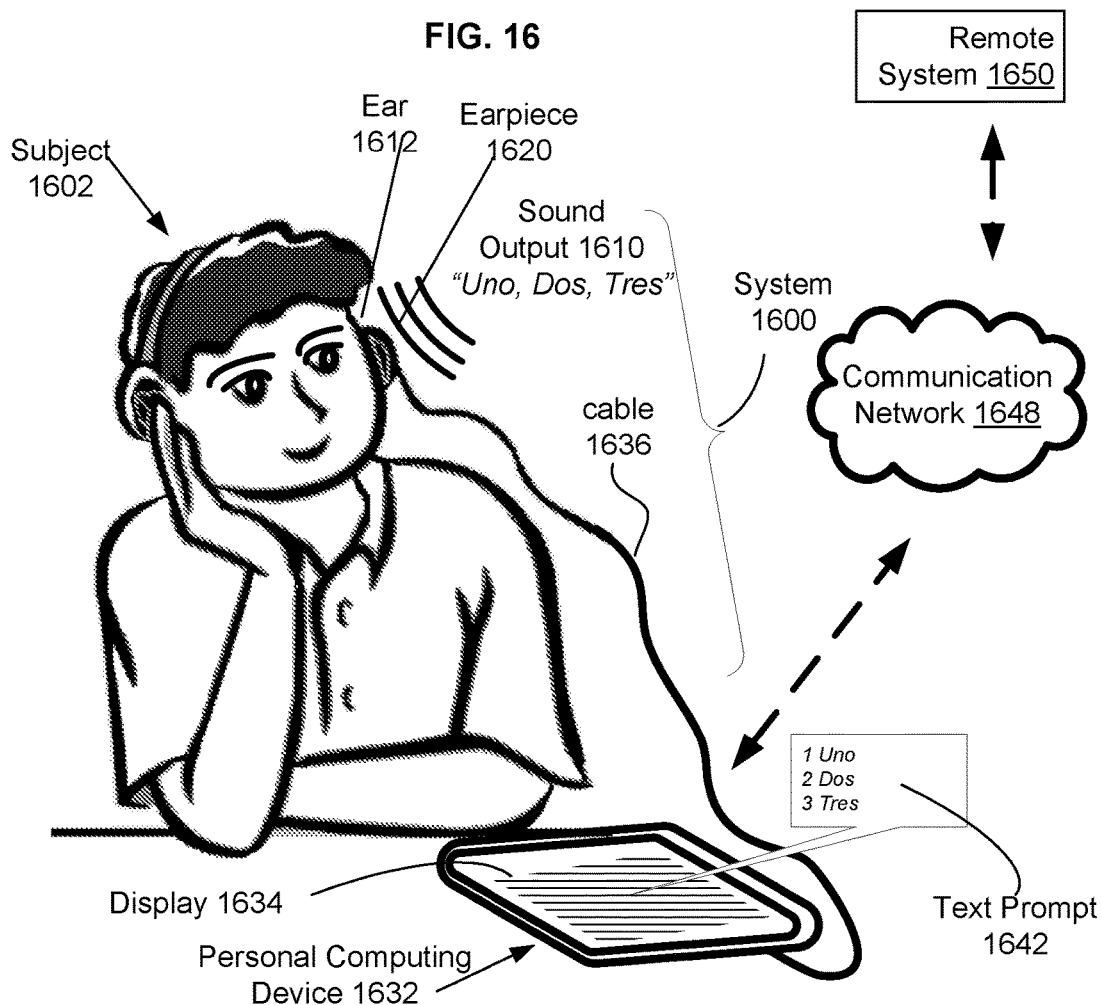
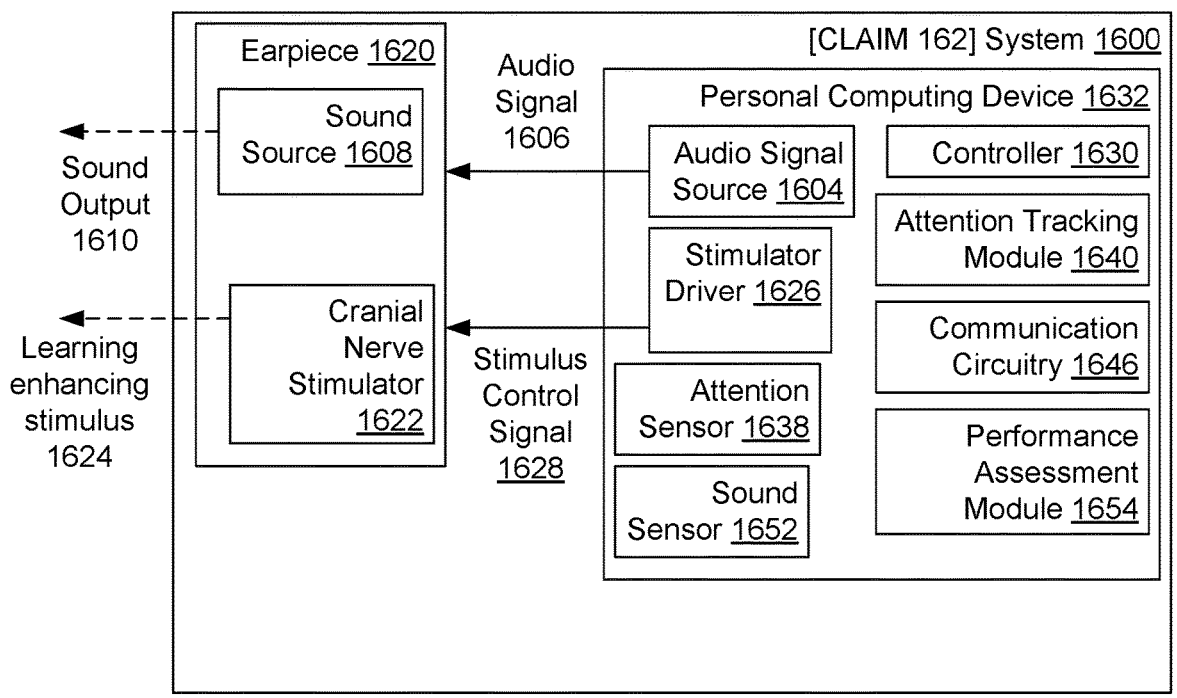

FIG. 24

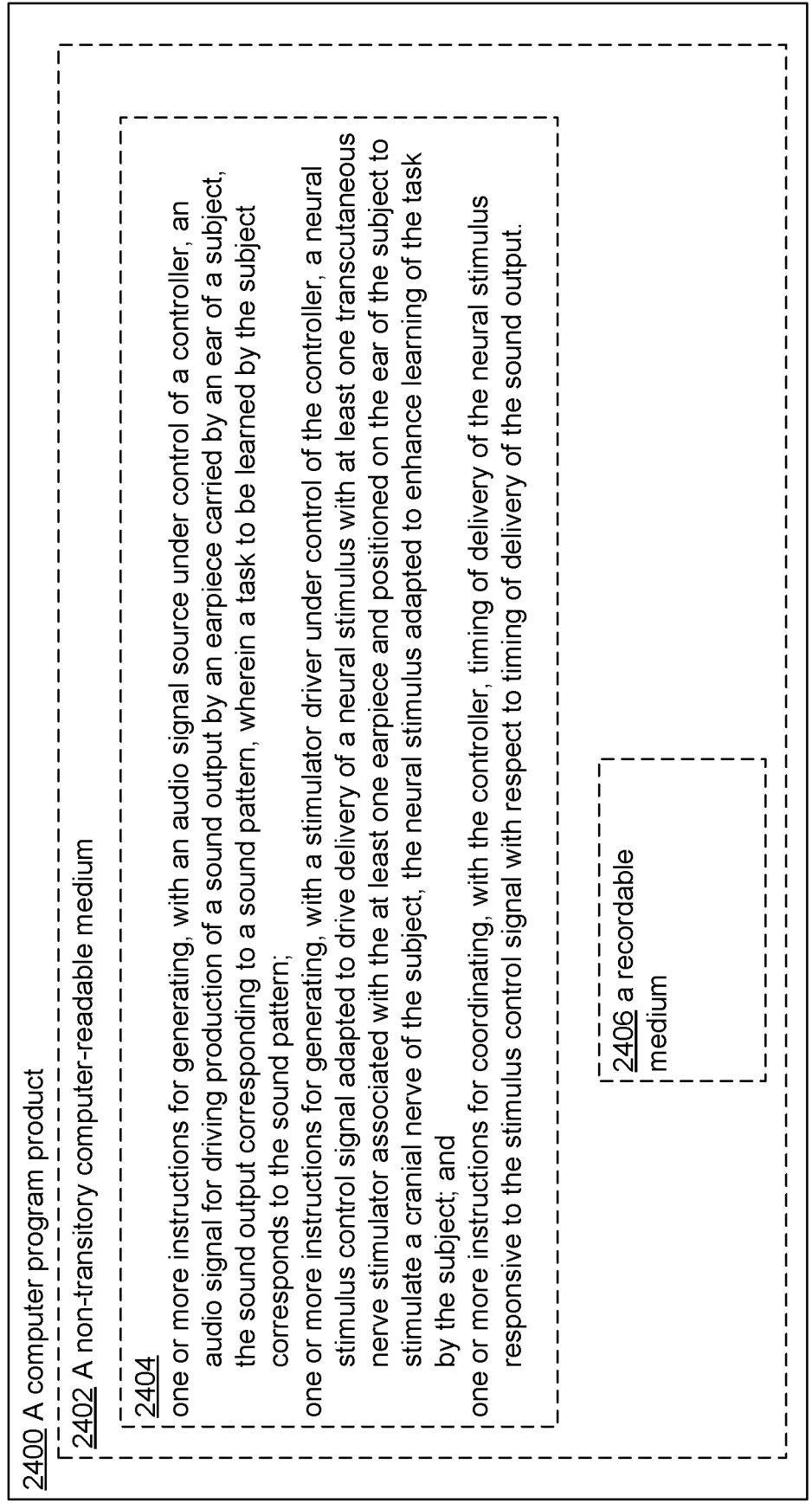

2400 A computer program product

2402 A non-transitory computer-readable medium 2404
one or more instructions for generating, with an audio signal source under control of a controller, an audio signal for driving production of a sound output by an earpiece carried by an ear of a subject, the sound output corresponding to a sound pattern, wherein a task to be learned by the subject corresponds to the sound pattern;

one or more instructions for generating, with a stimulator driver under control of the controller, a neural stimulus control signal adapted to drive delivery of a neural stimulus with at least one transcutaneous nerve stimulator associated with the at least one earpiece and positioned on the ear of the subject to stimulate a cranial nerve of the subject, the neural stimulus adapted to enhance learning of the task by the subject; and one or more instructions for coordinating, with the controller, timing of delivery of the neural stimulus responsive to the stimulus control signal with respect to timing of delivery of the sound output.

2406 a recordable medium

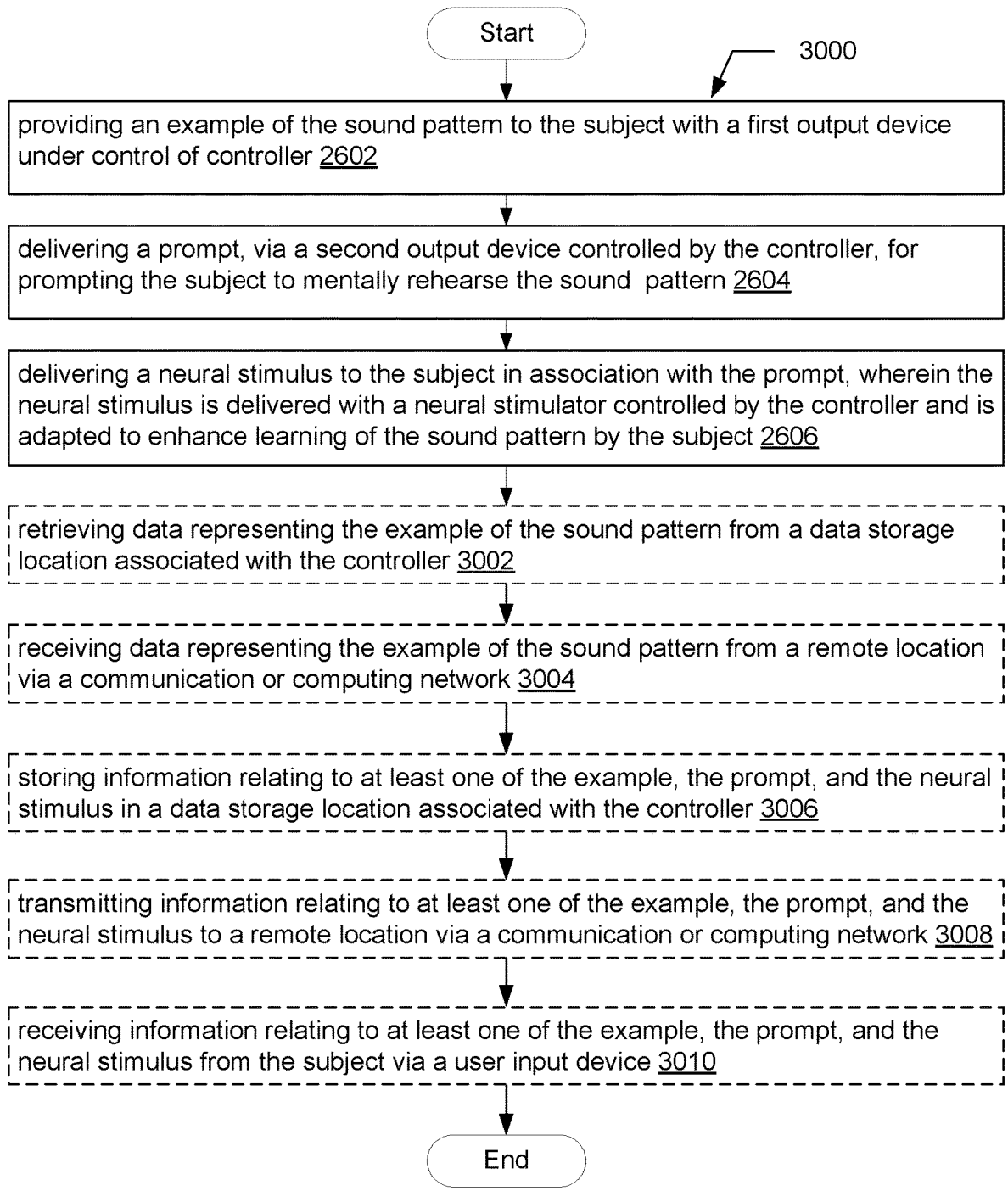

FIG. 31

3100 A computer program product

3102 A non-transitory computer-readable medium 3104
one or more instructions for providing an example of the sound pattern to the subject with a first output device under control of controller;
one or more instructions for delivering a prompt, via a second output device controlled by the controller, for prompting the subject to mentally rehearse the sound pattern; and
one or more instructions for delivering a neural stimulus to the subject in association with the prompt, wherein the neural stimulus is delivered with a neural stimulator controlled by the controller and is adapted to enhance learning of the sound pattern by the subject.

3106 a recordable medium

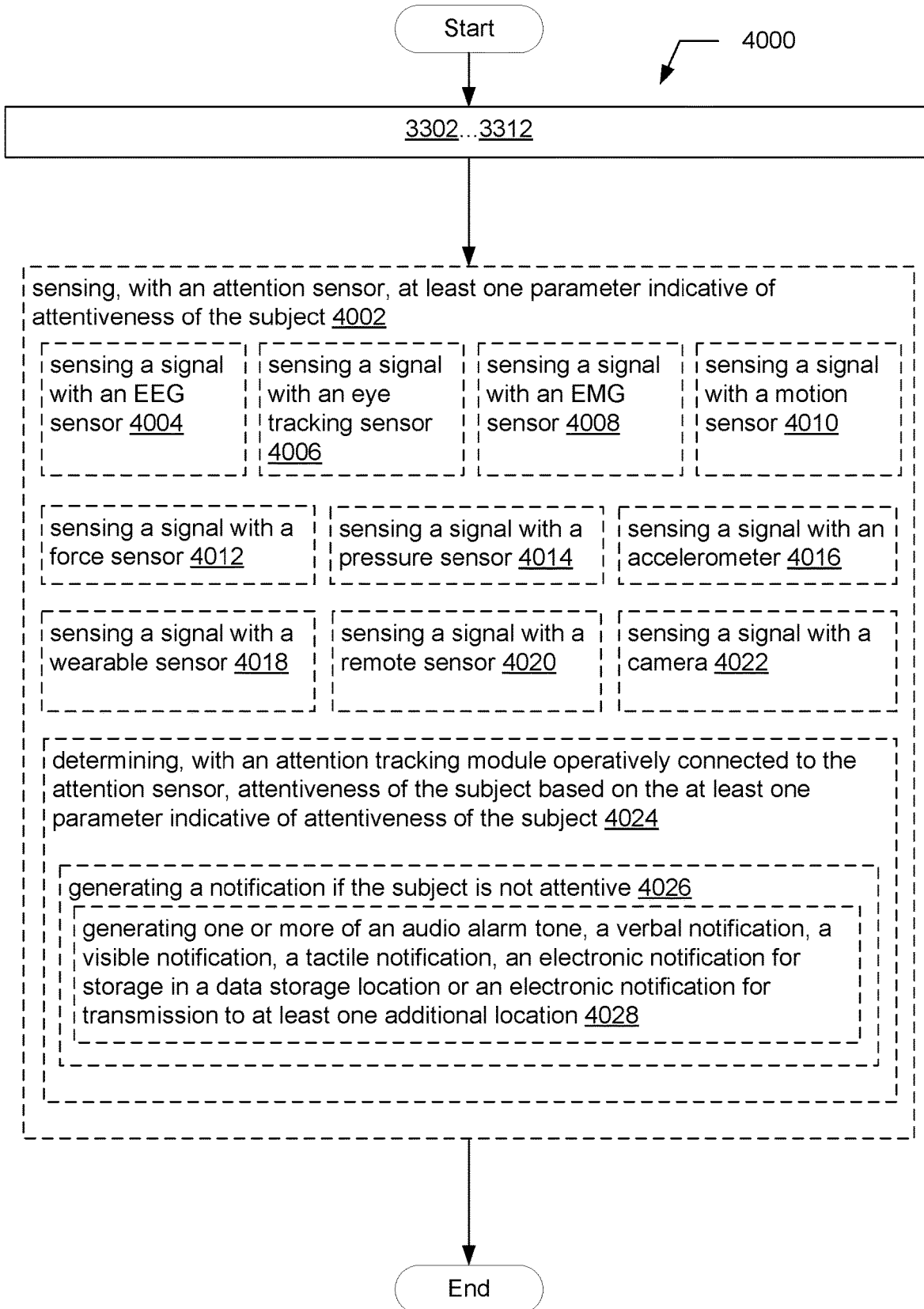

FIG. 41

4100 A computer program product

4102 A non-transitory computer-readable medium

4104 one or more instructions for presenting to a subject, via at least one of an audio output device and a visual output device under control of a controller of a personal computing device, a priming example of a complex motor task, the complex motor task including activation of a plurality of muscles;

one or more instructions for instructing the subject, via at least one of an audio output device and a visual output device under control of the controller, to mentally rehearse the complex motor task during at least one presentation of a rehearsal example of the complex motor task;

one or more instructions for providing to the subject, via at least one of an audio output device and a visual output device under control of the controller, a notification to the subject of a start of at least one presentation of the rehearsal example;

one or more instructions for presenting to the subject, via at least one of an audio output device and a visual output device under control of the controller, the rehearsal example;

one or more instructions for delivering to the subject, via a neural stimulus source under control of the controller, a learning enhancing neural stimulus during or immediately after at least one presentation of the rehearsal example; and one or more instructions for repeating, under control of the controller, presenting the rehearsal example to the subject for a training period.

4106 a recordable medium

PROMPTING SYSTEM AND METHOD FOR ENHANCING LEARNING WITH NEURAL MODULATION

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system for enhancing learning of an activity includes, but is not limited to, a housing configured to fit in or on at least a portion of an ear of a subject, a neural stimulator located in or on the housing and configured to deliver a transcutaneous neural stimulus to a peripheral neural structure located at least in part in or on the ear of the subject, a prompting system configured to deliver at least one prompt for prompting the subject to repeatedly perform a specific activity, and electrical control circuitry including stimulator control circuitry adapted to generate at least one stimulus control signal for controlling delivery of the transcutaneous neural stimulus to the peripheral neural structure with the neural stimulator, prompter control circuitry adapted to generate at least one prompt control signal for controlling delivery of the prompt by the prompting system, and timing control circuitry for controlling a number of repetitions of the specific activity that the subject is prompted to perform by the at least one prompt and timing of delivery of the transcutaneous neural stimulus with respect to the at least one prompt. In addition to the foregoing, other system aspects are described in the claims, drawings, and text forming a part of the disclosure set forth herein.

In an aspect, a method of enhancing learning includes, but is not limited to, delivering, with a neural stimulator housed in a housing fitted in or on at least a portion of an ear of a subject, a transcutaneous neural stimulus to a peripheral neural structure located at least in part in or on the ear of a subject, wherein the neural stimulator is controlled by electrical control circuitry operably coupled to the neural stimulator; delivering, with a prompting system under control of the electrical control circuitry, at least one prompt to the subject for prompting the subject to repeatedly perform a specific activity, wherein the electrical control circuitry is operably coupled to the prompting system; controlling, with the electrical control circuitry a timing of delivery of the transcutaneous neural stimulus with respect to the at least one prompt; and a number of repetitions of the specific activity that the subject is prompted to perform by the at least one prompt. In addition to the foregoing, other method aspects are described in the claims, drawings, and text forming a part of the disclosure set forth herein.

In an aspect, a computer program product includes, but is not limited to, at least one non-transitory computer-readable medium bearing one or more instructions for generating, under control of electrical control circuitry, a least one stimulus control signal for controlling delivery of a transcutaneous neural stimulus to a peripheral neural structure located at least in part in or on an ear of a subject via a neural stimulator fitted in or on at least a portion of the ear of a subject; one or more instructions for delivering, via a prompting system under control of the electrical control circuitry, at least one prompt for prompting the subject to repeatedly perform a specific activity; one or more instructions for controlling a timing of delivery of the transcutaneous neural stimulus with respect to the at least one prompt; and one or more instructions for controlling a number of repetitions of the specific activity that the subject is prompted to perform by the at least one prompt. In addition to the foregoing, other aspects of a computer program product are described in the claims, drawings, and text forming a part of the disclosure set forth herein.

In an aspect, a system for enhancing learning includes but is not limited to, a noninvasive device for stimulating a cranial nerve of a subject, the device including at least one transcutaneous nerve stimulator; at least one neural sensor adapted to sense at least one neural activity of the subject; a prompting system configured to deliver at least one prompt for prompting the subject to repeatedly perform a specific activity; and electrical control circuitry including stimulator control circuitry adapted to generate at least one stimulus control signal for controlling delivery of a transcutaneous neural stimulus to the cranial nerve with the transcutaneous neural stimulator; prompter control circuitry adapted to generate at least one prompt control signal for controlling delivery of the prompt by the prompting system; and timing control circuitry for controlling a number of repetitions of the specific activity that the subject is prompted to perform by the at least one prompt and timing of delivery of the transcutaneous neural stimulus with respect to the at least one prompt. In addition to the foregoing, other system aspects are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 13 is a block diagram of a computer program product relating to the method of FIG. 5.
FIG. 16 depicts another embodiment of a training system.
FIG. 24 is a block diagram of a computer program product relating to the method of FIG. 17.
FIG. 30 is a flow diagram of a method.
FIG. 31 is a block diagram of a computer program product relating to the method of FIG. 26.
FIG. 40 is a flow diagram of a method.
FIG. 41 is a block diagram of a computer program product relating to the method of FIG. 33.

DETAILED DESCRIPTION

Figure 1:
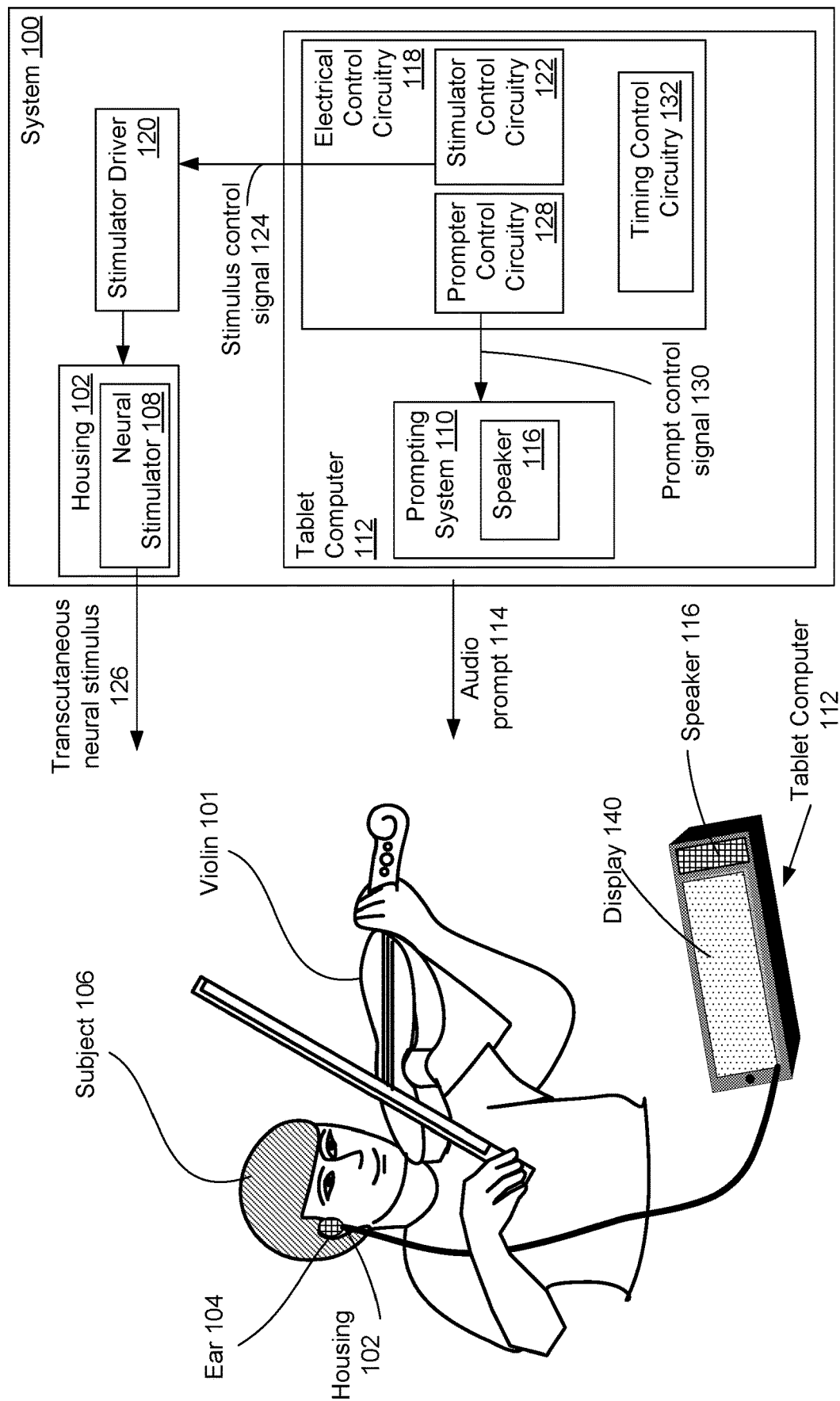
FIG. 1 illustrates a system for enhancing learning.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts an example of a system 100 for enhancing learning of an activity. (In FIG. 1 and other figures herein, system components are depicted both in an illustration and in block diagram form, to more clearly show all components and how they interact. Elements that appear in both the illustration and the block diagram are identified with the same reference number in each). In the example of FIG. 1, the activity is playing a violin 101. System 100 includes a housing 102 configured to fit in or on at least a portion of an ear 104 of a subject 106, and a neural stimulator 108 located in or on housing 102. Neural stimulator 108 is configured to deliver a transcutaneous neural stimulus to a peripheral neural structure located at least in part in or on the ear 104 of subject 106, for example as described in U.S. Published Patent Application No. 2016/0279435 to Hyde et al., which is incorporated herein by reference. System 100 also includes a prompting system 110, implemented on a tablet computer 112, which is configured to deliver at an audio prompt 114, via speaker 116, for prompting subject 106 to repeatedly perform a specific activity (i.e. and activity related to playing violin 101), and electrical control circuitry 118, which includes control circuitry of tablet computer 112 and circuitry of stimulator driver 120 for driving neural stimulator 108. Stimulator driver 120 includes additional driver circuitry that may be used in combination with tablet computer 112 to generate a driving signal sufficient to drive neural stimulator 108. Electrical control circuitry 118 includes stimulator control circuitry 122 adapted to generate at least one stimulus control signal 124 for controlling delivery of the transcutaneous neural stimulus 126 to the peripheral neural structure with the neural stimulator 108, prompter control circuitry 128 adapted to generate at least one prompt control signal 130 for controlling delivery of the prompt 114 by the prompting system 110, and timing control circuitry 132 for controlling a number of repetitions of the specific activity that the subject is prompted to perform by the at least one prompt and timing of delivery of the transcutaneous neural stimulus with respect to the at least one prompt. Specifically, prompting system 110 includes display 140 and speaker 116. As an example, if system 100 is being used by subject 106 to practice playing a scale on violin 101, audio prompt 114 is a brief tone which prompts subject 106 to play the scale. Neural stimulation is delivered to subject 106 in fixed temporal relationship with the tone. The tone is delivered repeatedly, at intervals such that subject 106 plays the scale once with each repetition of the tone. Display 140 of tablet computer 112 is used to provide instructions to subject 106. For example, after each repetition, subject 106 is informed of the number of repetitions that have been completed and the number yet to be completed. These and other functions of system 100 and other learning systems are described herein below.

Figure 2:
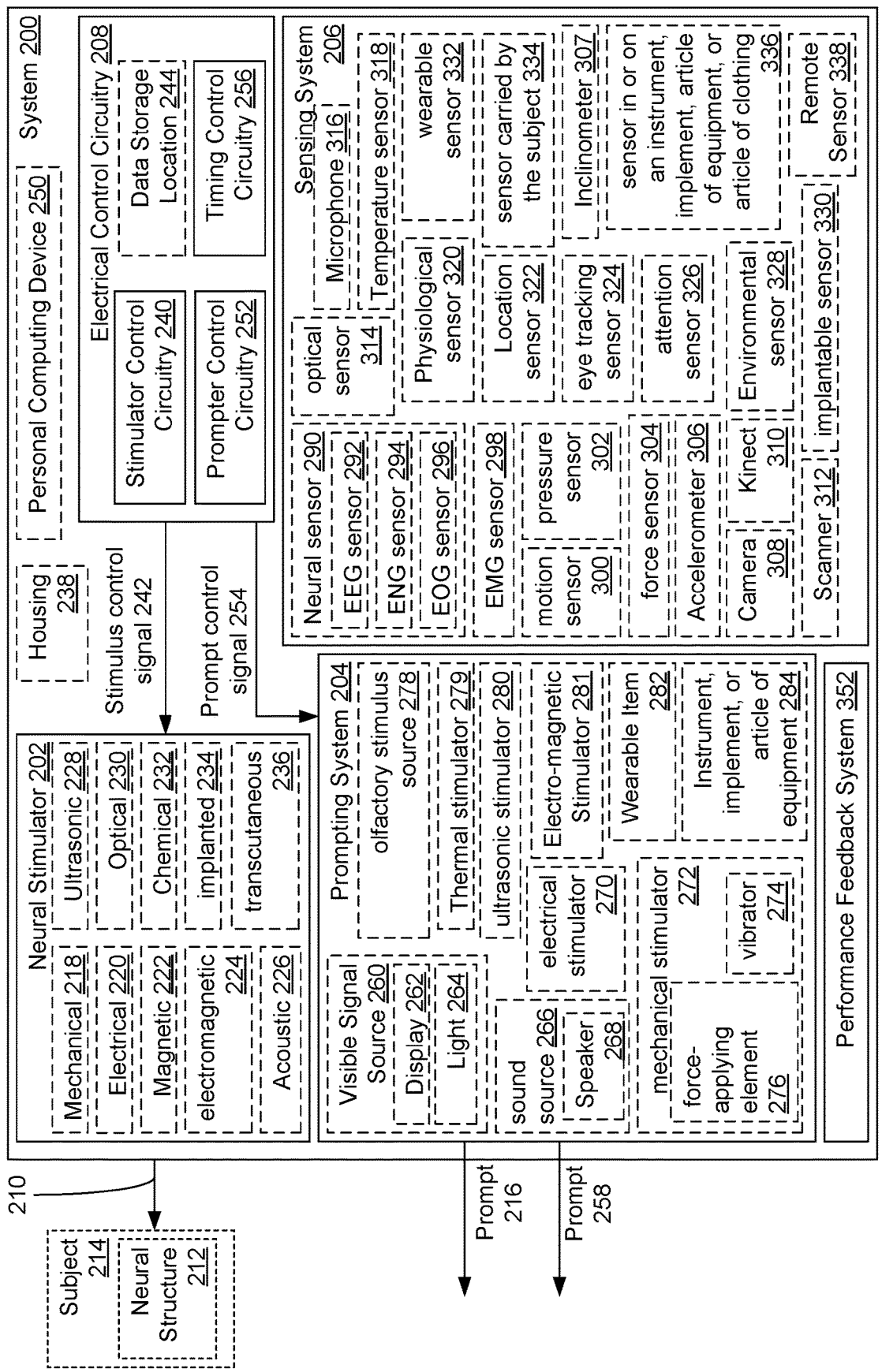
FIG. 2 is a block diagram of a system for enhancing learning.

FIG. 2 is a block diagram of a system 200 for enhancing learning of an activity, which is a generalization of a system of the type depicted in FIG. 1. FIG. 2 shows additional, alternative, or optional components that may be used in connection with a system as depicted in FIG. 1, or in other systems for enhancing learning, additional examples of which are described elsewhere herein, with specific examples provided in FIGS. 14, 15, 16, 25, and 32.

System 200 includes at least one neural stimulator 202, prompting system 204, sensing system 206, and electrical control circuitry 208. Neural stimulator 202 is used to deliver a neural stimulus 210 to a neural structure 212 of a subject 214. Prompting system 204 prompts subject 214 to perform an activity. Operation of neural stimulator 202 and prompting system 204 is controlled by electrical control circuitry 208.

Neural stimulation is used to enhance learning or memory of a desired activity or skill, and, in some cases, block learning of an undesired activity. In an aspect, a "desired activity" is correct performance of a task, and an "undesired activity" is incorrect performance of a task, for example, a mental or physical (motor) task. In an aspect, neural stimulation can be used to enhance or reinforce learning of a desirable response to a stimulus, or to block or suppress learning of an undesirable response to a stimulus. A response may be an emotional response, a sensory response, a physiological response, or a reflexive response, for example. In various aspects, systems described herein can be used for reducing neuropathy (including autonomic neuropathy), tinnitus, sexual dysfunction, and/or neuropathic pain. In various aspects, systems described herein can be used to learn a new skill or enhance a skill (e.g., playing an instrument, performing a sports action, speaking a language, performing a math function) or to re-learn a skill, for example during rehabilitation treatment for a brain disorder (e.g., stroke or injury), nerve damage, or other physical dysfunction. In various aspects, systems described herein can be used to entrain or enhance memory such as for memory recall, to aide in memorization (e.g., of a verbal, musical, or physical performance; vocabulary; facts; numbers such as a telephone number or combination; mathematical equations; etc.), to learn or enhance cognitive skills (e.g., thinking, reasoning, reading, memory, etc.), and the like. In various aspects, systems described herein can be part of a medical therapeutic system or regimen administered by a health care provider. In various aspects, systems described herein can constitute or be part of a recreational system. In various aspects, systems described herein can constitute or be part of a consumer product.

Various neural structures can be stimulated to enhance learning, including peripheral and/or cranial nerves as well as selected brain structures. Methods for delivering vagus nerve stimulation are described in S. A. Hays, R. L. Rennaker, M. P. Kilgard, "Targeting Plasticity with Vagus Nerve Stimulation to Treat Neurological Disease" in M. M. Merzenich, M. Nahum, and T. M. Van Vleet, Editors: *Progress in Brain Research*, Vol. 207, Burlington: Academic Press, 2013, pp. 275-299, ISBN: 978-0-444-63327-9, which is incorporated herein by reference. For example, this reference describes using vagus nerve stimulation in connection with motor task training (pressing lever and spinning wheel to receive food reward, by rats), cognitive task training (recall of highlighted words in paragraph by humans), relearning of sensory processing (remapping sensory cortex to reverse chronic tinnitus) or correcting of cognitive dysfunctions (normalizing hypersensitive responses to stimuli in PTSD in humans). For example, U.S. Patent Application 2015/0066104 to Wingeier et al., which is incorporated herein by reference, describes approaches to delivering transcranial electrical stimulation to the brain. A. M. Boasso, H. Mortimore, R. Silva, L. Aven, W. J. Tyler, "Transdermal electrical neuromodulation of the trigeminal sensory nuclear complex improves sleep quality and mood," bioRxiv preprint first posted online Mar. 15, 2016; doi: http://dx.doi.org/10.1101/043901, which is incorporated herein by reference, describes transdermal modulation of the trigeminal nerve to improve sleep, and mood and decrease stress, to improve mental health and performance. C. K. McIntyre, J. L. McGaugh, and C. L. Williams, "Interacting Brain Systems Modulate Memory Consolidation," Neurosci Biobehav. Re. 2012, August; 36(7):1750-1762. doi:10.1016/j.neubiorev.2011.11.0001, which is incorporated herein by reference, describes the role of emotional arousal, and corresponding release of epinephrine and glucocorticoids on enhancing consolidation of long term memories (and conversely, disrupting memory consolidation by blocking corresponding hormone receptors). Similarly, blocking activation or conduction in neural structures associated with emotional arousal (e.g., the vagus nerve, trigeminal nerve) may serve to limit memory consolidation. Systems and methods for generating blocks in peripheral neural structures are described, for example, in U.S. Pat. No. 9,358,374 to Dacey et al., which is incorporated herein by reference. While numerous methods and systems for neural modulation are described here, the description is not exhaustive. Any conventional method and system for modulating (at least partially blocking or stimulating) the activation or conduction of neural structures can be used with the systems and methods described and claimed herein.

In an aspect, neural structure 212 is a cranial nerve. In some aspects, neural structure 212 is located at least in part in or on the ear of the subject.

In an aspect, neural stimulator 202 is configured to stimulate a cranial nerve innervating an ear of a subject, for example as described in U.S. Published Patent Application No. 2016/0279435 to Hyde et al., which is incorporated herein by reference. Nerves innervating the skin on or in the vicinity of the ear of the subject include, e.g., the facial nerve (cranial nerve VII), the glossopharyngeal nerve (cranial nerve IX), the auricular branch of the vagus nerve (cranial nerve X), the auriculotemporal branch of trigeminal nerve (cranial nerve V), the lesser occipital nerve (spinal nerve C3), and the greater auricular nerve (spinal nerves C2, C3).

Neural stimulator 202 can includes various types of neural stimuluator, including but not limited to, mechanical 218, electrical 220, magnetic 222, electromagnetic 224, acoustic 226, ultrasonic 228, optical 230, or chemical 232 stimulators. In an aspect, neural stimulator 202 can include multiple neural stimulators. If multiple neural stimulators are used, they may all be of the same type, or may be of several different types. Neural stimulator 202 can be an implanted stimulator 234, or a transcutaneous stimulator 236. Various types of transcutaneous and implantable neural stimulators are described in U.S. Published Patent Applications 2015/0360060 to Cartledge et al., U.S. Published Patent Application No. 2016/0279435 to Hyde et al., and U.S. Pat. No. 9,358,374 to Dacey et al., all of which are incorporated herein by reference. Examples of other suitable implantable stimulators include, for example, 'Bion' capsule-type stimulators, as described in U.S. Pat. No. 5,324,316 to Schulman et al., and U.S. Pat. No. 5,515,848 to Corbett, II et al.; flat interface nerve electrodes as described in U.S. Pat. No. 6,456,866 to Tyler et al., and cuff electrodes as described in U.S. Published patent Applications 2015/0073492 to Kilgard et al., all of which are incorporated herein by reference.

A mechanical stimulator may include, for example, a vibratory mechanical stimulator that delivers a cyclical or vibrating mechanical stimulus to the skin of the ear of the subject. Vibratory mechanical stimulators can include, for example, various types of vibrating mechanical devices, e.g., electromechanical, piezoelectric, movable coil, electrostatic, magnetostrictive, isodynamic, and/or MEMS devices, for example as used for manufacturing small-scale speakers and microphones. An electrical stimulator 220 may include, for example, an electrode or electrical contact designed for contacting the skin surface, for example as described in Rong et al., "Transcutaneous vagus nerve stimulation for the treatment of depression: a study protocol for a double blinded randomized clinical trial," BMC Complementary and Alternative Medicine 2012, 12:255, which is incorporated herein by reference. In an aspect, magnetic stimulator 222 includes one or more coil through which electrical current is passed to generate a magnetic field. The magnetic field induces electrical currents within the tissue in/around the ear of the subject to activate neural structures. In an aspect, neural stimulator 202 includes an ultrasonic stimulator 228, for example as described in Legon et al., "Pulsed Ultrasound Differentially Stimulates Somatosensory Circuits in Humans as Indicated by EEG and fMRI," PLOS ONE 7(12): e5177. Doi:10.01371/journal.pone.0051177, December 2012, which is incorporated herein by reference. In some aspects, other types of neural stimulators, such as optical stimulator 230 or chemical stimulator 232 are used. See, for example, stimulators described in U.S. Pat. No. 8,171,658 to Dacey, Jr. et al., which is incorporated herein by reference.

In an aspect, neural stimulator 202 is located in a housing 238. In an aspect, housing 238 and neural stimulator 202 are configured to a deliver a transcutaneous neural stimulus to a cranial nerve innervating an ear of the subject; for example, housing 238 is configured to fit on a pinna of the ear of the subject, or at least a portion of housing 238 is configured to fit into an ear canal or concha of the ear of the subject. In some aspects, a neural stimulator is located on an extension that is secured to an earbud but extends beyond the ear of the subject to, e.g. a temple or forehead of the subject. These and other neural stimulator configurations are described in U.S. Published Patent Application No. 2016/0279435 to Hyde et al., filed Mar. 27, 2015, which is incorporated herein by reference. In some aspects, neural stimulator 202 is positioned with respect to the head or neck of the subject with a headband, an earphone, a strap, an adhesive patch, etc. to locate neural stimulator with respect to a cranial nerve, a peripheral nerve, or a brain structure. In other aspects, a neural stimulator is implanted adjacent a cranial nerve, a peripheral nerve, or a brain structure of interest. In an aspect, neural stimuli are delivered to peripheral neural structures to evoke emotional arousal and/or biochemical correlates thereof (e.g., release of norepinephrine and/or corticosterone). In an aspect, neural stimuli are delivered to peripheral neural structures including nerves of the autonomic nervous system (particularly the sympathetic nervous system). In an aspect, neural stimuli are delivered to peripheral neural structures including somatosensory and other sensory neural structures.

In various embodiments described herein, neural stimulator is located on an earbud, earpiece, or headphone. Such devices also be used to deliver sound to the ears of the subject, for use as a prompt, as described herein below. Neural stimulator 202 may be located in or on a housing 238 that contains communication circuitry for wirelessly communicating with other system components, for example a personal computing device (e.g., an audio player, a mobile phone, or a laptop computer). A battery can be provided in housing 238 to power the device for wireless operation. In an aspect, the neural stimulator 202 is positioned with respect to housing 238 such that when housing 238 is worn on the pinna, neural stimulator 202 is positioned over a specific region of the pinna, e.g., a region of the pinna innervated by a cranial nerve, e.g., the vagus nerve, the facial nerve, the trigeminal nerve, or the glossopharyngeal nerve. Positioning of neural stimulator 202 may be selected based upon knowledge of the innervation of the pinna, for example, as provided in references texts such as Cranial Nerves in Health and Disease, by Linda Wilson-Pauwels, Elizabeth J. Akesson, Patricia A. Stewart, and Sian D. Spacey; B C Decker Inc.; 2 edition (Jan. 1, 2002); ISBN-10: 1550091646/ISBN-13: 978-1550091649, which is incorporated herein by reference.

Prompting system 204 is configured to deliver at least one prompt 216. For example, prompt 216 may be used to prompt subject 214 to repeatedly perform a specific activity. Electrical control circuitry 208 includes stimulator control circuitry 240 adapted to generate at least one stimulus control signal 242 for controlling delivery of the neural stimulus 210 with the neural stimulator 202. Neural stimulus 210 may be a transcutaneous neural stimulus, as described in connection with FIG. 1, or other type of neural stimulus as described elsewhere herein.

At least a portion of electrical control circuitry 208 can be implemented on a personal computing device 250. In an aspect, personal computing device 250 is personal digital assistant, a personal entertainment device, a mobile phone, a laptop computer, a tablet personal computer, a wearable computing device (e.g., a fitness band, an item of clothing, attire, or eyewear incorporating computing capability), a networked computer, a computing system comprised of a cluster of processors, a computing system comprised of a cluster of servers, a workstation computer, and/or a desktop computer. In various aspects, personal computing device includes one or more of a portable computing device, a mobile computing device, and a thin client computing device, for example.

Electrical control circuitry 208 includes prompter control circuitry 252 adapted to generate at least one prompt control signal 254 for controlling delivery of prompt 216 by the prompting system 204, and timing control circuitry 256. In an aspect, timing control circuitry 256 controls a number of repetitions of a specific activity that the subject is prompted to perform by the at least one prompt 216, and timing of delivery of the neural stimulus 210 with respect to the at least one prompt 216.

In various aspects, stimulator control circuitry 240 is configured to generate a stimulus control signal 242 for causing the neural stimulator 202 to deliver a neural stimulus 210 continuously during a stimulation period or intermittently during a stimulation period. In an aspect, stimulator control circuitry 240 is configured to generate a stimulus control signal 242 for causing the neural stimulator 202 to deliver a pulsed neural stimulus, and/or a neural stimulus having a time-varying amplitude, time-varying frequency, or time-varying envelope. In an aspect, the neural stimulus has waveform, frequency, amplitude selected to activate particular neural structures to produce a learning enhancing or learning blocking effect, for example as described in B. Fritsch, J. Reis, Keri Martinowich, H. M. Schambra, Y. Ji, L. G. Cohen and B. Lu, "Direct Current Stimulation Promotes BDNF-Dependent Synaptic Plasticity: Potential Implications for Motor Learning," Neuron 66, pp. 198-204, Apr. 29, 2010; Elsevier Inc.; DOI 10.1016/j.neuron.2010.03.035; Y.-H. Kim, J.-W. Park, M.-H. Ko, S. H. Jang, and P. K. W. Lee, "Facilitative effect of high frequency subthreshold repetitive transcranial magnetic stimulation on complex sequential motor learning in humans," (Abstract) Neuroscience Letters, Volume 367, Issue 2, 2 September 2004, Pages 181-185; Elsevier Ireland Ltd., http://dx.doi.org/10.1016/j.neulet.2004.05.113; B. Guse, P. Falkai, and T. Wobrock, "Cognitive effects of high-frequency repetitive transcranial magnetic stimulation:

a systematic review," J Neural Transm (2010) 117:105-122, DOI 10.1007/s00702-009-0333-7; and D. Terney, L. Chaieg, V. Moliadze, A. Antal, and W. Paulus, "Increasing Human Brain Excitability by Transcranial High-Frequency Random Noise Stimulation," The Journal of Neuroscience, Dec. 24, 2008·28(52):14147-14155, DOI:10.1523/JNEURO-SCI.4248-08.2008; all of which are incorporated herein by reference. The neural stimulus may be delivered according to programmed pattern. In various aspects, stimulator control circuitry 240 is used to determine a neural stimulus amplitude, frequency, waveform, pattern, or duration. System 200 includes data storage location 244, which in various aspects contains stored preprogrammed stimulus patterns and waveforms as well as stimulus parameter values from which neural stimuli can be computed. In some aspects, stimulator control circuitry 240 modifies stimulus control signal 242 responsive to the subject's task performance, as discussed in greater detail below.

In an aspect, stimulator control circuitry 240 modulates stimulus control signal 242 in response to an override signal. For example, in an aspect override signal is received via a user input of personal computing device 250. In an aspect, override signal is received from sensing system 206. For example, the override signal can be any sensed signal indicative of an unsafe condition. In an aspect, the override signal originates from a sensor that senses a physiological parameter, such as heart rate. In the event that the physiological parameter indicates an unsafe condition (e.g., the heart rate is too high or too low), stimulator control circuitry 240 modulates stimulus control signal 242 to discontinue production of the neural stimulus. In various aspects, the override signal indicates improper positioning or poor connectivity of a stimulation electrode, a system malfunction, or other circumstances in which continued neural stimulation is either ineffective or unsafe. In addition to modulating or discontinuing the neural stimulus in response to an override condition (e.g., physiological parameter indicative of an unsafe condition, improper positioning, a notification may be sent to the subject and/or to another party regarding the override condition, to prompt the recipient of the notification to take corrective action, or for inclusion of the information in the subject's medical records, for example.

Timing control circuitry 256 is adapted to control the timing of delivery of the neural stimulus 210 with respect to the at least one prompt 216. In an aspect, timing control circuitry 256 is adapted to control the timing of delivery of the neural stimulus 210 with respect to the at least one prompt 216 to cause delivery of the neural stimulus 210 prior to delivery of the at least one prompt 216. In another aspect, timing control circuitry 256 is adapted to control the timing of delivery of the neural stimulus 210 with respect to the at least one prompt 216 to cause delivery of the neural stimulus 210 subsequent to delivery of the at least one prompt 216. In another aspect, timing control circuitry 256 is configured to control the timing of delivery of the neural stimulus 210 with respect to the at least one prompt 216 to cause delivery of the transcutaneous neural stimulus 210 to overlap at least partially with delivery of the at least one prompt 216.

In an aspect, timing control circuitry 256 is configured to control the number of repetitions of the specific activity that the subject is prompted to perform by generating one prompt 216 for each of the number of repetitions. In another aspect, timing control circuitry 256 is configured to control the number of repetitions of the specific activity that the subject is prompted to perform by generating a first prompt 216 that informs the subject of the number of repetitions and a second prompt 258 that is repeated once for each of the number of repetitions. In another aspect, timing control circuitry 256 is configured to control the number of repetitions of the specific activity that the subject is prompted to perform by generating a first prompt 216 that informs the subject of the specific activity that is to be performed and a second prompt 258 that is repeated once for each of the number of repetitions. In an aspect, timing control circuitry 256 is configured to control the number of repetitions of the specific activity that the subject is prompted to perform by generating a prompt (216 or 258) at a fixed rate for a fixed period of time.

In various aspects, prompting system 204 is adapted to deliver an audio-visual prompt, a tactile prompt, a haptic prompt, or an electrical stimulus (which can produce various sensory effects, depending upon where the stimulus is applied). Prompting system 204 may include, for example, a visible signal source 260 adapted to deliver a visible prompt, e.g. a display 262 or light 264. In other aspects, prompting system 204 includes a sound source 266, for example a speaker 268. In an aspect, prompting system 204 includes at least one electrical stimulator 270, mechanical stimulator 272 (e.g. a vibrator 274 or force-applying element 276), or olfactory stimulus source 278. In other aspects, prompting system 204 includes an ultrasonic stimulator 280 or various other stimulators adapted to produce sensory or other consciously detectable effects in the subject, e.g., a thermal stimulator 279 or electromagnetic stimulator 281. In an aspect, prompting system includes two or more of a display 262, light 264, speaker 268, vibrator 274, force-applying element 276, mechanical stimulator 272, electrical stimulator 270, ultrasonic stimulator 280, olfactory stimulus source 278, or other sensory stimulator as described herein.

In an aspect, prompting system 204 is located at least in part in or on the housing 238. In an aspect, prompting system 204 includes or is implemented on personal computing device 250. For example, display 262 or speaker 268 may be associated with personal computing device 250. In addition, a personal computing device such as a cell phone typically includes a vibrator 274 which may be used to provide a haptic stimulus to a subject. In an aspect, prompting system 204 is configured as a wearable item 282, for example as a garment or wristband. In an aspect, prompting system is configured for attachment to or mounting in or on an instrument, implement, article of equipment, or article of clothing, as indicated at 284.

In an aspect, system 200 includes a sensing system 206 for detecting performance of the activity by the subject. In various aspects, sensing system 206 is adapted to detect performance of a mental activity by the subject, performance of a physical activity by the subject, or performance of two or more related physical or mental activities by the subject. In other aspects, sensing system 206 includes sensors adapted for sensing parameters not directly related to the activity performed by the subject, but pertinent to control of stimulation or other aspects of operation of system 200. Sensing system 206 includes one or more sensors, including, for example, at least one of a neural sensor 290 (for example, an EEG sensor 292, an ENG sensor 294, an EOG sensor 296), an EMG sensor 298, a motion sensor 300, a pressure sensor 302, a force sensor 304, an accelerometer 306, an inclinometer 307, a camera 308, a Kinect 310, a scanner 312, an optical sensor 314, a microphone 316, a temperature sensor 318, physiological sensor 320, a location sensor 322, any eye tracking sensor 324, an attention sensor 326, or an environmental sensor 328. In various aspects, sensing system 206 includes one or more of an implantable sensor 330, a wearable sensor 332, a sensor carried by the subject (334), a sensor in or on an instrument, implement, or article of equipment carried by the subject (336), or a remote sensor (338). In some aspects, a neural sensor 290 is housed with neural stimulator 202. In other aspects, a neural sensor 290 is housed separately from neural stimulator 202, but may be operatively connected to the neural stimulator 202 and/or other system components via a wireless connection.

In an aspect, sensing system 206 includes one or more attention sensor 326 that can be used to detect parameters indicative of attentiveness of the subject. Such sensors include, for example, eye tracking sensors 324 (including image processing based sensors, including imagers, laser scanners, 3D scanners; or EOG based sensors), EEG sensors 292 for detecting electrical correlates of attention, various types of sensors adapted to detect physical activity of the subject that correlates to attention, including but not limited to an EMG sensor 298, a motion sensor 300, a pressure sensor 302, a force sensor 304, an accelerometer 306, or an inclinometer 307. In some aspects, inattention of the subject may be indicated by a decline in performance, inconsistent movement, etc. Attention tracking sensors can include wearable sensors, or remote sensors. In various aspects, sensing system 206 includes one or more sensor for detecting parameters that correlate directly with the activity being learned. In other aspects, sensing system 206 includes one or more sensors that provide information from which the activity can be inferred. In some aspects, sensing system 206 includes sensors for detecting parameters used for controlling delivery of neural stimulation can be sensed, for example, with physiological sensors, environmental sensors, locations sensors, and attention sensors, which relate to the general condition of the subject or the environment relative to learning in general, but are not specific to the particular activity being learned.

Electroencephalographic (EEG) signal sensor 292 can be configured to fit within an ear canal of a subject, e.g., on an ear canal insert (for example as described in U.S. Patent Publication 2003/0195588 to Fischell et al., or U.S. Patent Publication 2006/0094974 to Cain, both of which are incorporated herein by reference). Physiological sensor 320 can include, for example, an electromyographic (EMG) sensor 298, a heart rate sensor (which may be used to heart rhythm variability, as well as heart rate, and may include, but is not limited to, and EKG or pulse-oximeter based heart rate sensor), an oxygenation sensor, blood pressure sensor, perspiration sensor, skin conductivity sensor, respiration sensor, pupil dilation sensor, digestive tract activity sensor, or piloerection sensor. In another aspect, environmental sensor 328 includes a light sensor, which may be configured to sense light level and or day length. Environmental sensor 328 may include a temperature sensor 318, or an acoustic sensor (not shown), e.g., configured to sense ambient noise level. Other types of sensors for providing information regarding the state of the subject and his or her environment may be used, without limitation, including motion sensor 300 or location sensor 322, for example. A variety of physiological and environmental sensors are described in U.S. Pat. No. 8,204,786 to LeBoueuf et al., which is incorporated herein by reference. Digestive tract activity may be sensed with external acoustical sensors, for example as described in "New disposable biosensor may help physicians determine which patients can safely be fed following surgery," MedicalXpress, Aug. 7, 2014, which is incorporated herein by reference.

Figure 3:
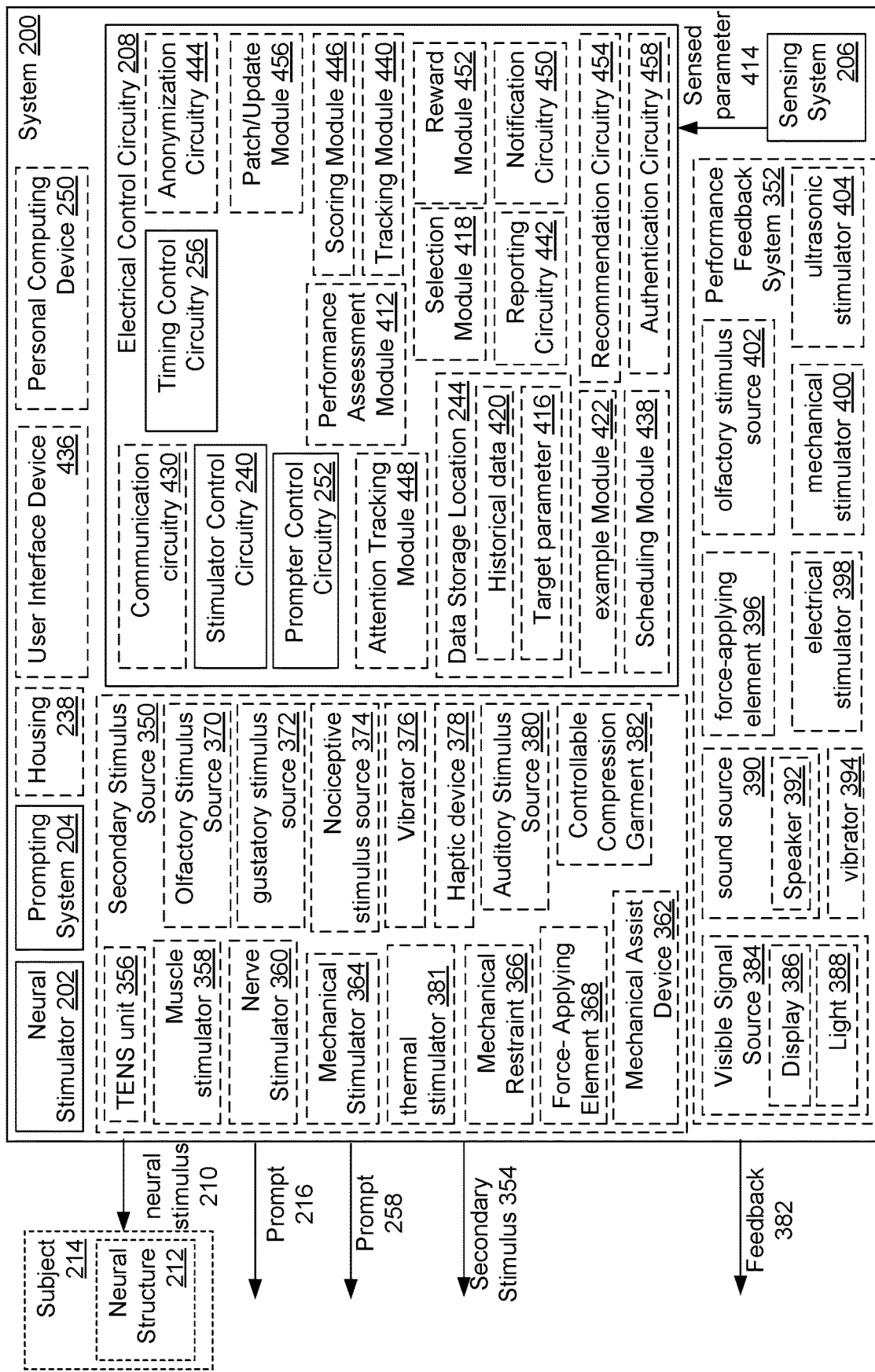
FIG. 3 is a block diagram showing further details of the system of FIG. 2.

FIG. 3 depicts further aspects of system 200. Neural stimulator 202, prompting system 204, sensing system 206, electrical control circuitry 208, stimulator control circuitry 240, prompter control circuitry 252, and timing control circuitry 256, are as described in connection with FIG. 2, as are any other components of FIG. 3 having the same reference numbers as components of FIG. 3.

FIG. 3 provides detail regarding additional aspects of electrical control circuitry 208. FIG. 3 also illustrates secondary stimulus source 350 and performance feedback system 352, which are used in some embodiments.

Secondary stimulus source 350 is used to deliver a secondary stimulus 354 to subject 214. In an aspect, secondary stimulus 354 assists subject 214 in performing the task to be learned and/or enhances learning of the task. Secondary stimulus source 350 may be, for example, a TENS unit 356, a muscle stimulator 358, a nerve stimulator 360, a mechanical assist device 362, a mechanical stimulator 364, a mechanical restraint 366, a force applying element 368, an olfactory stimulus source 370, a gustatory stimulus source 372, a nociceptive stimulus source 374, a vibrator 376, haptic device 378, an auditory stimulus source 380, or a thermal stimulator 381. In an aspect, secondary stimulus source 350 includes a controllable compression garment 382. For example, in an aspect, a secondary stimulus source 350 (e.g. mechanical assist device 362) assists subject 214 in performing a motor task. In another aspect, a secondary stimulus source 350 (e.g., mechanical restraint 366 or force applying element 368) provides resistance to movement as a subject performs a motor task, either to prevent incorrect movement or to necessitate greater application of force as the subject performs a desired movement. In another aspect, a secondary stimulus source 350 (e.g., mechanical stimulator 364, nociceptive stimulus source 374, or vibrator 376) delivers a stimulus to a portion of the subject's body to remind the subject to control movement of the specific portion of the body. In an aspect, a secondary stimulus source 350 (e.g. an olfactory stimulus source 370, a gustatory stimulus source 372, an auditory stimulus source 380) provides a secondary stimulus 354 that promotes multi-sensory learning. In an aspect, secondary stimulus source 350 includes a component of prompting system 204 and/or performance feedback system 352, which is described herein below. In another aspect, at least one secondary stimulus source 350 is different from and/or distinct from components of prompting system 204 and performance feedback system 352. Secondary stimulus source 350 is controlled by stimulator control circuitry 240, with timing of delivery of secondary stimulus 354 controlled by timing control circuitry 256.

A noted above, in an aspect, system 200 includes performance feedback system 352, which is configured to provide feedback 382 to subject 214 regarding performance of an activity by the subject. For example, in various aspects, feedback delivered with performance feedback system 352 may inform subject 214 that a desired performance has been obtained, or inform subject 214 of the need to modify or improve performance. For example, in various aspects, performance feedback system 352 includes at least one visible signal source 384, e.g. a display 386, or light 388, a sound source 390, e.g. a speaker 392, a vibrator 394, force applying element 396, electrical stimulator 398, a mechanical stimulator 400, or olfactory stimulus source 402. In other aspects, performance feedback system 352 includes an ultrasonic stimulator 404. In some aspects, the components (display, sound source, stimulators, etc.) used to deliver performance feedback to the subject may be the same components used by prompting system 204. Alternatively, some or all of the components used to deliver performance feedback to the subject may be different from and/or distinct from those used to prompt the subject. Any of the devices disclosed as being suitable for use a secondary stimulus source 350, performance feedback system 352, or prompting system 204 can be used in any of the other of these systems, and the specific examples listed for each of these systems are not intended to be limiting.

Performance feedback system 352 provides feedback 382 under control of performance assessment module 412

Stimulator control circuitry 240 is configured to control delivery of neural stimulus 210 to the subject is based at least in part on a performance rating generated by performance assessment module 412, for example, by delivering a stimulus 210 when a relatively higher performance rating is obtained to reinforce learning of proper technique and not delivering a stimulus (or, alternatively, delivering a learning blocking stimulus) when a poor performance rating is obtained. As described in greater detail herein below in connection with several examples, various parameters may be measured to assess performance of different types of tasks.

Electrical control circuitry 208 includes performance assessment module 412 which is configured to evaluate performance of the activity by subject 214. Performance assessment module 412 is configured to compare at least one sensed parameter 414 indicative a task performance (detected by sensing system 206) with at least one target parameter 416 corresponding to a target performance of the motor task. Stimulator control circuitry 240 is configured to drive delivery of neural stimulus 210 responsive to an output of the performance assessment module 412 based at least in part on a comparison of the at least one sensed parameter 414 with the at least one target parameter 416. For example, in an aspect the at least one target parameter 416 corresponds to a preferred task performance. As noted above, in some aspects sensing system 206 is adapted to sense a plurality of parameters indicative of performance of task by the subject; performance assessment module 412 may then be configured to compare the plurality of parameters with a plurality of target parameters, and stimulator control circuitry 240 configured to drive delivery of the neural stimulus responsive to an output of the performance assessment module 412 based at least in part on a comparison of the plurality of parameters with the plurality of target parameters.

In an aspect, system 200 includes a selection module 418 adapted to compare parameters corresponding to two or more historical performances of the task by the subject (historical data 420) and select at least one parameter corresponding to at least one best performance of the two or more historical performances, wherein the preferred task performance is the at least one best performance. In an aspect, performance assessment module 412 is configured to compare the at least one parameter 414 with at least one historical parameter corresponding to at least one historical performance of the task by the subject. In another aspect, selection module 418 is adapted to compare two or more portions of two or more historical performances of the task by the subject, select the best two or more portions of the two or more historical performances, and combine the best two or more portions to produce a best combined historical performance.

In an aspect, electrical control circuitry 208 includes example module 422, which is used to control delivery of an example of a task to subject 214. The example may be provided via user interface device 436, or via various output and user interaction devices forming components of prompting system 204, secondary stimulus source 350, and/or performance feedback system 352. In an aspect, example module 422 is used for controlling delivery of an example of a sound pattern to the subject. An example of the sound pattern can be presented in graphical form, and take the form of a musical score, a script, or a text presented via display 386, for example. In another aspect, an example of a sound pattern can be presented in audio form, via one or more sound source 390, for example. For example, an example of a piece of music that subject 214 is learning could be a recording of the piece of music, played by a skilled musician. An example of a motor task can be, for example, a verbal description of the motor task, presented via sound source 390, for example, or a video of the performance of the motor task, presented via display 386. In another aspect, example module 422 controls delivery of an example of a motor task (e.g., a motor task involving the subject moving their body in a specific pattern) to subject 214 via one or more output devices that cause the subject's body to move in the specific pattern, e.g., muscle stimulator 358, nerve stimulator 360, mechanical assist device 362, mechanical stimulator 364, or mechanical restraint 366. As is described in greater detail elsewhere herein, in some cases the example is provided to subject 214 prior to delivering a prompt for prompting the subject to perform the task. In other cases the prompt is the same as the example. The example can take various forms, depending on the task being learned. Furthermore, a single task can be represented by several different types of examples (e.g., a piece of music to be learned can be represented in an audio recording or a musical score; moreover, playing a piece of music on a violin, for example, requires learning a particular set of muscle movements needed to generate the desired sound).

In an aspect, system 200 includes communication circuitry 430 for providing communication between electrical control circuitry 208 and a computing or communication network 432. In addition, communication circuitry 430 provides for communication between separately packaged components of system 200 located in the vicinity of subject 214, such that the components are operably connected. In some aspects, communication circuitry 430 provides for wired communication. Alternatively, or in addition, a wireless communication link may be provided. In various aspects, a wireless communication link includes at least one of a radio frequency, wireless network, cellular network, satellite, WiFi, BlueTooth, Wide Area Network, Local Area Network, or Body Area Network communication link. Communication between locations remote from each other may take place over telecommunications networks, for example public or private Wide Area Network (WAN). In general, communication between remote locations is not considered to be suitably handled by technologies geared towards physically localized networks, e.g., Local Area Network (LAN) technologies operation at Layer 1/2 (such as the forms of Ethernet or WiFi). However, it will be appreciated that portions (but not the entirety) of communication networks used in remote communications may include technologies suitable for use in physically localized network, such as Ethernet or WiFi.

In an aspect, system 200 includes at least one user interface device 436 for at least one of providing an output to the subject and receiving an input from the subject. In an aspect, at least one user interface device 436 includes one or more component of personal computing device 250. User interface device 436 includes one or more output device, such as an LED or other light emitting element, an alphanumeric display, a graphical display, or other screen, audio output, or tactile display, or input devices, e.g., a touchscreens, keyboard, mouse, button, dial, or voice command input. In some aspects, a user interface device 436 includes a brain computer interface.

In an aspect, system 200 includes scheduling module 438 for creating a practice session schedule, and generating reminders to remind subject 214 of one or more practice sessions from the practice session schedule. Scheduling module 438 can interface with one or more calendars stored locally or remotely, to add practice sessions to a calendar, retrieve practice session information from a calendar, and coordinate scheduling with other events on the calendar, for example.

In an aspect, system 200 includes tracking module 440 configured to track practice sessions during which the subject practices the activity and to store tracked practice session data in a data storage location, e.g. data storage location 244. For example, in an aspect, tracking module 440 is configured to track time and date of practice sessions. In an aspect, tracking module 440 is configured to track duration of practice sessions. In an additional aspect, tracking module 440 is configured to generate practice session trends or metrics based on one or more tracked practice sessions.

In an aspect, system 200 includes reporting circuitry 442 for reporting information regarding one or more tracked practice sessions, practice session trends, or practice session metrics. For example, reporting circuitry can be used to provide a report to one or more of the subject, a parent, an instructor, a coach, a medical care provider, or a peer. In some aspects, a report is provided to other parties, for example, an insurance company or a service provider (e.g., a business or other entity that provides services related to system 200 or related to monitoring use of system 200). In an aspect, a report is provided to at least one social media contact (or 'friend'), e.g., via a social network. In an aspect, reporting circuitry 442 causes a report to be provided via user interface device 436 or via network 432 (accessed via communication circuitry 430), e.g. to a computing system used for storing and/or processing healthcare or other information (e.g., including a computing device, memory, network, record, or file). In various aspects, anonymization circuitry 444 is used to provide the report in anonymized form (e.g., with information identifying the subject removed therefrom). Reports provided by reporting circuitry 442 may include various types of information, including but not limited to information regarding device and system settings, stimuli delivered (including neural stimulus and secondary stimulus) as well as practice sessions, practice session trends, or practice session metrics. Reporting and tracking functions may be generally as described in U.S. Published Patent Application No. 2016/0279435 to Hyde et al., which is incorporated herein by reference.

In an aspect, reporting circuitry 442 provides reports based on one or more tracked practice sessions to a scoring module 446. For example, in an aspect, scoring module 446 assigns a score or ranking to subject 214 based on the performance of the subject during the one or more tracked practice sessions. In an aspect, scoring module 446 assigns a score or ranking to subject 214 based on the subject's performance relative to the performance of one or more other individuals.

In some aspects, the subject's attentiveness, e.g., to the task being performed, is assessed by attention tracking module 448, which it receives as an input indicative of attentiveness of subject 214 from sensing system 206 (e.g., from attention sensor 326 depicted in and described in connection with FIG. 2). Attention tracking module 448 is operatively connected to attention sensor 326, and determines whether the subject is attentive based on at least one parameter sensed by attention sensor 326. If it is determined with attention tracking module 448 that subject 214 is not attentive, then a notification may be generated with notification circuitry 450. For example, in various aspects, notification circuitry 450 provides for delivery of an audio alarm tone, a verbal notification, a visible notification, a tactile notification, an electronic notification stored in a data storage location (e.g., data storage location 244) or an electronic notification transmitted to at least one additional location, e.g. via network 432. In various aspects, notification circuitry 450 provides for delivery of a notification via user interface device 436, one or more components of prompting system 204 or performance feedback system 352, or other user interface or output devices. The user interface or output device used in combination with notification circuitry 450 forms a notification system. In various aspects, the notification system is used to provide system diagnostic information, instructions, notification of fault or alarm conditions, etc. In an aspect, notification circuitry 450 includes circuitry for delivering a voice message (e.g., a preset message retrieved from data storage location 244). In a further aspect, notification circuitry 450 includes circuitry for storing information in a data storage location 244.

In an aspect, system 200 includes reward module 452 for transferring a reward to the subject account based upon one or more tracked practice session. In an aspect, reward module 452 is adapted to deliver a reward to the subject, e.g. via user interface or output devices. In an aspect, reward module 452 is adapted to provide positive feedback to the subject via a user interface (for example, a verbal notification stating "Terrific! Keep up the good work!" or the like). In an aspect, reward module 452 is adapted to deliver the reward to the subject based upon at least one of attentiveness of the subject, as determined by attention tracking module 448; performance of the subject, as determined by performance assessment module 412; and system usage by the subject, as determined by tracking module 440. In another aspect, reward module 452 is adapted to credit reward points to an account associated with the subject. For example, reward points may be redeemable for money, a physical reward item, game play, status points, etc. The user account may information may be stored locally (e.g., in data storage location 244), or remotely, (e.g. at a location in network 432). In an aspect reward module 452 provides a competitive and/or gameplay element that allows subject 214 to compete with their own previous performances, or with the performances of others. In an aspect, reward module 452 credits reward or status points for use in one or more other games not directly related to the learning system described herein.

In an aspect, system 200 includes recommendation circuitry 454 for presenting a recommendation to the subject. The recommendation may be presented to the subject via user interface device 436 or via other output devices forming components of prompting system 204 and/or performance feedback system 352, for example. In an aspect, system 200 receives the recommendation via a computing network, for example, from a medical care provider, from an insurance company, a service provider, an advisor, a computation-based system (including, e.g., an artificial intelligence), or a social media source, for example. In various aspects, recommendation circuitry 454 is configured to recognize a source of a recommendation and respond differently depending upon the source of the recommendation. Recommendations from more credible sources may be presented to the subject more promptly or more prominently, whereas recommendations from undesirable sources may be blocked, for example. A recommendation may relate to a configuration of neural stimulus or secondary stimulus. In other aspects, a recommendation relates to one or more of a consumer product, a service, a user experience, a user activity, or an organization that may be of interest to the subject, e.g., because the recommendations would enhance or be compatible with the effects of the neural stimulation received by the subject, or in some other manner relate to training provided via system 200. In an aspect, subject 214 can enter acceptance or rejection of a recommendation via user interface device 436.

In an aspect, system 200 includes patch/update module 456 for receiving a patch/update at system 200. For example, in an aspect, the patch/update includes a software patch or update for software residing on personal computing device 250 and/or electrical control circuitry 208 and may be received, for example, from the manufacturer of one or more component of system 200, from a service provider, or the like. In an aspect, patch/update module 456 is configured to update the configuration of at least one of the neural stimulator 202 and/or electrical control circuitry 208 based on historical data 420 (e.g., as stored in data storage location 244). In another aspect, patch/update module 456 is configured to update the configuration based on and instruction received via user interface device, or via network 432.

In another aspect, patch/update module 456 is configured to update the configuration of at least one of neural stimulator 202 and/or electrical control circuitry 208 based on at least one recommendation received by recommendation circuitry 454. In an aspect, input is received from subject 214 by user interface device 436 regarding acceptance or rejection of the recommendation, and patch/update module 456 updates the configuration responsive to acceptance of the recommendation by the subject (if the recommendation is rejected, no update is made in response to the recommendation). In another aspect, patch/update module 456 is configured to update the configuration of at least one of the neural stimulation device and the personal computing device based on an environmental parameter (e.g., sensed by an environmental sensor 328 in sensing system 206, as shown in FIG. 2). In another aspect, patch/update module 456 is configured to update the configuration of at least one of the neural stimulator and/or electrical control circuitry automatically. For example, in an aspect, the configuration is updated automatically according to a schedule.

In an aspect, communication circuitry 430 is configured to receive information via a secure connection. The secure connection may be provided through the use of an encrypted signal, for example. In an aspect, system 200 includes authentication circuitry 458 for receiving a credential showing that subject 214 is an authorized user. In an aspect, system 200 can be operated only following receipt of the credential. In various aspects, authentication circuitry 458 receives a password, a personal identification number, a biometric feature, or a card authentication, for example.

Figure 4:
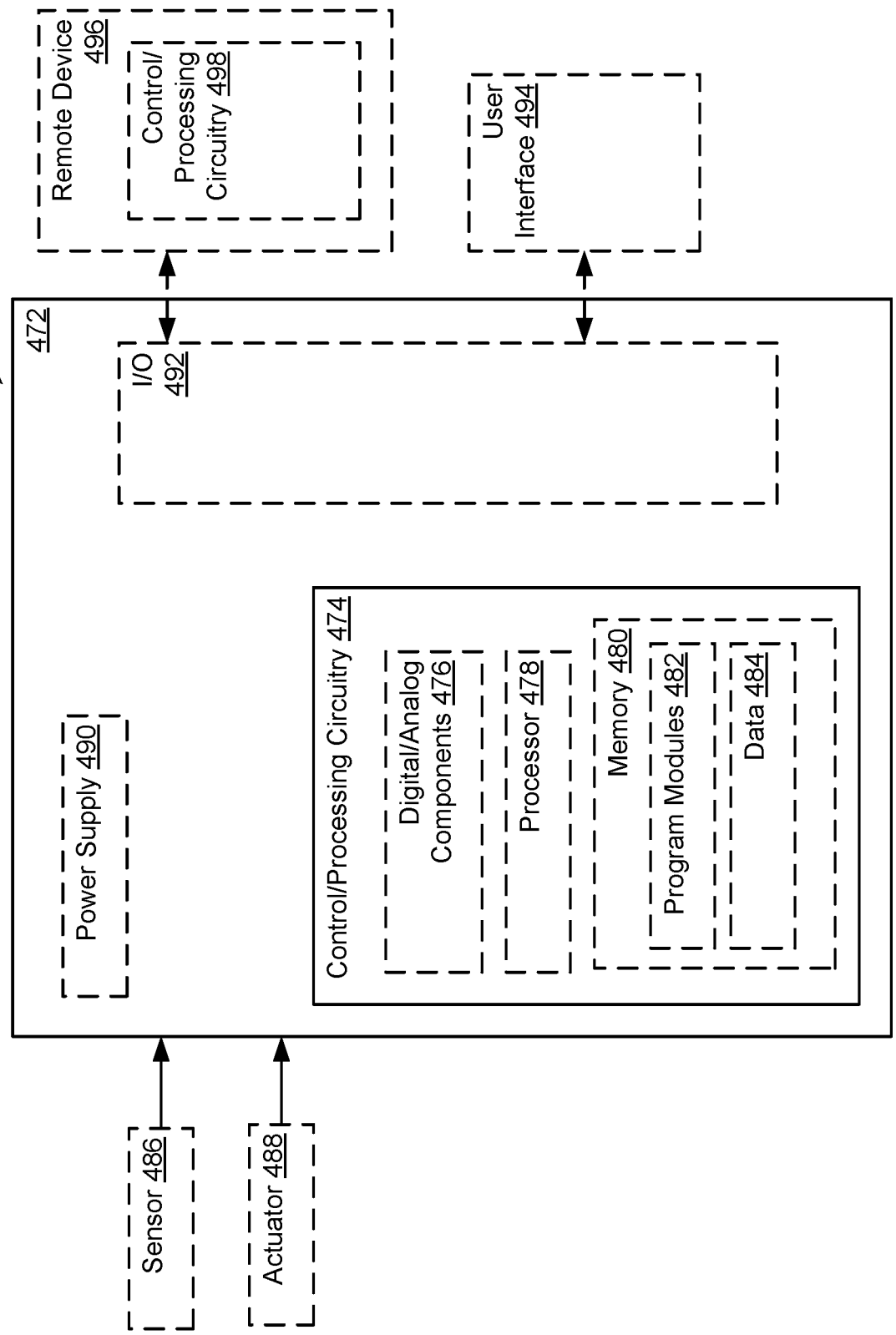
FIG. 4 is a block diagram of a circuitry-based system.

FIG. 4 illustrates a generalized form of circuitry-based systems as depicted in FIGS. 2 and 3 and elsewhere herein. Although specific embodiments are described herein, those skilled in the art will appreciate that methods and systems as described herein can be implemented in various ways. Reference is made herein to various circuitry systems and subsystems (e.g., system 200 in FIGS. 2 and 3 includes electrical control circuitry 208, which may be considered to be control/processing circuitry. As shown generically in FIG. 4, a system 470 includes a circuitry-based system 472.

Circuitry-based system 472, which in some aspects is a computing device or computing subsystem, includes control/processing circuitry 474, which includes any or all of digital and/or analog components 476, one or more processor 478 (e.g., a microprocessor), and memory 480, which may store one or more program module 482 and/or data 484. In some aspects, control/processing circuitry provides for preliminary handling of data from one or more sensor 486, transfer of data to remote device 496, receipt of control signal from remote device 496, and actuation of actuator 488, which may be for example a neural stimulator (such as neural stimulator 202, prompting system 204, secondary stimulus source, and performance feedback system 352 shown in FIGS. 2 and 3). Systems as described herein may receive signals from various sensors (e.g., sensing system 206 depicted in FIGS. 2 and 3). System 470 may include other components as known to those skilled in the art, e.g., one or more power supply 490, I/O structure 492, clock, timer, data bus, etc. I/O structure 492 permits communication with various types of user interface devices (represented by user interface 494, which may include one or more input devices such as a keyboard, button, switch, computer mouse, or touchscreen or one or more output devices such as screen, sound source, alphanumeric display, Braille display, etc.) and communication with various types of remote device 496, which may have control/processing capability conferred by control/processing circuitry 498.

Figure 5:
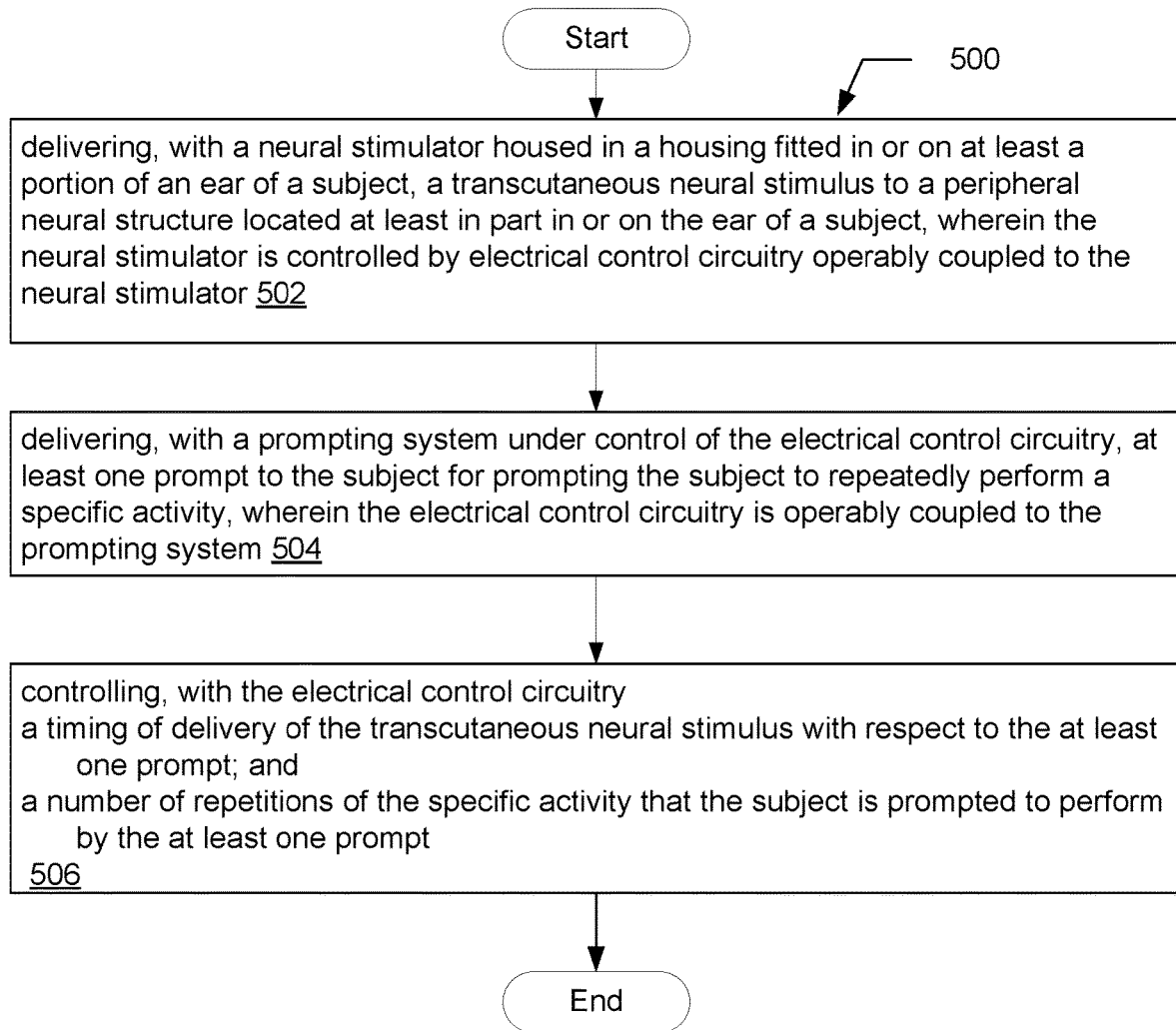
FIG. 5 is a flow diagram of a method of enhancing learning.

FIG. 5 is a flow diagram of a method 500 relating to enhancing learning through use of a system as depicted in FIG. 1. Here and elsewhere, method steps outlined with dashed lines represent steps that are included in some, but not all method aspects, and combinations of steps other than those specifically depicted in the figures are possible as would be known by those having ordinary skill in the relevant art.

Method 500 includes delivering, with a neural stimulator housed in a housing fitted in or on at least a portion of an ear of a subject, a transcutaneous neural stimulus to a peripheral neural structure located at least in part in or on the ear of a subject, wherein the neural stimulator is controlled by electrical control circuitry operably coupled to the neural stimulator, at 502; delivering, with a prompting system under control of the electrical control circuitry, at least one prompt to the subject for prompting the subject to repeatedly perform a specific activity, wherein the electrical control circuitry is operably coupled to the prompting system, at 504; controlling, with the electrical control circuitry, a timing of delivery of the transcutaneous neural stimulus with respect to the at least one prompt and a number of repetitions of the specific activity that the subject is prompted to perform by the at least one prompt, at 506.

FIGS. 6-12 depict methods including additional and alternative steps relative to the method of FIG. 5. Steps 502-506 are as described in connection with FIG. 5.

Figure 6:
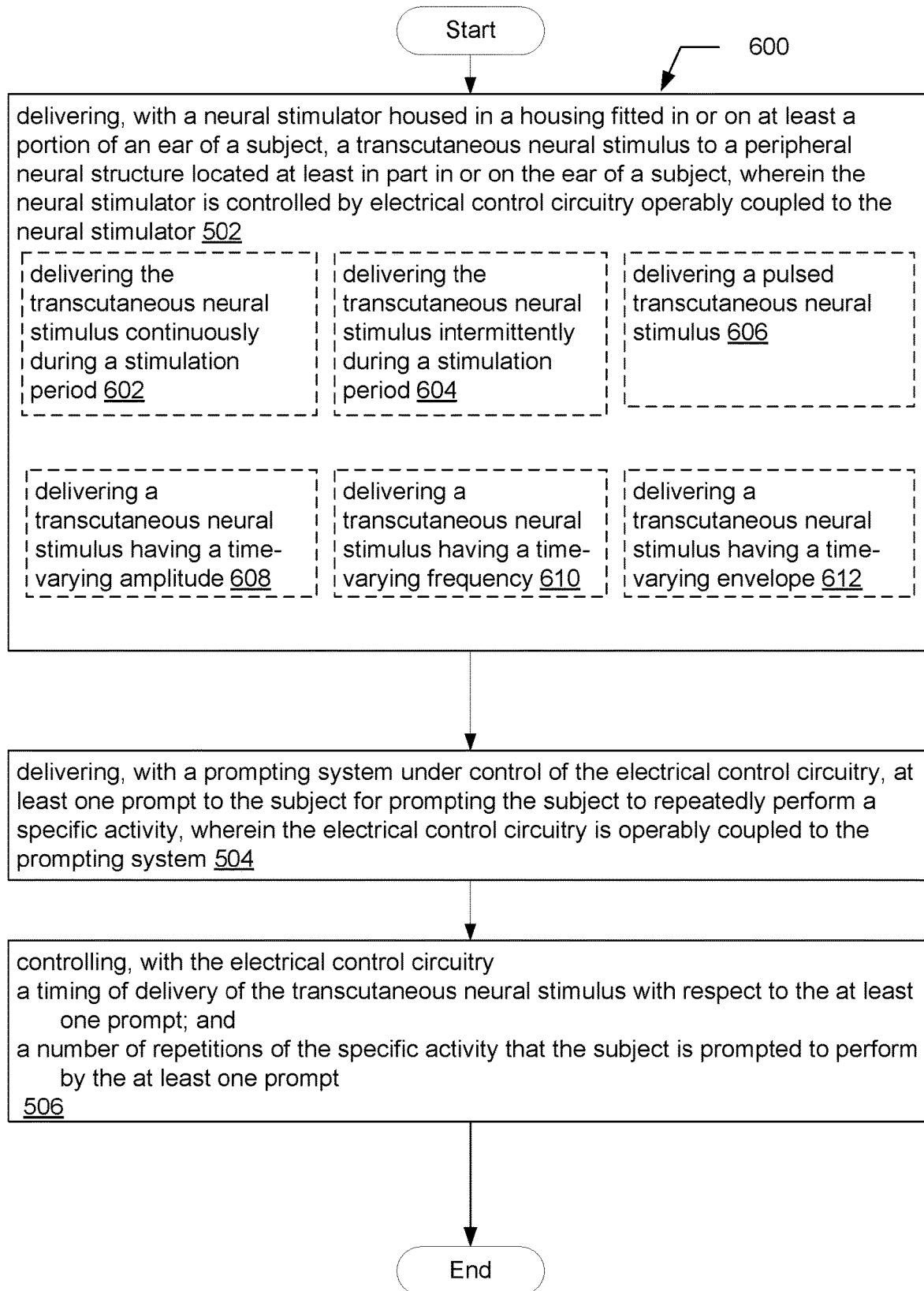
FIG. 6 is a flow diagram of a method.

FIG. 6 depicts a method 600, wherein, in various aspects delivering the transcutaneous neural stimulus includes one or more of delivering the transcutaneous neural stimulus continuously during a stimulation period, at 602; delivering the transcutaneous neural stimulus intermittently during a stimulation period, at 604; delivering a pulsed transcutaneous neural stimulus, at 606; delivering a transcutaneous neural stimulus having a time-varying amplitude, at 608; delivering a transcutaneous neural stimulus having a time-varying frequency, at 610; or delivering a transcutaneous neural stimulus having a time-varying envelope, at 612.

Figure 7:
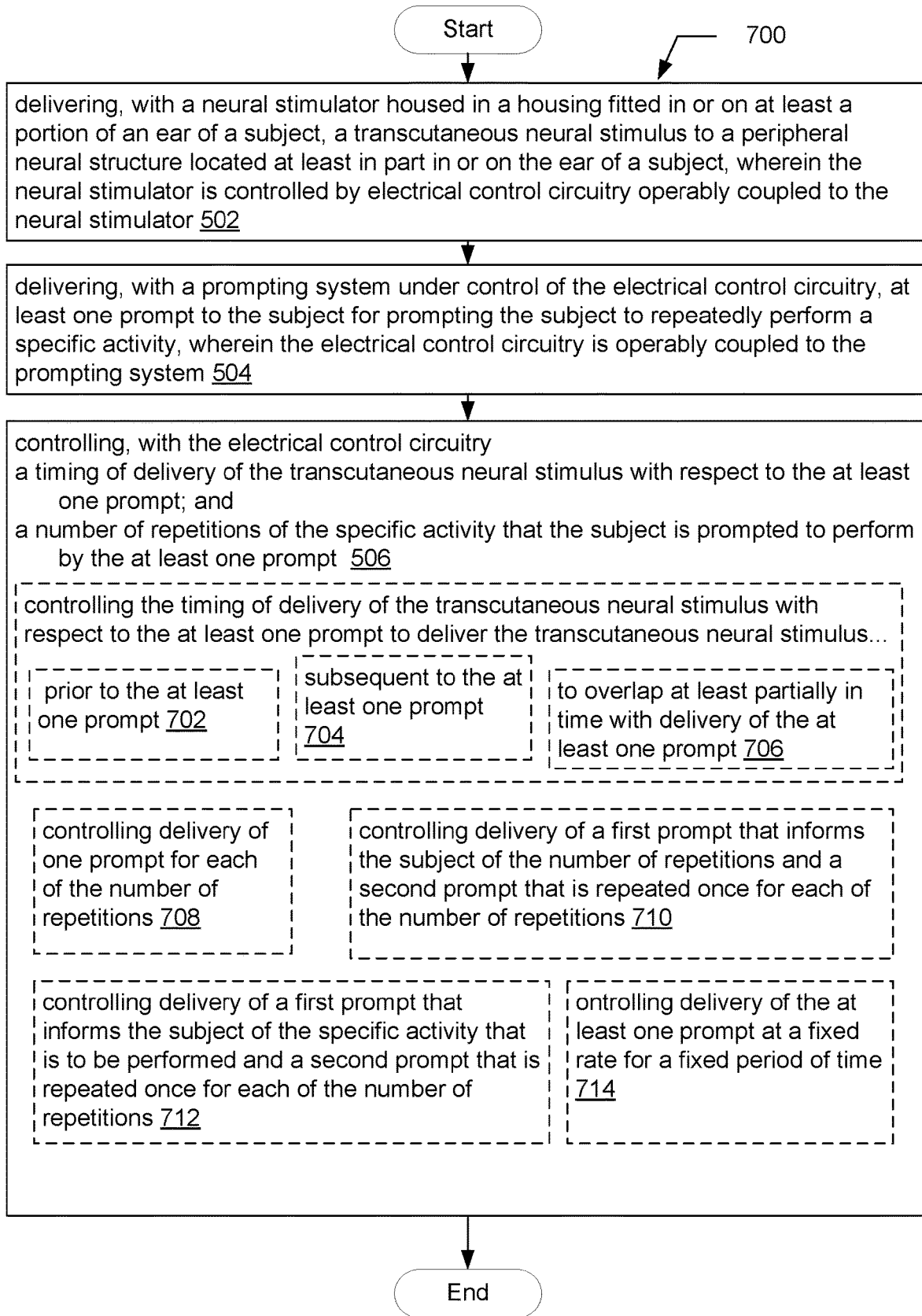
FIG. 7 is a flow diagram of a method.

FIG. 7 depicts a method 700, including controlling the timing of delivery of the transcutaneous neural stimulus with respect to the at least one prompt (as indicated at 506) to deliver the transcutaneous neural stimulus prior to the at least one prompt, at 702; subsequent to the at least one prompt, at 704; or overlapping at least partially in time with delivery of the at least one prompt, at 706. In an aspect, wherein controlling the number of repetitions of the specific activity that the subject is prompted to perform includes controlling delivery of one prompt for each of the number of repetitions, as indicated at 708.

In another aspect, controlling the number of repetitions of the specific activity that the subject is prompted to perform includes controlling delivery of a first prompt that informs the subject of the number of repetitions and a second prompt that is repeated once for each of the number of repetitions, as indicated at 710.

In yet another aspect, controlling the number of repetitions of the specific activity that the subject is prompted to perform includes controlling delivery of a first prompt that informs the subject of the specific activity that is to be performed and a second prompt that is repeated once for each of the number of repetitions, as indicated at 712. In another aspect, controlling the number of repetitions of the specific activity that the subject is prompted to perform includes controlling delivery of the at least one prompt at a fixed rate for a fixed period of time, as indicated at 714.

Figure 8:
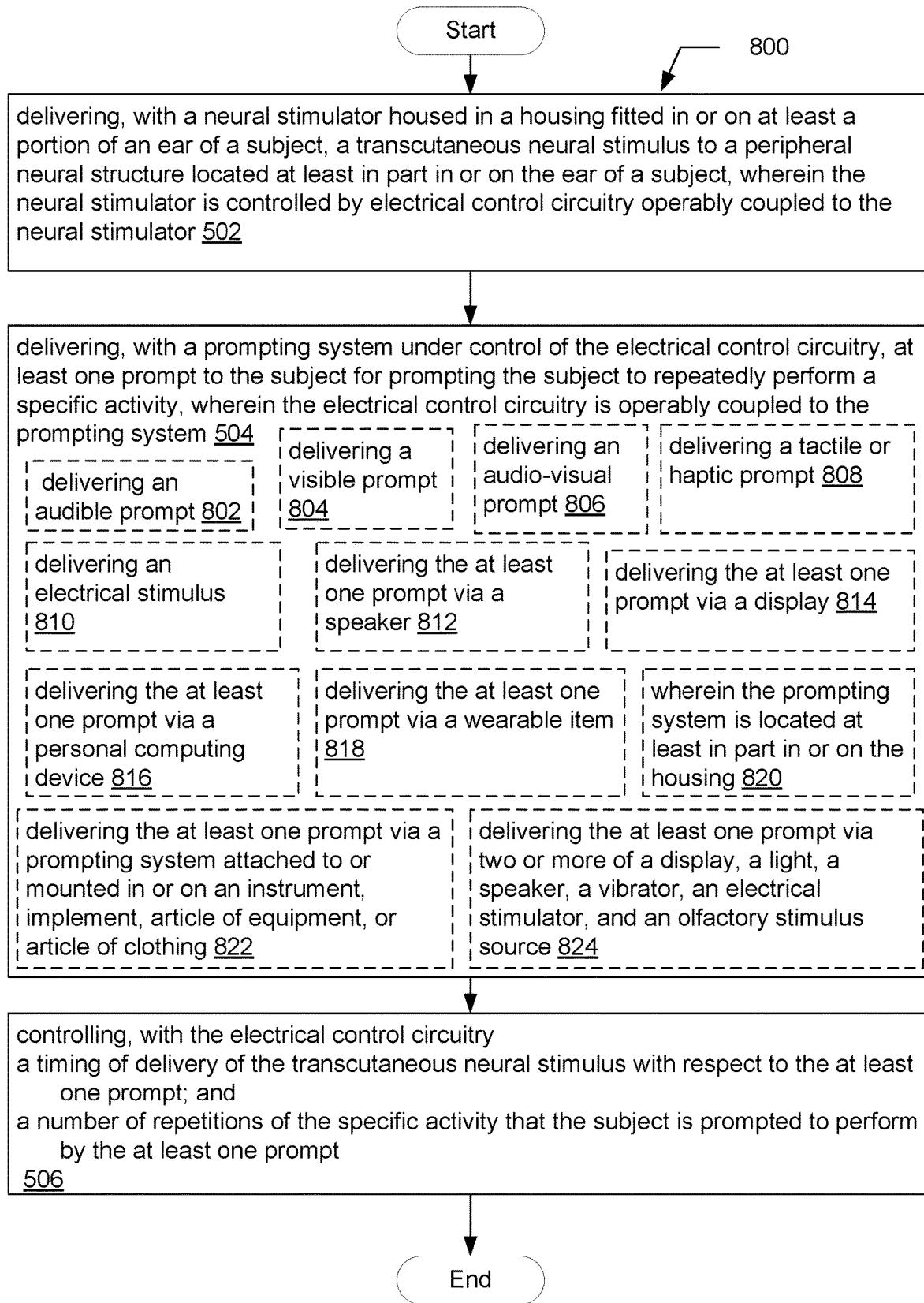
FIG. 8 is a flow diagram of a method.

FIG. 8 depicts a method 800 detailing further aspects of delivering a prompt. In various aspects, delivering the at least one prompt includes delivering an audible prompt 802; delivering a visible prompt 804; delivering an audio-visual prompt 806; delivering a tactile or haptic prompt 808; or delivering an electrical stimulus 810. In various aspects, delivering the at least one prompt includes delivering the at least one prompt via a speaker 812; a display 814; a personal computing device 816; or a wearable item 818. In some aspects, the prompting system is located at least in part in or on the housing, as indicated at 820. In other aspects, delivering the at least one prompt includes delivering the at least one prompt via a prompting system attached to or mounted in or on an instrument, implement, article of equipment, or article of clothing, as indicated at 822, or delivering the at least one prompt via two or more of a display, a light, a speaker, a vibrator, an electrical stimulator, and an olfactory stimulus source, as indicated at 824.

Figure 9:
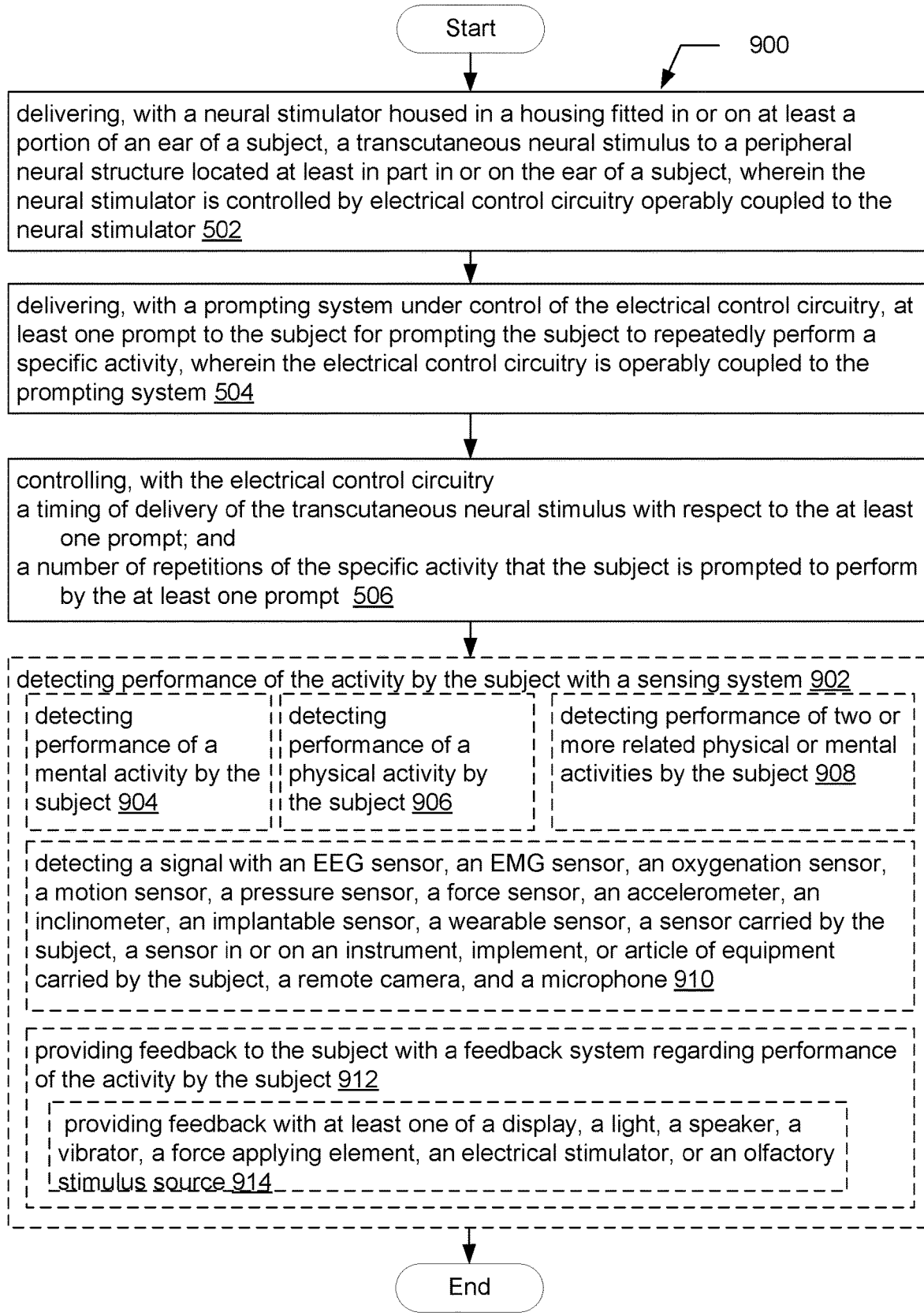
FIG. 9 is a flow diagram of a method.

FIG. 9 depicts a method 900 including steps 502-506 as depicted in FIG. 5 and also including detecting performance of the activity by the subject with a sensing system, as indicated at 902. In various aspects, detecting performance of the activity includes detecting performance of a mental activity by the subject, at 904; detecting performance of a physical activity by the subject, at 906; or detecting performance of two or more related physical or mental activities by the subject, at 908.

In various aspects, detecting performance of the activity includes detecting a signal with an EEG sensor, an EMG sensor, an oxygenation sensor, a motion sensor, a pressure sensor, a force sensor, an accelerometer, an inclinometer, an implantable sensor, a wearable sensor, a sensor carried by the subject, a sensor in or on an instrument, implement, or article of equipment carried by the subject, a remote camera, and a microphone, as indicated at 910.

Method 900 may also include providing feedback to the subject with a feedback system regarding performance of the activity by the subject, as indicated at 912. For example, in various aspects, providing feedback to the subject includes providing feedback with at least one of a display, a light, a speaker, a vibrator, a force applying element, an electrical stimulator, or an olfactory stimulus source, as indicated at 914.

Figure 10:
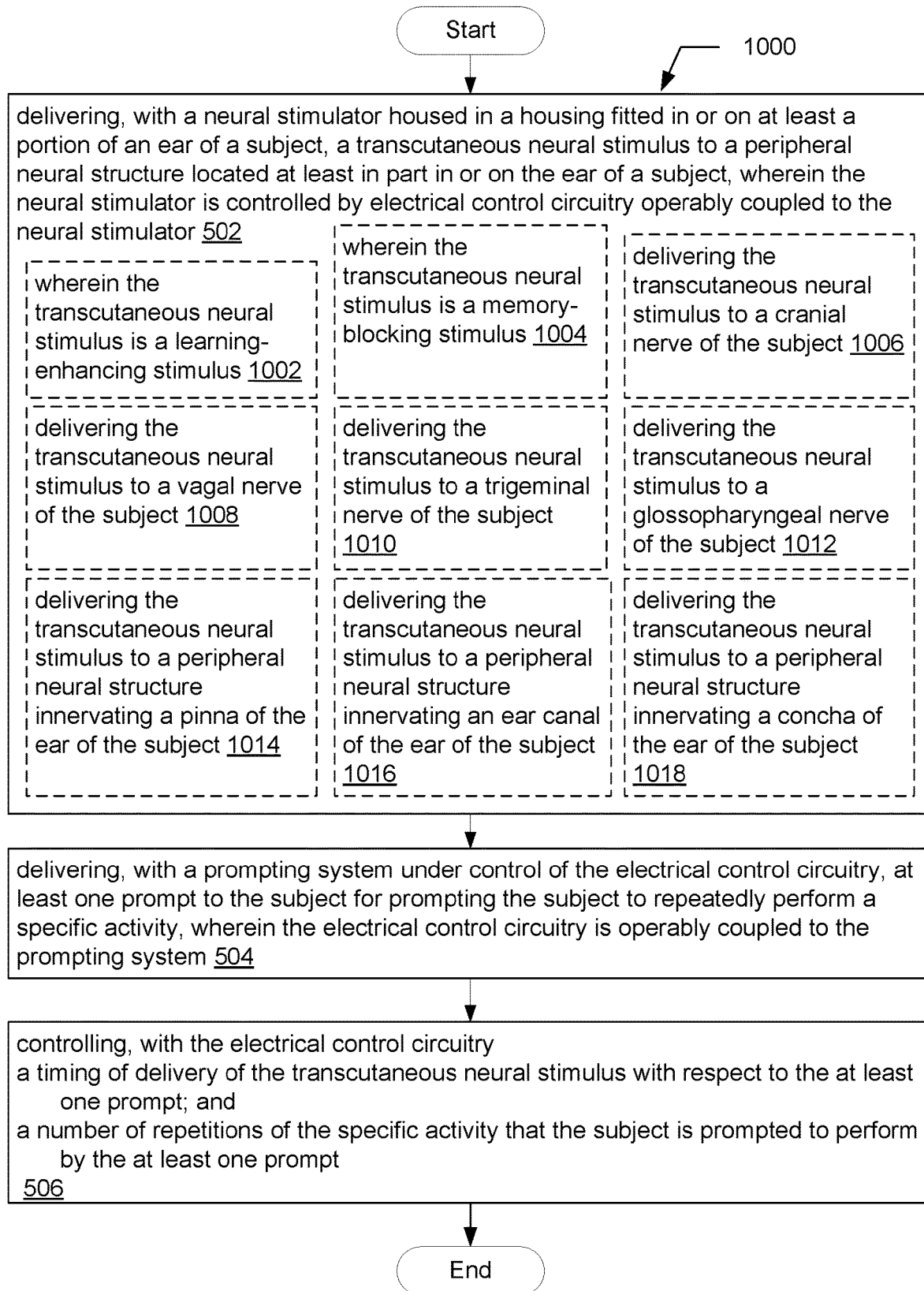
FIG. 10 is a flow diagram of a method.

FIG. 10 depicts a method 1000, including further detail regarding delivery of a transcutaneous neural stimulus. In various aspects, the transcutaneous neural stimulus is a learning-enhancing stimulus, as indicated at 1002; or a memory-blocking stimulus, as indicated at 1004. In other aspects, delivering a transcutaneous neural stimulus, as at 502, includes one or more of delivering the transcutaneous neural stimulus to a cranial nerve of the subject, as indicated at 1006; delivering the transcutaneous neural stimulus to a vagal nerve of the subject, as indicated at 1008; delivering the transcutaneous neural stimulus to a trigeminal nerve of the subject, as indicated at 1010; delivering the transcutaneous neural stimulus to a glossopharyngeal nerve of the subject, as indicated at 1012; delivering the transcutaneous neural stimulus to a peripheral neural structure innervating a pinna of the ear of the subject, as indicated at 1014; delivering the transcutaneous neural stimulus to a peripheral neural structure innervating an ear canal of the ear of the subject, as indicated at 1016; or delivering the transcutaneous neural stimulus to a peripheral neural structure innervating a concha of the ear of the subject, as indicated at 1018.

Figure 11:
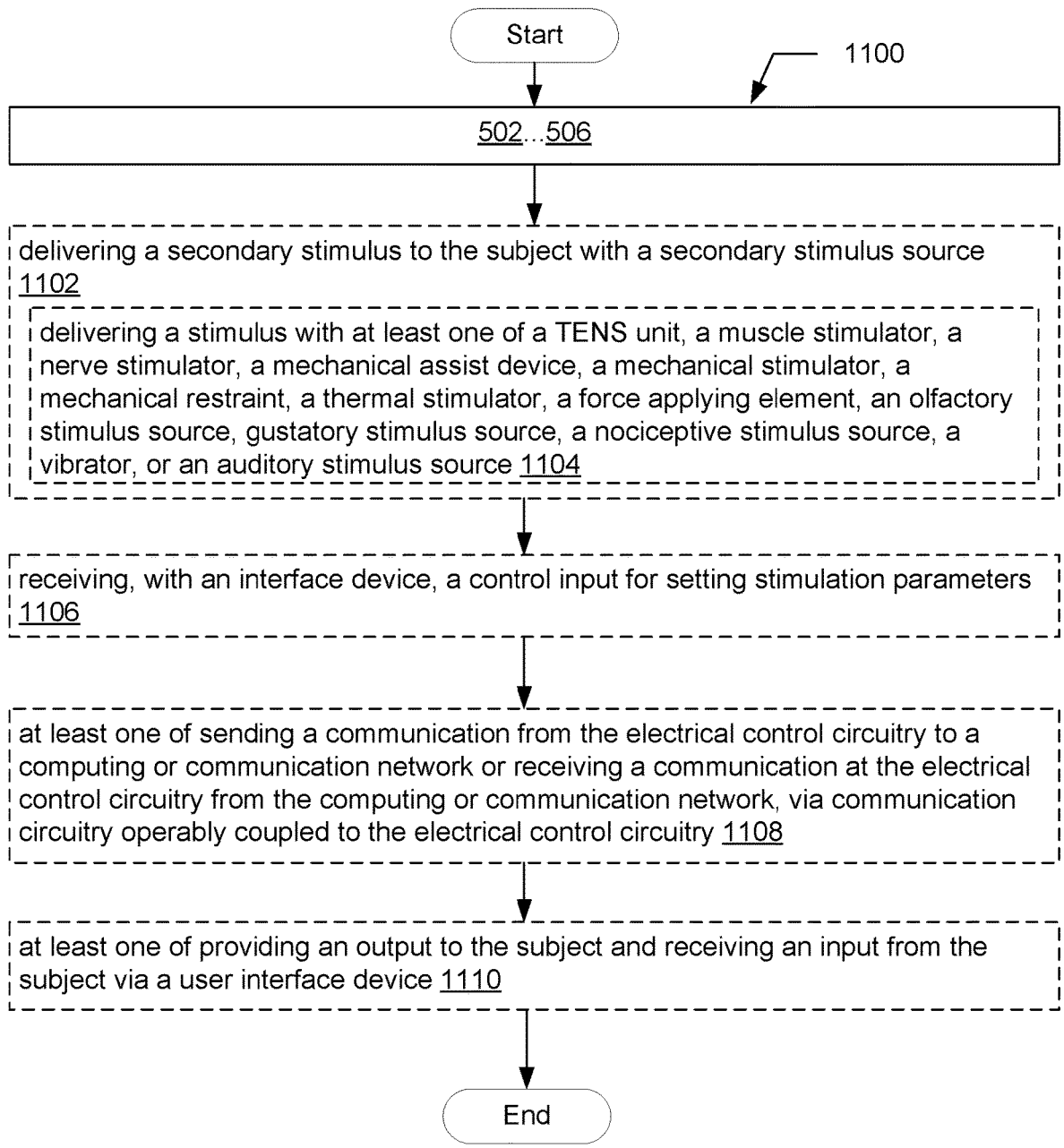
FIG. 11 is a flow diagram of a method.

FIG. 11 depicts additional method aspects. As indicated at 1102, in an aspect method 1100 includes delivering a secondary stimulus to the subject with a secondary stimulus source. For example, in various aspects, delivering the secondary stimulus to the subject includes delivering a stimulus with at least one of a TENS unit, a muscle stimulator, a nerve stimulator, a mechanical assist device, a mechanical stimulator, a mechanical restraint, a thermal stimulator, a force applying element, an olfactory stimulus source, gustatory stimulus source, a nociceptive stimulus source, a vibrator, or an auditory stimulus source, as indicated at 1104.

In another aspect, method 1100 includes receiving, with an interface device, a control input for setting stimulation parameters, as indicated at 1106. In other aspects, method 1100 includes at least one of sending a communication from the electrical control circuitry to a computing or communication network or receiving a communication at the electrical control circuitry from the computing or communication network, via communication circuitry operably coupled to the electrical control circuitry, as indicated at 1108. In yet another aspect, method 1100 includes at least one of providing an output to the subject and receiving an input from the subject via a user interface device, as indicated at 1110.

Figure 12:
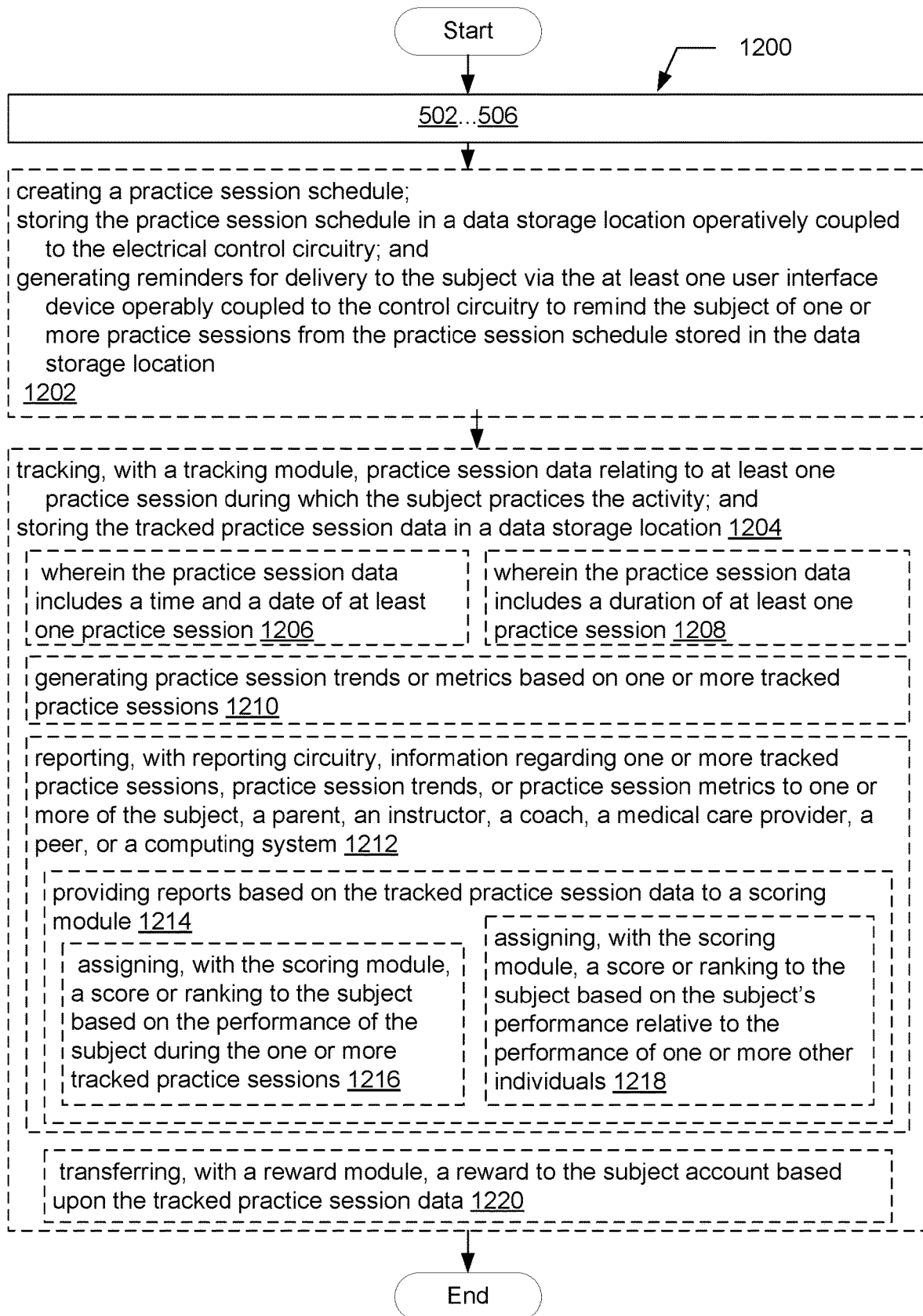
FIG. 12 is a flow diagram of a method.

FIG. 12 depicts a method 1200, including various aspects relating to practices sessions. In an aspect, method 1200 includes creating a practice session schedule, storing the practice session schedule in a data storage location operatively coupled to the electrical control circuitry, and generating reminders for delivery to the subject via the at least one user interface device operably coupled to the control circuitry to remind the subject of one or more practice sessions from the practice session schedule stored in the data storage location, as indicated at 1202.

In a further aspect, method 1200 includes tracking, with a tracking module, practice session data relating to at least one practice session during which the subject practices the activity; and storing the tracked practice session data in a data storage location, as indicated at 1204. For example, in an aspect, the practice session data includes a time and a date of at least one practice session, as indicated at 1206, or a duration of at least one practice session, as indicated at 1208.

In another aspect, method 1200 includes generating practice session trends or metrics based on one or more tracked practice sessions, as indicated at 1210.

In an aspect, method 1200 includes reporting, with reporting circuitry, information regarding one or more tracked practice sessions, practice session trends, or practice session metrics to one or more of the subject, a parent, an instructor, a coach, a medical care provider, or a peer, as indicated at 1212. For example, in a related aspect, reporting with the reporting circuitry includes providing reports based on the tracked practice session data to a scoring module, as indicated at 1214. Such a method may include assigning, with the scoring module, a score or ranking to the subject based on the performance of the subject during the one or more tracked practice sessions, as indicated at 1216 and/or assigning, with the scoring module, a score or ranking to the subject based on the subject's performance relative to the performance of one or more other individuals, as indicated at 1218. In a further aspect, method 1200 includes transferring, with a reward module, a reward to the subject account based upon the tracked practice session data, as indicated at 1220.

FIG. 13 is a block diagram of a computer program product 1300 for implementing a method as described in connection with FIG. 5. Computer program product 1300 includes at least one non-transitory computer-readable medium 1302 bearing one or more instructions for generating, under control of electrical control circuitry, at least one stimulus control signal for controlling delivery of a transcutaneous neural stimulus to a peripheral neural structure located at least in part in or on an ear of a subject via a neural stimulator fitted in or on at least a portion of the ear of a subject; one or more instructions for delivering, via a prompting system under control of the electrical control circuitry, at least one prompt for prompting the subject to repeatedly perform a specific activity; one or more instructions for controlling a timing of delivery of the transcutaneous neural stimulus with respect to the at least one prompt; and one or more instructions for controlling a number of repetitions of the specific activity that the subject is prompted to perform by the at least one prompt, as indicated at 1304. A non-transitory computer-readable medium 1302 may be, for example, a recordable medium 1306.

In addition, computer program product 1300 may include instructions for performing various aspects of method steps outlined in FIGS. 6 to 12. For example, in various aspects, non-transitory computer-readable medium 1302 bears one or more instructions for receiving, with an interface device, a control input for setting stimulation parameters; one or more instructions for sending a communication from the electrical control circuitry to a computing or communication network, via communication circuitry operably coupled to the electrical control circuitry; one or more instructions for receiving a communication at the electrical control circuitry from a computing or communication network, via communication circuitry operably coupled to the electrical control circuitry; or one or more instructions for providing an output to the subject and receiving an input from the subject via a user interface device, e.g., for implementing a method as described in FIG. 11. In other aspects, non-transitory computer-readable medium 1302 bears instructions relating to implementing methods as described in FIG. 12. For example, in an aspect non-transitory computer-readable medium 1302 bears one or more instructions for creating a practice session schedule; one or more instructions storing the practice session schedule in a data storage location operatively coupled to the electrical control circuitry; and one or more instructions for generating reminders for delivery to the subject via at least one user interface device operably coupled to the control circuitry to remind the subject of one or more practice sessions from the practice session schedule stored in the data storage location. In another aspect, non-transitory computer-readable medium 1302 bears one or more instructions for tracking, with a tracking module, practice session data relating to at least one practice session during which the subject practices the activity; and one or more instructions for storing the tracked practice session data in a data storage location. In an aspect, the one or more instructions for storing the tracked practice session data in the data storage location include one or more instructions for storing a time and a date of at least one practice session, and/or one or more instructions for storing a duration of at least one practice session.

In an aspect, non-transitory computer-readable medium 1302 bears one or more instructions for generating practice session trends or metrics based on one or more tracked practice sessions.

In an aspect, non-transitory computer-readable medium 1302 bears one or more instructions for reporting, with reporting circuitry, information regarding one or more tracked practice sessions, practice session trends, or practice session metrics to one or more of the subject, a parent, an instructor, a coach, a medical care provider, or a peer. For example, in an aspect, the one or more instructions for reporting with the reporting circuitry include one or more instructions for providing reports based on the tracked practice session data to a scoring module. In connection therewith, non-transitory computer-readable medium 1302 may bear one or more instructions for assigning, with the scoring module, a score or ranking to the subject based on the performance of the subject during the one or more tracked practice sessions, one or more instructions for assigning, with the scoring module, a score or ranking to the subject based on the subject's performance relative to the performance of one or more other individuals, or one or more instructions for transferring, with a reward module, a reward to the subject account based upon the tracked practice session data.

Figure 14:
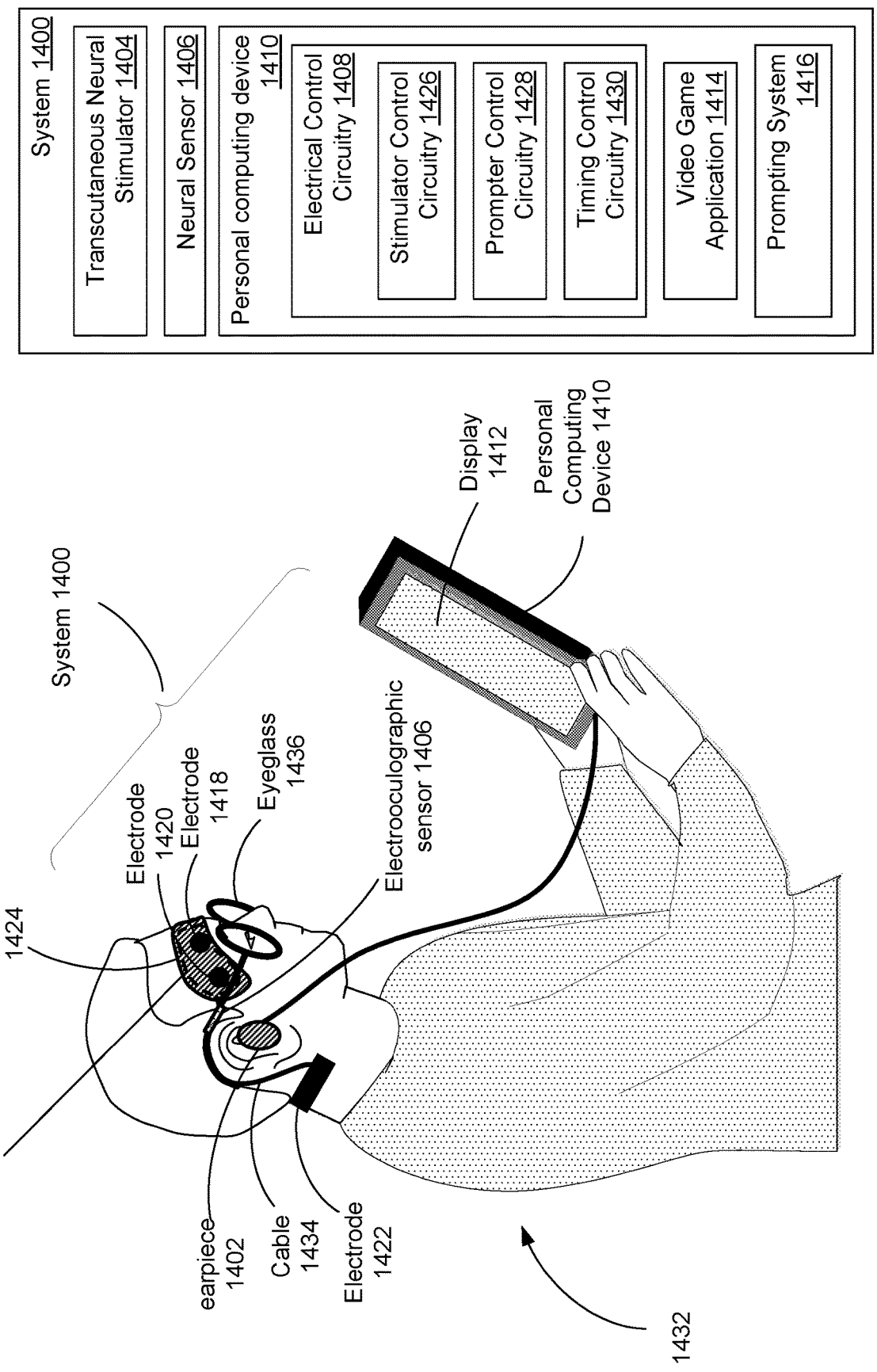
FIG. 14 depicts an embodiment of a system for enhancing learning.

FIG. 14 depicts a system 1400 for enhancing learning to rehabilitate patients with posttraumatic stress disorder.

Posttraumatic stress disorder (PTSD) arises from exposure to one or more traumatic, threatening events with a response of intense fear, helplessness, or horror. Symptoms may include: negative alterations in cognition and mood (e.g., detachment or estrangement from others, negative emotions, negative expectations), and alterations in arousal and reactivity (e.g., hyper-vigilance, exaggerated startle response, sleep disturbances). A rehabilitative enhanced learning system to modulate plasticity, alter mood, and improve cognition for PTSD patients employs cognitive training, timed neural stimulation and cognition sensing. The system includes an earpiece 1402, a transcutaneous neural stimulator 1404, an electrooculography (EOG) sensor 1406, electrical control circuitry 1408, and personal computing device 1410, with video display 1412 and video games provided by video game application 1414.

The learning system employs an earpiece 1402 connected to personal computing device 1410 (e.g., tablet computer or cell phone) to provide instructions, feedback, and prompts to the patient in conjunction with display of video games for cognitive training. Earpiece 1402 and video display 1412 form a prompting system 1416. The video games reenact or replay relevant traumatic events (e.g., combat, accidents, robberies, etc.) and prompt the patient to respond to the game with positive actions in order to accrue points and complete the game. Timed neural stimulation is applied in conjunction with playing of the video game, produced by video game application 1414 under control of electrical control circuitry 1408. For example, transdermal stimulation of the trigeminal nerve complex is accomplished with electrodes 1418, 1420, and 1422 applied to the forehead, supraorbital region (temples) and cervical region, respectively (see e.g., Boasso, et al., bioRxiv preprint available online at: http://dx.doi.org/10.1101/043901, which is incorporated herein by reference. For example, stimulation with pulse-modulated (3-11 kHz), biphasic electrical current producing average amplitudes of 5-7 mA can be administered with a device targeting the trigeminal nerve that is available from Thync Inc., Los Gatos, Calif. Cognitive training with the learning system is monitored using electrooculographic sensor 1406 to record eye movements by the patient while playing video games. For example, wearable sensors can record changes in electric potential field across the eye corresponding to movements of the eye, including saccades, blinks and fixations (see e.g., Bulling et al., *IEEE Transactions on Pattern Analysis and Machine Intelligence*, 33, 741-753, 2011 and U.S. Patent Appl. 2015/0126845 by Jin and Laszlo published on May 7, 2015 which are incorporated herein by reference). EOG recordings during visual task performance can provide information about an individual's attention, saliency, anxiety, effort and fatigue (see e.g., Bulling et al., Ibid. and Song et al., *International Journal Advanced Computer Science and Applications*, 6, 138-142, 2015 which are incorporated herein by reference).

Electrical control circuitry 1408, which is implemented in part on personal computing device 1410 and in part in circuitry components in/attached to headband 1424, includes stimulator control circuitry 1426 (portions of which are located on headband 1424) adapted to generate at least one stimulus control signal for controlling delivery of a transcutaneous neural stimulus to the cranial nerve with the transcutaneous neural stimulator 1404; prompter control circuitry 1428 adapted to generate at least one prompt control signal for controlling delivery of the prompt by the prompting system formed by earpiece 1402 and display 1412 of personal computing device 1410; and timing control circuitry 1430 for controlling a number of repetitions of the specific activity that the subject is prompted to perform by the at least one prompt and timing of delivery of the transcutaneous neural stimulus with respect to the at least one prompt.

A subject (e.g. a military veteran) 1432 displays PTSD and is treated with enhanced learning system 1400 that provides timed neural stimulation and cognitive training. The subject is provided with hardware for the enhanced learning system 1400 which includes personal computing device 1410 and headband 1424 including electrodes 1418 and 1420, and electrooculography sensor 1406. Electrode 1422 is attached to headband 1424 by a cable 1434, which allows it to be placed at a distance from the forehead on the back of the neck. Subject 1432 is trained to place earpiece 1402, headband 1424 (including electrodes 1418 and 1420), and electrode 1422, to deliver electrical stimulation to the trigeminal nerve complex in conjunction with a video game played on personal computing device 1410. The video game, produced by video game application 1414, is selected to remind the patient of traumatic events suffered during military service, and learning system 1400 prompts the patient to take positive action during the game in order to score points. Learning system 1400 also includes eyeglass 1436 which incorporates EOG sensors 1406 in the frames (see e.g., U.S. Patent Appl. 2015/0126845, Ibid, which is incorporated herein by reference) to monitor attention, anxiety and fatigue during game play. Based on EOG data, timing control circuitry 1430 may cause stimulator control circuitry 1426 to initiate electrical stimulation of the trigeminal nerve complex at an optimal time and duration. EOG signals may also indicate that different parameters for neural stimulation are required. For example, lower frequencies (i.e. 0.5-0.7 kHz versus 3-11 kHz) may be more efficacious (see e.g., Boasso et al., Ibid, which is incorporated herein by reference). Based on EOG signals, control circuitry may indicate another session of video gaming and neural stimulation is necessary and prompter control circuitry instructs 1428 the patient to repeat the videogame or play another videogame. Alternatively, EOG signals may indicate rest is required and prompter control circuitry 1428 will inform the patient. Electrical control circuitry 1408 analyzes EOG data and performance in the video game to detect any changes in cognitive behavior such as responsiveness, attention, anxiety, and fatigue. The schedule and protocol for using learning system 1400 may be adjusted to reflect any changes in cognition, and prompting system 1416 prompts the patient, under control of prompter control circuitry 1428, to alter the protocol and schedule.

In the example of FIG. 14, EOG sensor 1406 is used as a neural sensor to detect neural activity. In other embodiments, other types of neural sensors, for example, an EEG sensor, can be used to detect neural activity indicative of patient status. In some embodiments, the neural sensor is housed with the transcutaneous neural stimulator. In various embodiments, the transcutaneous neural stimulator can include a TENS unit or a patch electrode worn on the forehead, scalp, temple, face, or neck to deliver stimulation to a cranial nerve. In other embodiments, the transcutaneous neural stimulator can be worn on the ear of the patient, taking the form of an earbud or other earpiece, to deliver stimuli to the ear canal, concha, or other portions of the ear, as described in U.S. Published Patent Application No. 2016/0279435 to Hyde et al., which is incorporated herein by reference. A system as generally depicted in FIG. 14 can be used to enhance learning of a mental task, cognitive task, memory or recall task. In various aspect, prompting system 1416 can be configured (e.g. by video game application 1414) to deliver the at least one prompt for prompting the subject to perform aspects of various types of tasks, during the course of gameplay.

In some aspects, a transcutaneous neural stimulator includes at least a first portion adapted to fit within a first region of an ear of the subject (e.g., the ear canal) and a second portion adapted to fit within a second region of the ear of the subject (e.g., the concha) to deliver stimuli at different locations to access different nerves, or to provide a bipolar electrode configuration. In some aspects, the system includes two transcutaneous neural stimulators, one adapted to fit in or on a first ear of the subject and the other adapted to fit in or on a second ear of the subject. Although the embodiment depicted in FIG. 14 is configured to deliver stimuli to a trigeminal nerve of the subject, in other embodiments, the transcutaneous neural stimulator can be configured to stimulate other cranial nerves (e.g., the vagal nerve or glossopharyngeal), via the ear canal or concha, for example.

Figure 15:
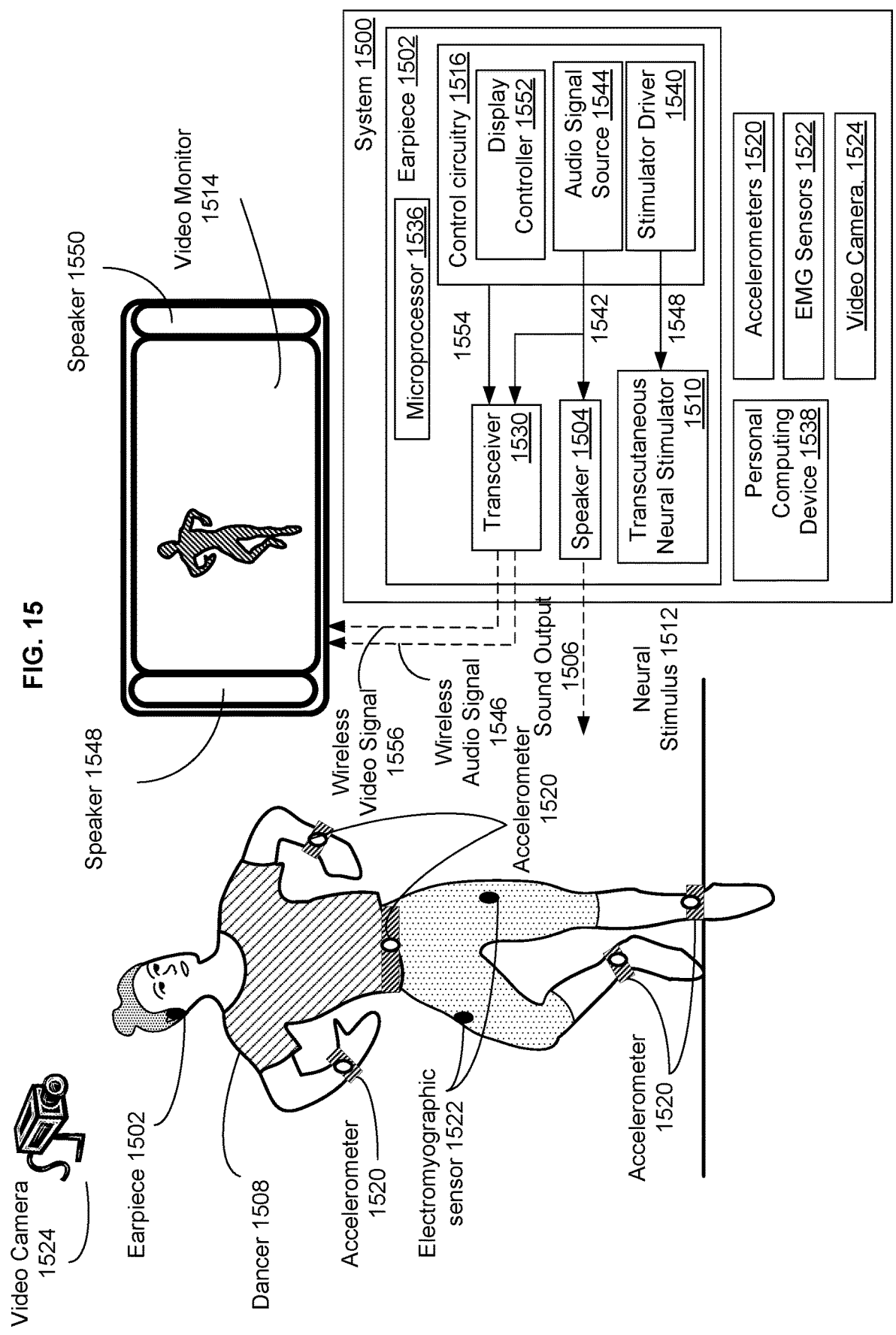
FIG. 15 depicts a training system.

FIG. 15 depicts a dance training system 1500 used to enhance learning of music and dance movements. Training system 1500 uses video and audio prompts combined with neural stimulation to enhance learning of choreography and music. The system includes an earpiece 1502 that contains a speaker 1504 that conveys a sound output 1506 including musical and verbal cues to the dancer 1508. Earpiece 1502 also contains a transcutaneous neural stimulator (TNS) 1510 for delivering a neural stimulus 1512 for enhancing learning to a cranial nerve. Visual prompts and other information are provided via video monitor 1514. Control circuitry 1516 is used to orchestrate and coordinate the neural stimulation and audio and video signals. Video monitor 1514 displays a video of example dance movements and visual representation of the musical score and timing cues. System 1500 includes movement sensors (e.g., accelerometers 1520, electromyographic sensors 1522) and a video camera 1524, to monitor the dancer's performance, inform the control circuitry 1516 and provide feedback to the dancer 1508 via video monitor 1514 and earpiece 1502.

The earpiece 1502 contains speaker 1504, a TNS 1510, control circuitry 1516 and transceivers 1530 for wireless connection with a personal computing device 1538 and video monitor 1514. An earpiece 1502 with high fidelity speaker 1504 and wireless connectivity (e.g., via transceiver 1530, which may be a Bluetooth or other RF transceiver) is incorporated with a TNS 1510 to provide electrical stimulation of the auricular branch of the vagus nerve. For example, a transcutaneous stimulator that is worn on the ear and stimulates the vagus nerve is available from Cerbomed, Erlangen, Germany. The training system earpiece 1502 incorporates circuitry (e.g., transceiver 1530) to receive input from movement sensors 1520 and 1522 worn by the dancer and from the video camera 1524. Microprocessor 1536 and control circuitry 1516 in earpiece 1502 process the movement data, evaluate dancer performance and control the timing, duration, and electrical parameters of neural stimulation. Also the number and duration of training sessions to learn the music and choreography is recommended by control circuitry 1516. A personal computing device 1538, e.g., a laptop, stores example dance videos, the associated music and music scores which are played coordinately with neural stimulation to promote neuronal plasticity and enhanced learning of motor skills and the associated music.

Dancer 1508 uses a dance training system 1500 to learn her part in a musical. Dancer 1508 activates the earpiece 1502, the laptop (1538) and video monitor 1514 and follows instructions from the earpiece 1502 and onscreen on video monitor 1514 to review the example video and music for the dance she will perform. Following the example performance onscreen, dancer 1508 is prompted to perform the dance following the music audio and onscreen video which includes timing cues for the dance movements. The stimulator driver 1540 under control of control circuitry 1516 provides neural stimulation timed to coincide with the dancer's performance. For example, vagus nerve stimulation with 0.8 mA, 100 μsec pulses at 30 Hz can be used to enhance motor skill training (see e.g. Dawson et al., Stroke 47, 143-150, 2016 which is incorporated herein by reference). Transcutaneous vagus nerve stimulation from an ear-mounted device may be done using a stimulus intensity of 0.5 mA, delivered with a pulse width of 200-300 μsec at 25 Hz and stimulation alternated between on and off periods every 30 sec. See e.g., Sellaro et al., *Journal of Cognitive Neuroscience* 27, 2126-2132, 2015 which is incorporated herein by reference. The control circuitry 1516 controls the timing and duration of the neural stimulation as well as the frequency, current and pulse length.

The training system monitors the dancer's performance with movement sensors 1520 and 1522 and a video camera 1524 (video camera 1524 may be a discrete camera, as depicted in FIG. 15, or may be incorporated into laptop 1538. Electromyographic (EMG) sensors 1522 are attached to the legs to monitor muscle activation, while accelerometers 1520 are attached at wrists, waist and ankles to monitor movement and position of limbs and torso. EMG data is transmitted wirelessly to the control circuitry 1516 via transceivers 1530), and processed to evaluate timing and movement during the dance (see e.g., Buchanan et al., *J. Applied Biomechanics* 20: 367-395, 2004 which is incorporated by reference herein). Video data of the dancer's performance from video camera 1524 is processed and compared to the example performance by the system circuitry. The dancer's performance is evaluated and suggested improvements and additional training sessions are recommended. Control circuitry 1516 may also modify the neural stimulation parameters (e.g., duration, current, timing) in response to the dancer's performance evaluation. Finally, improved performance is rewarded with audio kudos and positive reinforcement from the training system (via earpiece 1502 and video monitor 1514).

As described above, earpiece 1502 includes a speaker 1504 for delivering sound output 1506 to the ear of the dancer. Sound output 1506 is generated by speaker 1504 in response to an audio signal 1542 produced by audio signal source 1544, which is a component of control circuitry 1516. Alternatively, or in addition, audio signal 1542 generated by audio signal source 1544 is transmitted by transceiver 1530, as wireless audio signal 1546, to speakers 1548 and 1550. In FIG. 15, speakers 1548 and 1550 are depicted as being associated with video monitor 1514, but they can instead be housed separately. In general, any sound source connected (to audio signal source 1544 via either a wired or wireless connection can be used to produce a sound output responsive to audio signal 1542.

Microprocessor 1536, in association with control circuitry 1516 functions as a controller configured to control audio signal source 1544 and stimulator driver 1540 to control timing of delivery of the sound output 1506 and the neural stimulus 1512. For example, controller can be configured (e.g., via a user input of personal computing device 1538) to control audio signal source 1544 and stimulator driver 1540 to deliver the learning enhancing stimulus after delivery of the sound output, to deliver the sound output after delivery of the learning enhancing stimulus, or deliver the sound output at least partially overlapping in time with delivery of the learning enhancing stimulus.

Stimulator driver 1540 operatively connected to transcutaneous neural stimulator 1510 and configured to generate a stimulus control signal 1548 adapted to drive delivery of the learning enhancing stimulus by the at least one cranial nerve stimulator; and a controller (microprocessor 1536, control circuitry 1516) operatively connected to the audio signal source (speaker 1504) and the stimulator driver 1540 and configured to control at least one of generation of the audio signal 1542 the audio signal source 1544 and generation of the stimulus control signal 1548 by the stimulator driver 1540.

Video monitor 1514 is adapted to provide to the subject a visual prompt corresponding to a sound pattern. The sound pattern may be, for example, musical accompaniment for the dance being learned by dancer 1508. Display controller 1552 is configured to control presentation of the visual prompt via the display, by generating a display control signal 1554 which is transmitted as wireless video signal 1556 to video monitor 1514. In the embodiment of FIG. 15, a visual representation of a dance choreography corresponding to the sound pattern is depicted (e.g. a video of a performance of the dance). The choreography presented on video monitor 1514 can represent parts for one or multiple dancer. It will be appreciated that various combinations of visual prompt corresponding to a sound pattern are possible. For example, dialog or song lyrics corresponding could also be presented on the screen along with choreography (e.g. for use in musical theater productions). For example, in various aspects, display controller 1552 is configured to control presentation via video monitor 1514 of a musical score including a representation of the sound pattern, a script including text representing the sound pattern. The display depicted in FIG. 15 is a large screen display, but in other cases the display may be a screen of a smart phone, a tablet computer, a laptop computer, a desktop computer, a television, or a wearable device. In various aspects, displays used herein may also include projection displays (e.g., formed by using a projector to project an image onto a screen or other surface) or flexible displays.

FIG. 16 depicts an embodiment of a training system 1600, used to enhance learning of sound patterns by a subject 1602. In the example of FIG. 16, the system 1600 is used to assist subject 1602 in learning language vocabulary, but the system could be used for learning other sound patterns as well, as will be described in greater detail below. System 1600 includes an audio signal source 1604 which is adapted to generate an audio signal 1606 for driving production by a sound source 1608 of a sound output 1610 for delivery to the ear 1612 of the subject 1602. Sound output 1610 corresponds to a sound pattern to be learned by subject 1602. System 1600 includes at least one earpiece 1620 adapted to be carried by the ear 1612 of subject 1602, with at least one cranial nerve stimulator 1622 associated with earpiece 1620. Sound source 1608 is a small speaker carried in or associated with earpiece 1620. Cranial nerve stimulator 1622 is adapted to deliver a learning enhancing stimulus 1624 to a cranial nerve of subject 1602 in association with the sound pattern. Learning enhancing stimulus 1624 is adapted to enhance learning corresponding to the sound pattern by subject 1602. Stimulator driver 1626 is operatively connected to cranial nerve stimulator 1622 and configured to generate a stimulus control signal 1628 adapted to drive delivery of the learning enhancing stimulus 1624 by cranial nerve stimulator 1622. System 1600 also includes controller 1630, which is operatively connected to audio signal source 1604 and stimulator driver 1626 and configured to control generation of audio signal 1606 by the audio signal source 1604 and generation of stimulus control signal 1628 by stimulator driver 1626.

Earpiece 1620 is configured as a headset, with a neural stimulator configured to stimulate a cranial nerve of the subject for example as described in U.S. Published Patent Application No. 2016/0279435 to Hyde et al., which is incorporated herein by reference. Controller 1630, audio signal source 1604, and stimulator driver 1626 are components of a personal computing device 1632, here depicted as a table computer. However, although FIG. 16 depicts system 1600 implemented in connection with a table computer, in other embodiments some or all system components (e.g., audio signal source, stimulator driver, and controller) can be implemented on other devices, such as a smart phone, laptop computer, desktop computer, television, or wearable device. System 1600 delivers prompts, feedback, and other communications to subject 1602 via display 1634 of personal computing device 1632, and via sound source 1608 (or, alternatively, or in addition, a sound source built into or associated with personal computing device 1632).

Earpiece 1620 is depicted being connected to personal computing device 1632 via a wired connection (cable 1636) in FIG. 16, but may alternatively be connected via a wireless link, e.g., via Bluetooth connection.

System 1600 also includes attention sensor 1638 which is an eye tracking sensor (implemented with a camera built into personal computing device 1632) operatively connected to the controller 1630, which is used for sensing eye movement parameters indicative of attentiveness of the subject.

An attention tracking module 1640 (as described generally in connection with FIG. 3) is operatively connected to the attention sensor 1638, and adapted to detect attentiveness of the subject based on the at least one parameter indicative of attentiveness of the subject. The attention tracking module is adapted to generate a notification if the subject is not attentive. The notification includes an audio alarm tone delivered via earpiece 1620.

As noted above, prompts, feedback, and other communications are delivered to subject 1602 via display 1634 of personal computing device 1632, and via sound source 1608 (or, alternatively, or in addition, a sound source built into or associated with personal computing device 1632). Visual prompts corresponding to the sound pattern and delivered via display 1634 may include, for example, a script including text representing a sound pattern. In the example of FIG. 16, a text prompt 1642 includes a list of vocabulary words. In various aspects, the script includes speech, a poem, a scripted dialog, a dramatic script, one or more spelling words, one or more vocabulary words, one or more phrases, sentences, or paragraphs. The script can be for one or multiple speakers.

An audio prompt is provided as sound output 1610 (in the example of FIG. 16, an audio prompt of the words "uno, dos, tres."

Attention sensor 1638 forms a component of a sensing system, while sound source 1608 and display 1634 form components of a prompting system, as described in connection with FIGS. 2 and 3. System 1600 includes various other components, which are as depicted and described in connection with FIGS. 2, 3 and 4, and are not described in detail in connection with FIG. 16. For example, system 1600 can include a reporting circuitry, reward module as described in connection with FIG. 3.

In addition to the audio alarm noted above, system 1600 can be configured to deliver additional or alternative notifications, such as a verbal notification, a visible notification, a tactile notification, or an electronic notification, which can be stored in a data storage location or transmitted to at least one additional location. For example, a notification transmitted to an additional location could include a notification delivered to a parent, a teacher, a coach, a medical care provider, or other parties as appropriate to a particular learning or training program that the subject is engaged in. Communication circuitry 1646 in system 1600 (e.g., a component of personal computing device 1632) is adapted to provide communication between controller 1630 and a computing or communication network 1648, and thus to one or more remote system 1650.

System 1600 includes sound sensor 1652 (e.g., a microphone) operatively connected to controller 1630 and adapted to sense a sound pattern produced by the subject. For example, after viewing one or more of text prompt 1642 on display 1634 or a sound output 1610 including an audio prompt delivered via sound source 1608, subject 1602 practices speaking the vocabulary words. Performance assessment module 1654 is adapted to evaluate learning corresponding to the sound pattern by the subject based on the sensed sound pattern produced by the subject. In an aspect, performance assessment module 1654 includes a speech analyzer that can be used to assess various aspects of the sound pattern produced by the subject (e.g., speech) to evaluate learning. In general, the sound pattern produced by the subject can be assessed by comparing a parameter of the sound pattern to a target parameter. Parameters include, but are not limited to, audio waveform, rhythm, tempo, pitch, intonation, emphasis, and pronunciation. In some aspects, the assessment module performs speech recognition to identify words and assess word meaning and usage. In learning a foreign language, proper pronunciation is of interest. In the case that the subject is learning the spelling of a word, the subject may repeat the word and subsequently recite the letters spelling the word. In the case that the subject is learning the meaning of vocabulary words, the subject may repeat a phrase containing a definition of the word. For example, in an aspect, performance assessment module 1654 is adapted to determine one or more word from the sensed sound pattern and compare it to a target word. In other aspects, comparisons are made between determined word meaning, grammar, word order, or letter order in comparison to a respective target. Performance assessment module 1654 utilizes a performance rating system to assign at least one performance rating to a performance of the audible task by the subject.

System 1600 also includes a feedback system adapted to provide feedback to the subject based upon the at least one performance rating (feedback can be provided in the form of a numerical score indicating percent match with target, a verbal assessment, which can be general ("good job," "needs improvement") or specific ("pronunciation is 'A,' not 'aye'"), which as described above in connection with FIGS. 2 and 3 utilizes sound source 1608 and display 1634 to deliver feedback to subject 1602. System 1600 includes reporting circuitry, which, as described above in connection with FIG. 3, provides a report to one or more of the subject, a parent, an instructor, a coach, a medical care provider, or a peer based upon the at least one performance rating.

Figure 17:
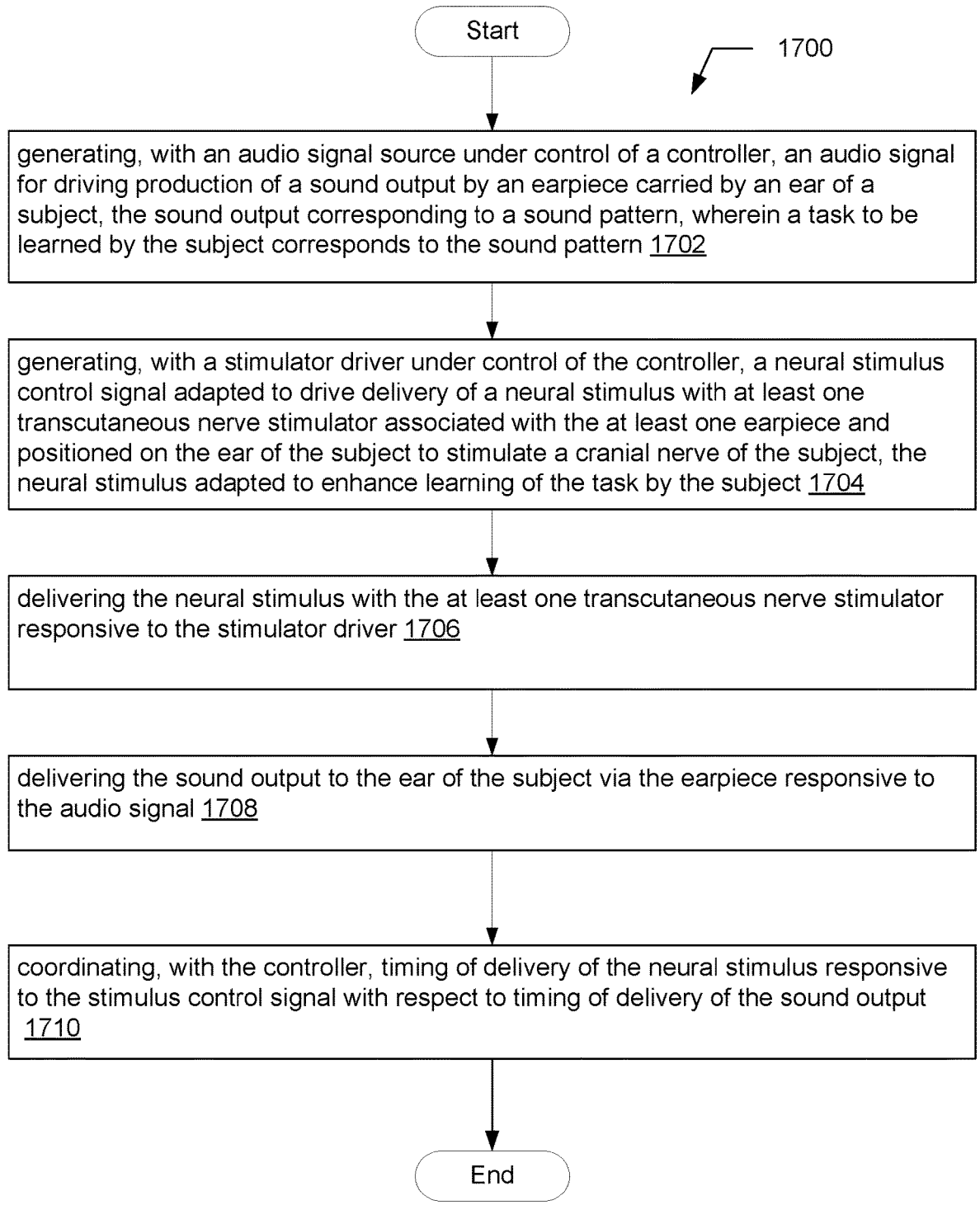
FIG. 17 is a flow diagram of a method for training a subject to perform a task.

FIG. 17 is a flow diagram of a method 1700 for training a subject to perform a task corresponding to a sound pattern, which can be carried out using systems as depicted in FIGS. 15 and 16, for example. Method 1700 includes generating, with an audio signal source under control of a controller, an audio signal for driving production of a sound output by an earpiece carried by an ear of a subject, the sound output corresponding to a sound pattern, wherein a task to be learned by the subject corresponds to the sound pattern, at 1702; generating, with a stimulator driver under control of the controller, a neural stimulus control signal adapted to drive delivery of a neural stimulus with at least one transcutaneous nerve stimulator associated with the at least one earpiece and positioned on the ear of the subject to stimulate a cranial nerve of the subject, the neural stimulus adapted to enhance learning of the task by the subject, at 1704; delivering the neural stimulus with the at least one transcutaneous nerve stimulator responsive to the stimulator driver, at 1706; delivering the sound output to the ear of the subject via the responsive to the audio signal, at 1708; and coordinating, with the controller, timing of delivery of the neural stimulus responsive to the stimulus control signal with respect to timing of delivery of the sound output, at 1710.

Figure 18:
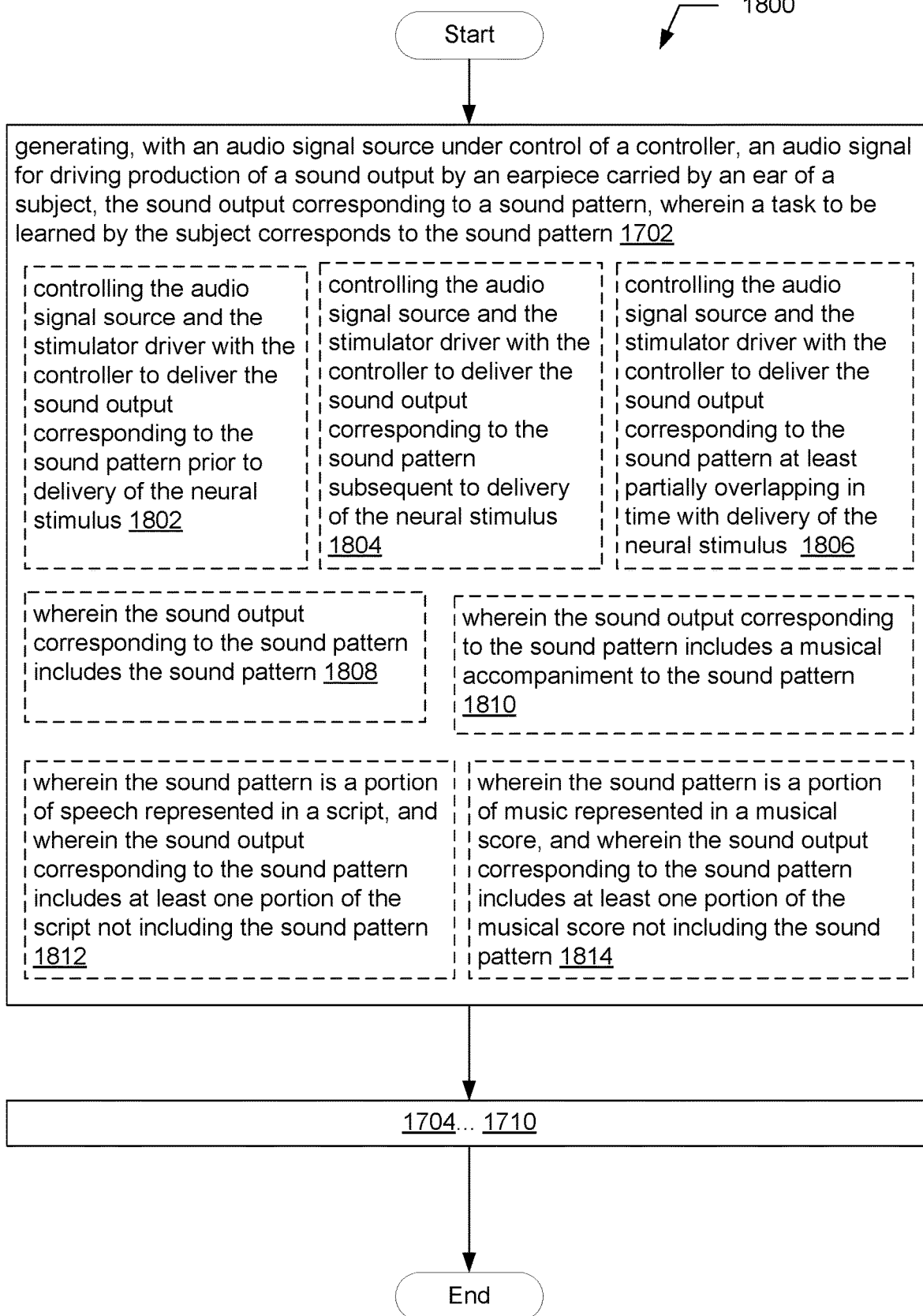
FIG. 18 is a flow diagram of a method.

FIGS. 18-23 depict further aspects relating to method 1700 shown in FIG. 17, and steps 1702-1710 are as discussed in connection with FIG. 17. FIG. 18 illustrates method aspects relating to the sound output. In an aspect, method 1800 includes controlling the audio signal source and the stimulator driver with the controller to deliver the sound output corresponding to the sound pattern prior to delivery of the neural stimulus, as indicated at 1802. In another aspect, method 1800 includes controlling the audio signal source and the stimulator driver with the controller to deliver the sound output corresponding to the sound pattern subsequent to delivery of the neural stimulus, as indicated at 1804. In another aspect, method 1800 includes controlling the audio signal source and the stimulator driver with the controller to deliver the sound output corresponding to the sound pattern at least partially overlapping in time with delivery of the neural stimulus, as indicated at 1806.

In various aspects, the sound output corresponding to the sound pattern includes the sound pattern, as indicated at 1808, or a musical accompaniment to the sound pattern, as indicated at 1810, (for example, in the case that the sound pattern is a musical part for a vocalist, or for an instrumental soloist). To test the subject's memorization of his or her part, the subject's part may be omitted from the prompt, and only parts played by others may be presented. For example, the sound pattern is a portion of speech represented in a script, and the sound output corresponding to the sound pattern includes at least one portion of the script not including the sound pattern, as indicated at 1812. Similarly, as another example, the sound pattern is a portion of music represented in a musical score, and the sound output corresponding to the sound pattern includes at least one portion of the musical score not including the sound pattern, as indicated at 1814.

Figure 19:
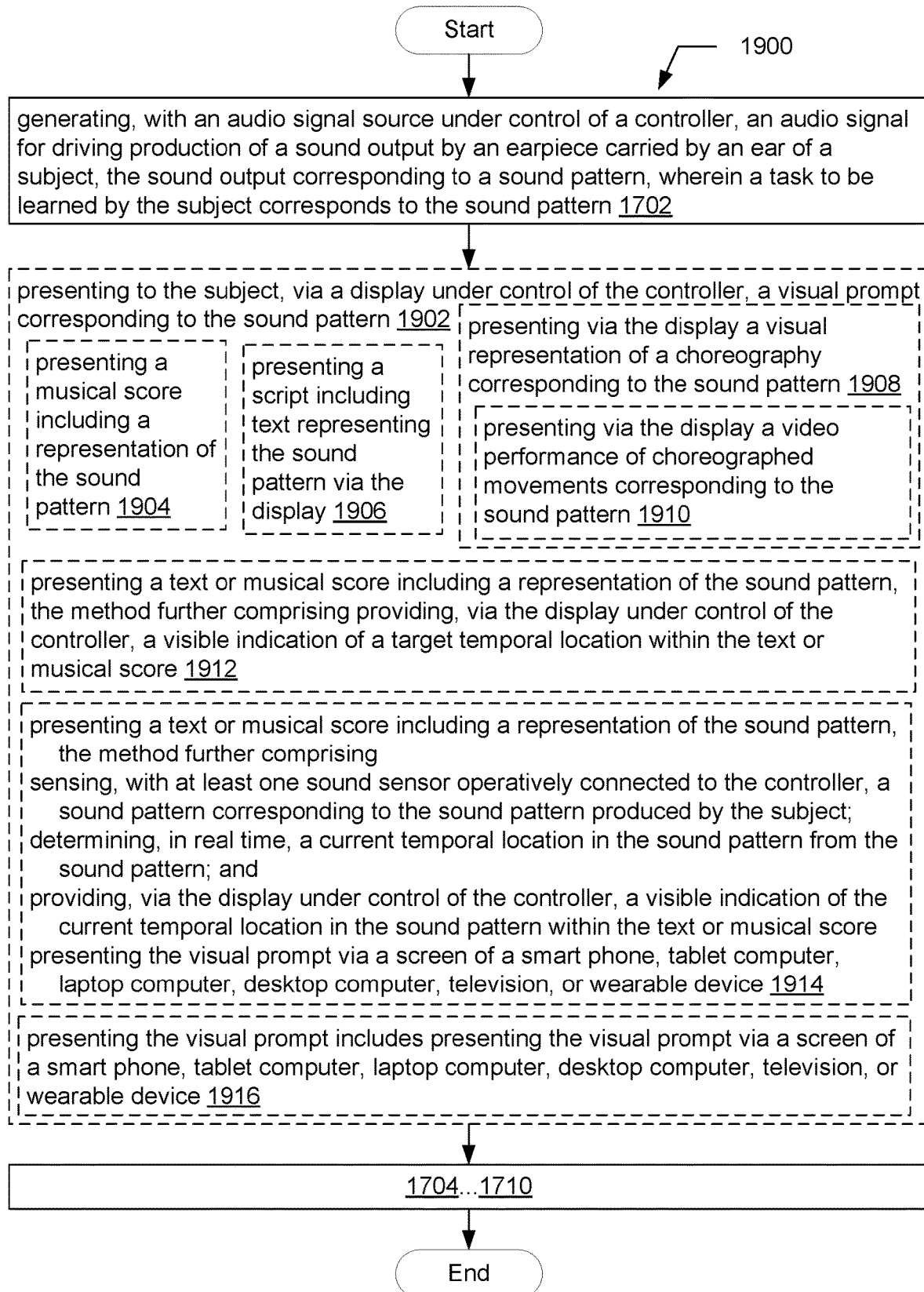
FIG. 19 is a flow diagram of a method.

FIG. 19 is a flow diagram of a method 1900, which includes presenting to the subject, via a display under control of the controller, a visual prompt corresponding to the sound pattern, as indicated at 1902. In an aspect, presenting the visual prompt corresponding to the sound pattern includes presenting a musical score including a representation of the sound pattern, as indicated at 1904. For example, a score can be a vocal or instrumental score, and/or a score for an individual, an ensemble, or a soloist plus an accompaniment, without limitation.

In an aspect, presenting the visual prompt corresponding to the sound pattern includes a presenting a script including text representing the sound pattern via the display, as indicated at 1906. For example, in various aspects, the script includes speech, a poem, a scripted dialog, a dramatic script, one or more letters, one or more words, one or more spelling words, one or more vocabulary words, one or more phrases, sentences, or paragraphs. The script can include any text to be learned or memorized, e.g. foreign language vocabulary; numbers, equations, mathematical constant, or mathematical constructs; facts, theorems, theories, corollaries; and combinations of numbers, letter, and/or words (including lock combinations, passwords, etc.). The script can be for one or multiple speakers. It will be appreciated that the script may contain one or both of a part being learned by the subject, and parts spoken by one or more others. To test the subject's memorization of his or her part, the subject's part may be omitted from the prompt, and only parts spoken by others may be presented.

In yet another aspect, presenting the visual prompt corresponding to the sound pattern includes presenting via the display a visual representation of a choreography corresponding to the sound pattern, as indicated at 1908. For example, in an aspect, presenting the visual prompt corresponding to the sound pattern includes presenting via the display a video performance of choreographed movements corresponding to the sound pattern, as indicated at 1910, as depicted in FIG. 15.

Figure 25:
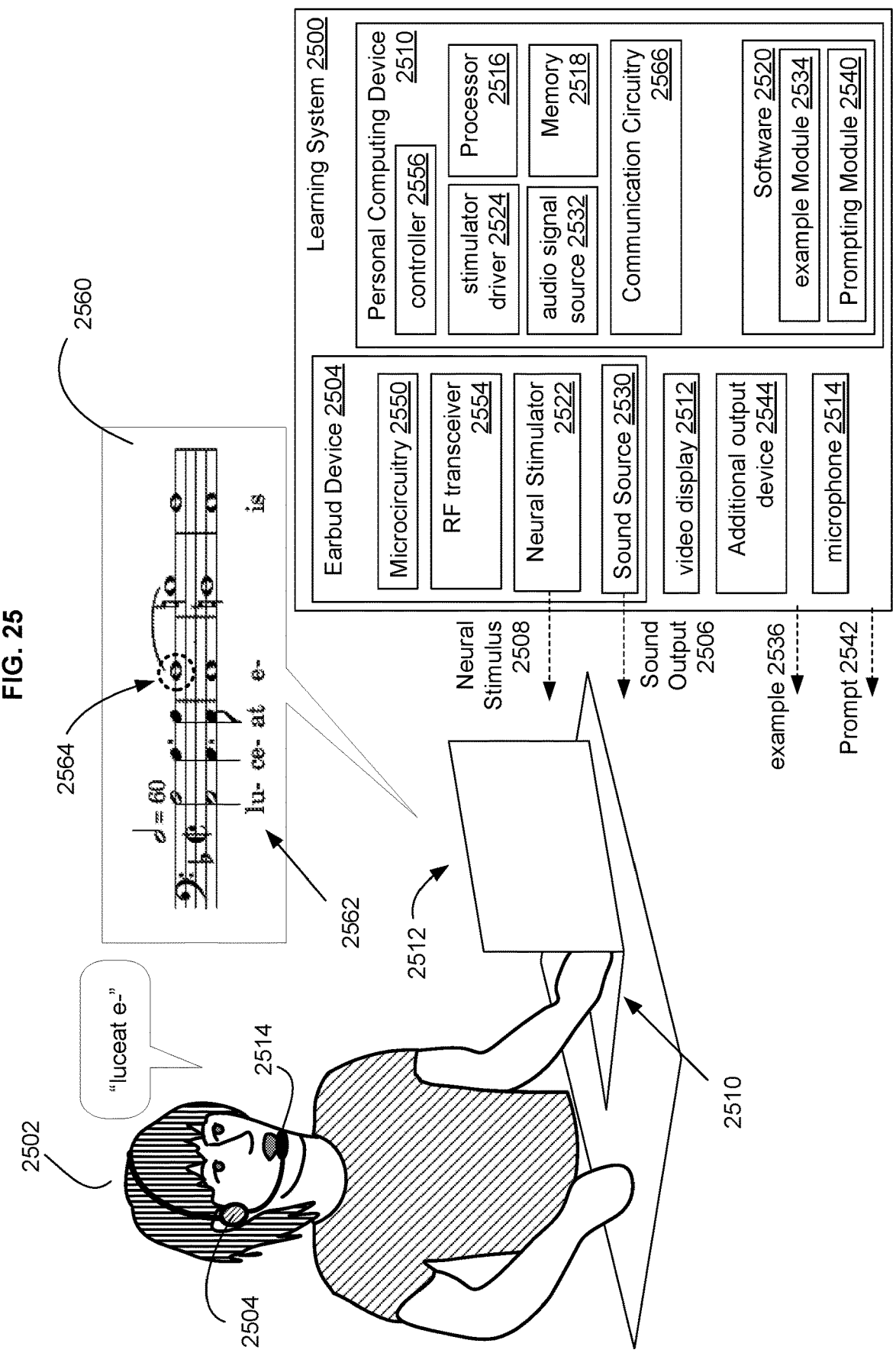
FIG. 25 depicts a learning system for enhancing learning of a sound pattern.

In another aspect, presenting the visual prompt corresponding to the sound pattern includes presenting a text or musical score including a representation of the sound pattern (for example, by various means as described herein above), the method further comprising providing, via the display under control of the controller, a visible indication of a target temporal location within the text or musical score, as indicated at 1912. FIG. 25 shows an example of a visible indication of a target temporal location indicated within a musical score.

In yet another aspect, presenting the visual prompt corresponding to the sound pattern includes presenting a text or musical score including a representation of the sound pattern, the method further comprising sensing, with at least one sound sensor operatively connected to the controller, a sound pattern corresponding to the sound pattern produced by the subject; determining, in real time, a current temporal location in the sound pattern from the sound pattern; and providing, via the display under control of the controller, a visible indication of the current temporal location in the sound pattern within the text or musical score, as indicated at 1914. In another aspect, presenting the visual prompt includes presenting the visual prompt via a screen of a smart phone, tablet computer, laptop computer, desktop computer, television, or wearable device, as indicated at 1916.

Figure 20:
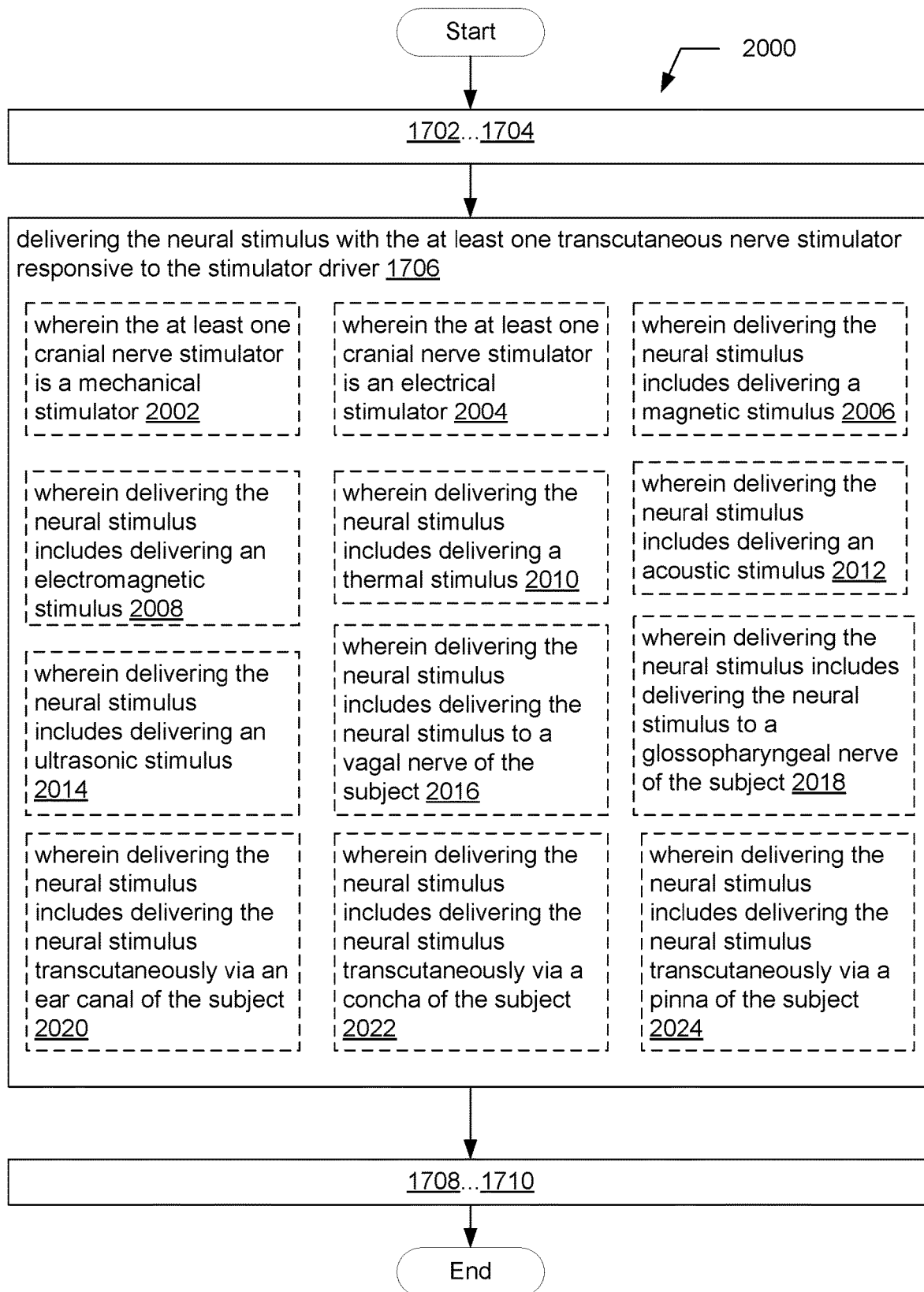
FIG. 20 is a flow diagram of a method.

FIG. 20 depicts a method 2000 illustrating various aspects relating to delivering the neural stimulus with the at least one transcutaneous nerve stimulator responsive to the stimulator driver at 1706. For example, in various aspects, the at least one cranial nerve stimulator is a mechanical stimulator, as indicated at 2002; or an electrical stimulator, as indicated at 2004. In other aspects, delivering the neural stimulus includes delivering a magnetic stimulus, as indicated at 2006; an electromagnetic stimulus, as indicated at 2008; a thermal stimulus, as indicated at 2010; an acoustic stimulus, as indicated at 2012; or an ultrasonic stimulus, as indicated at 2014. In various aspects, delivering the neural stimulus includes delivering the neural stimulus to a vagal nerve of the subject, as indicated at 2016; or a glossopharyngeal nerve of the subject, as indicated at 2018. In other aspects, delivering the neural stimulus includes delivering the neural stimulus transcutaneously via an ear canal of the subject, as indicated at 2020; a concha of the subject, as indicated at 2022; or a pinna of the subject, as indicated at 2024.

Figure 21:
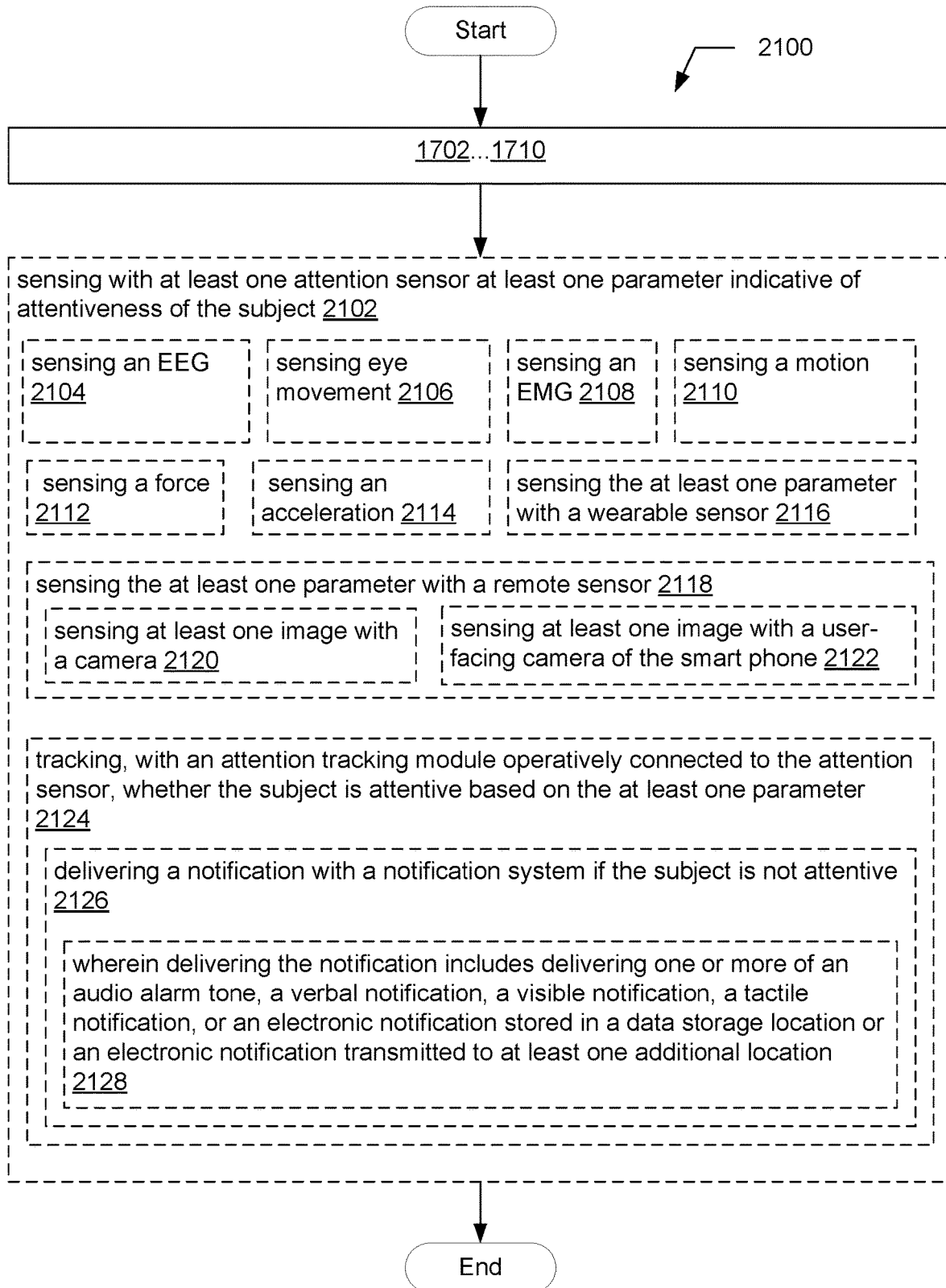
FIG. 21 is a flow diagram of a method.

FIG. 21 depicts a method 2100 including sensing with at least one attention sensor at least one parameter indicative of attentiveness of the subject, as indicated at 2102. In various aspects, sensing the at least one parameter indicative of attentiveness of the subject includes sensing an EEG, at 2104; eye movement, at 2106; an EMG, at 2108; a motion, as indicated at 2110; a force, as indicated at 2112; or an acceleration, as indicated at 2114.

In various aspects, sensing the at least one parameter indicative of attentiveness of the subject includes sensing the at least one parameter with a wearable sensor, at 2116 or a remote sensor, at 2118. For example, in an aspect, sensing the at least one parameter indicative of attentiveness of the subject includes sensing at least one image with a camera, as indicated at 2120. In an aspect, sensing the at least one parameter indicative of attentiveness of the subject includes sensing at least one image with a user-facing camera of the smart phone, as indicated at 2122.

In another aspect, method 2100 includes tracking, with an attention tracking module operatively connected to the attention sensor, whether the subject is attentive based on the at least one parameter, as indicated at 2124. In connection therewith, method 2100 includes delivering a notification with a notification system if the subject is not attentive, as indicated at 2126. For example, in various aspects, delivering the notification includes delivering one or more of an audio alarm tone, a verbal notification, a visible notification, a tactile notification, or an electronic notification stored in a data storage location or an electronic notification transmitted to at least one additional location, as indicated at 2128.

Figure 22:
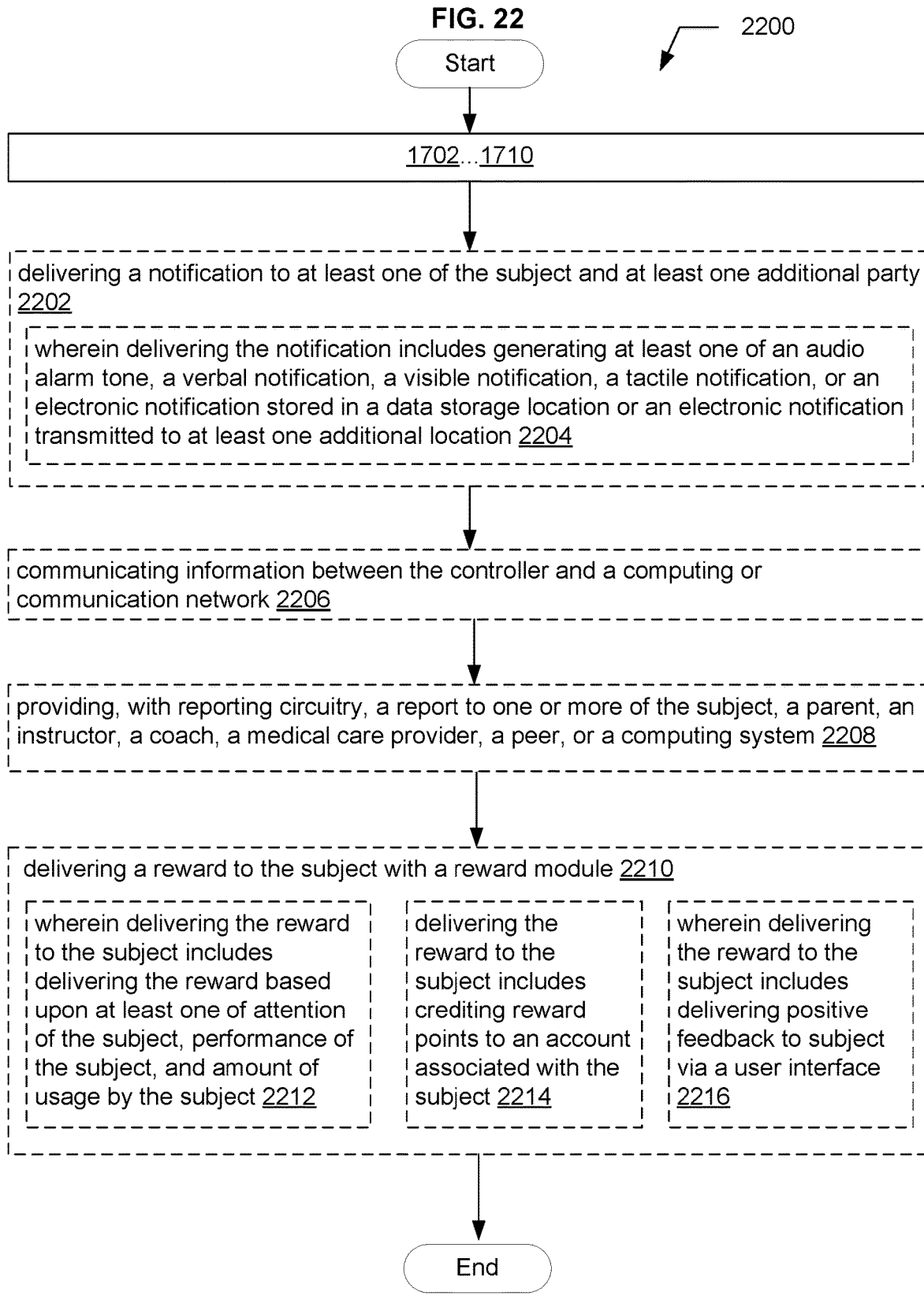
FIG. 22 is a flow diagram of a method.

FIG. 22 depicts a method 2200 illustrating other aspects relating to delivery of notifications, as well as providing reports and other communications. In an aspect, method 2200 includes delivering a notification to at least one of the subject and at least one additional party, as indicated at 2202. For example, in various aspects, delivering the notification includes generating at least one of an audio alarm tone, a verbal notification, a visible notification, a tactile notification, or an electronic notification stored in a data storage location or an electronic notification transmitted to at least one additional location, as indicated at 2204.

In an aspect, method 2200 includes communicating information between the controller and a computing or communication network, as indicated at 2206.

In an aspect, method 2200 includes providing, with reporting circuitry, a report to one or more of the subject, a parent, an instructor, a coach, a medical care provider, or a peer, as indicated at 2208. In an aspect, this includes delivering a reward to the subject with a reward module, as indicated at 2210. In various aspects, delivering the reward to the subject includes delivering the reward based upon at least one of attention of the subject, performance of the subject, and amount of usage by the subject, as indicated at 2212. In another aspect, delivering the reward to the subject includes crediting reward points to an account associated with the subject, as indicated at 2214. For example, in various aspects, reward points can be redeemable for money, a physical reward item, game play, games status, or other actual or virtual rewards. In another aspect, delivering the reward to the subject includes delivering positive feedback to subject via a user interface, as indicated at 2216.

Figure 23:
FIG. 23 is a flow diagram of a method.

FIG. 23 depicts a method 2300, including sensing with at least one sound sensor a sound pattern produced by the subject, at 2302. In connection therewith, method 2300 includes evaluating learning corresponding to the sound pattern by the subject with a performance assessment module based on the sensed sound pattern produced by the subject, as indicated at 2304. In various aspects, evaluating learning corresponding to the sound pattern by the subject includes analyzing the sensed sound pattern with a speech analyzer, at 2306; determining one or more audio waveform from the sensed sound pattern and comparing it to a target audio waveform, at 2308; determining one or more rhythm from the sensed sound pattern and comparing it to a target rhythm, at 2310; determining one or more tempo from the sensed sound pattern and comparing it to a target tempo, at 2312; determining one or more pitch from the sensed sound pattern and comparing it to a target pitch, at 2314; determining one or more intonation from the sensed sound pattern and comparing it to a target intonation, at 2316; determining one or more emphasis from the sensed sound pattern and comparing it to a target emphasis, at 2318; determining one or more pronunciation from the sensed sound pattern and comparing it to a target pronunciation, at 2320; determining one or more word from the sensed sound pattern and comparing it to a target word, at 2322; determining one or more word meaning from the sensed sound pattern and comparing it to a target word meaning, at 2324; determining one or more grammar from the sensed sound pattern and comparing it to a target grammar, at 2326; determining one or more word order from the sensed sound pattern and comparing it to a target word order, at 2328; or determining one or more letter order from the sensed sound pattern and comparing it to a target letter order, at 2330.

In an aspect, method 2300 includes assigning at least one performance rating based on an output of the performance assessment module, at 2332. In an aspect, method 2300 includes delivering, with a feedback system, feedback to at least one of the subject and another party based upon the at least one performance rating, as indicated at 2334. In an aspect, method 2300 includes delivering the neural stimulus to the subject based at least in part on the at least one performance rating, as indicated at 2336. In an aspect, method 2300 includes delivering a stimulus that blocks learning by the subject based at least in part on the at least one performance rating, as indicated at 2338.

FIG. 24 depicts a computer program product 2400 for implementing a method as described in connection with FIG. 17. Computer program product 2400 includes at least one non-transitory computer-readable medium 2402, bearing one or more instructions for generating, with an audio signal source under control of a controller, an audio signal for driving production of a sound output by an earpiece carried by an ear of a subject, the sound output corresponding to a sound pattern, wherein a task to be learned by the subject corresponds to the sound pattern; one or more instructions for generating, with a stimulator driver under control of the controller, a neural stimulus control signal adapted to drive delivery of a neural stimulus with at least one transcutaneous nerve stimulator associated with the at least one earpiece and positioned on the ear of the subject to stimulate a cranial nerve of the subject, the neural stimulus adapted to enhance learning of the task by the subject; and one or more instructions for coordinating, with the controller, timing of delivery of the neural stimulus responsive to the stimulus control signal with respect to timing of delivery of the sound output, as indicated at 2404. Non-transitory computer-readable medium 2402 may be, for example, a recordable medium 2406.

Computer program product 2400 may include instructions for performing various aspects of method steps outlined in FIGS. 18-23. For example, in an aspect non-transitory computer-readable medium 2402 bears instructions relating to method aspects shown in FIG. 18, including one or more instructions for presenting a visual prompt corresponding to the sound pattern, the visual pattern including a text or musical score including a representation of the sound pattern; one or more instructions for sensing, with at least one sound sensor operatively connected to the controller, a sound pattern corresponding to the sound pattern produced by the subject; one or more instructions for determining, in real time, a current temporal location in the sound pattern from the sound pattern; and one or more instructions for providing, via the display under control of the controller, a visible indication of the current temporal location in the sound pattern within the text or musical score.

FIG. 25 depicts a learning system 2500 which is used for enhancing learning of a sound pattern by a subject 2502. In the example of FIG. 25, subject 2502 is a singer who uses learning system 2500 to learn a musical piece and improve his vocal performance. The learning system 2500 includes an earbud device 2504 which delivers a sound output 2506 and neural stimulus 2508 to subject 2502 during training sessions. The system includes a personal computing device 2510 with a video display 2512, microphone 2514, processor 2516, memory 2518 and software 2520 to coordinate audiovisual instruction, prompting, neural stimulation, performance evaluation and feedback to the singer.

Learning system 2500 includes a neural stimulator 2522 located in earbud device 2504. Neural stimulator 2522 is used for delivering a neural stimulus 2508 adapted to enhance learning of a sound pattern by subject 2502. Learning system 2500 includes stimulator driver 2524, which adapted to drive delivery of neural stimulus 2508 by neural stimulator 2522. In addition, learning system 2500 includes sound source 2530 which is adapted to provide a sound output 2506 to the subject, audio signal source 2532 which is adapted to drive delivery of sound output 2506 by sound source 2530. Software 2520 includes example module 2534 for controlling delivery of an example 2536 of the sound pattern to subject via at least one of sound source 2530 and video display 2512, and prompting module 2540 for driving delivery of prompt 2542 via at least one of sound source 2530, video display 2512, or an additional output device 2544, in association with delivery of neural stimulus 2508 by neural stimulator 2522. Aside from a primary main visual prompt provided via video display 2512, system 2500 can be programmed to deliver additional or supplemental prompts from an additional output device. For example, various audible prompts (e.g. tones, verbal instructions, etc.) can be delivered via sound source 2530 or another sound source under control of controller 2556. A flashing light or other visually detectable prompt can be provided via a controllable light source, controllable light-reflective device, or controllable color-changing device on or controlled by personal computing device 2510. Additional output device 2544 can include a tactile or haptic stimulus source (e.g., a small vibrator on earbud device 2504) controlled by personal computing device 2510 that delivers a non-audible stimulus.

Earbud device 2504 contains miniature speakers which function as sound source 2530 to provide audio instruction, prompts and musical examples to the subject 2502. Earbud 2504 (and an earbud on the other ear, not shown) also contain neural stimulator 2522 which is a transcutaneous neural stimulator (TNS) to stimulate the vagus nerve in conjunction with performance of the musical piece. For example, wearable ultrasound devices (see e.g., Lewis Jr. et al., *Ultrasound in Med. and Biol.* 39: 1429-1439, 2013) may be incorporated in the earbuds that rest inside the tragus of the ear to provide stimulation to the auricular branch of the vagus nerve (see e.g., U.S. Pat. No. 7,797,042 issued to Dietrich et al. on Sep. 14, 2010 which is incorporated herein by reference). The ultrasound device is empowered and controlled remotely by personal computing device 2510 via wireless transmission at radio frequency (RF) wavelengths. Earbud device 2504 includes microcircuitry 2550 and RF transceivers 2552 to receive and transmit RF signals. The personal computing device 2510 includes video display 2512, audio signal source 2532, RF transceiver 2554, memory 2518, processor 2516, controller 2556 and software 1520 to provide: instructions, example musical performances, musical cues and accompaniment, and to coordinate timing and control of neural stimulation with musical performance. The computer system is programmed to control the extent and timing of neural stimulation based on performance evaluation and comparison to previous performances. Personal computing device 2510 is also programmed to evaluate musical performances, suggest improvements, and to provide feedback to the student as well as to a teacher or mentor.

Subject 2502 begins a training session with learning system 2500 by programming the personal computer to train for a musical piece (e.g., the Faure Requiem). The learning system software 2520 includes an instructional audiovisual on the training system protocol, an example audio performance of the Requiem, a video of the musical score and lyrics; cues for singing the musical piece, and an audio of musical accompaniment for singing the Requiem. Subject 2502 dons earbud device 2504 placing the earbuds in each ear canal and initiates the learning system program on personal computing device 2510. An instructional video delivered via video display 2512 and sound source 2530 in earbud device 2504 describes the training protocol:

1) Listen to the example performance (an audio example delivered via sound source 2530) and watch the video of musical score and lyrics (a visual example 2560 delivered via video display 2512) and mentally rehearse the performance. Neural stimulation, i.e., ultrasound stimulation from the earbud device starts and ends simultaneously with the example performance.
2) Sing in response to audiovisual prompts (audio of accompaniment music delivered via sound source 2530; video of musical score and lyrics delivered via video display 2512); ultrasound neural stimulation occurs simultaneous to the student's performance.
3) Performance evaluation by the learning system algorithms is applied to the audio recording and includes comparison to the example performance and any previous student performances. Performance parameters may include: pitch, timing/tempo, intonation, and lyric memorization and pronunciation.
4) Feedback is provided to the singer critiquing the performance and providing suggested improvements.

Following the instructional video the singer's initial performance is prompted by the audiovisual system and recorded via the microphone in the personal computer. The singer is guided by the video of the lyrics and the musical score, and the timing of the lyrics and musical accompaniment is indicated on the video display. The singer's performance is evaluated by the system with respect to pitch, timing/tempo, intonation, and lyric memorization and pronunciation as compared to the example performance. Feedback to the singer includes corrective actions to improve the performance, and preparation for a second performance.

A second performance is prompted by the audiovisual system (see step 2 in protocol above) and ultrasound stimulation from the earbuds is initiated immediately following the prompt. Upon completion of the song neurostimulation is stopped and the learning system evaluates the performance and compares it to the example performance and the initial performance. If the current performance meets minimum standards of performance (e.g., correct pitch, sufficient range, intonation, timing, tempo, pronunciation, lyrics) then the system will provide neural stimulation with the next performance. Feedback to the singer will include areas for improvement, strong points of the performance, and instructions for the next performance.

The third performance is prompted as above (see step 2) and the system will initiate neural stimulation, i.e., ultrasound stimulation of the vagus nerve, simultaneous with the start of the singing performance. Ultrasound stimulation is sustained for the duration of the performance, and afterwards the third performance is evaluated and feedback is provided to the student in preparation for a fourth performance.

A training session may include multiple performances, e.g., five or more, with each performance evaluated and the feedback adjusted as needed to improve the performance. Neural stimulation is provided if an improved performance is detected or a minimum level of performance is attained compared to the example performance. Neural stimulation may be contingent on improved scores from performance to performance. The enhanced learning system may also provide a reward at the end of the training session in the form of positive feedback, credits for coursework, or points in a self-directed training system. Competitive performances between two students may be orchestrated and evaluated by the system.

Example module 2534 is adapted to control delivery of an audible example of the sound pattern to subject 2502 via at least one sound source 2530, and is also adapted to control delivery of a visual representation of the sound pattern to the subject via display 2512, i.e., example module 2534 is adapted to control presentation of musical score 2560 on display 2512. In addition, example module 1524 is adapted to control presentation of a text (e.g., lyrics 2562) on display 2512. It will be appreciated that in other uses of the training system, the text may include one or more of a script, a speech, song lyrics, one or more word, one or more paragraph, one or more phrase, one or more spelling words, or one or more vocabulary words. In addition, example module is adapted to cause the display of one or more marker 2564 in the visual representation indicating a time-varying location within the visual representation. As depicted in FIG. 25, the marker is a dashed circle around the note that subject 2502 should be singing. It will be appreciated that the current location in the score (or script, or other visual representation) can be indicated by various means under control of software 2520, e.g. with an arrow rather than a circle as depicted in FIG. 25, or by highlighting the note or text with a larger, brighter or otherwise distinctive font, with a different color or brightness, etc. in order to indicate the location within the score. As depicted in FIG. 25, the "current location" is a target temporal location representing the portion of the score that the subject should be performing at a particular time; it also indicates a target note (pitch) to be produced by the subject. Although not depicted in FIG. 25, it would also be possible to depict the actual current location of the subject in addition to the target current location. In the event that subject 2502 was singing off key or too slowly, the depiction of the actual current location would help the subject to recognize the need to correct pitch or timing.

In an alternative embodiment of the system shown in FIG. 25, the sound source (e.g., a speaker) and neural stimulator could be mounted in a headphone rather than an earbud.

As described elsewhere herein, in various aspects prompting module 2540 can be configured to drive delivery of the prompt at a set interval prior to delivery of the neural stimulus, a set interval subsequent to delivery of the neural stimulus, or at a time overlapping at least in part with delivery of the neural stimulus. Memory 2518 in learning system 2500 serves as a data storage location containing one or more data structure for storing data representing the example of the sound pattern, information relating to at least one of the example, the prompt, and the neural stimulus, etc. In an aspect, example module 2534 is adapted to retrieve an example of the sound pattern from the data storage location. In some cases, communication circuitry 2566 in personal computing device 2510 can receive data representing the example of the sound pattern from a remote location via a communication or computing network, e.g. as described in connection with U.S. Published Patent Application No. 2016/0279435 to Hyde et al., which is incorporated herein by reference. Communication circuitry 2566 can also be used for transmitting information relating to at least one of the examples, the prompt, and the neural stimulus to a remote location via a communication or computing network. Information relating to at least one of the example, the prompt, and the neural stimulus can be received from the subject via a user interface associated with personal computing device 2510 (e.g., a keyboard, a mouse, a touch-screen).

Figure 26:
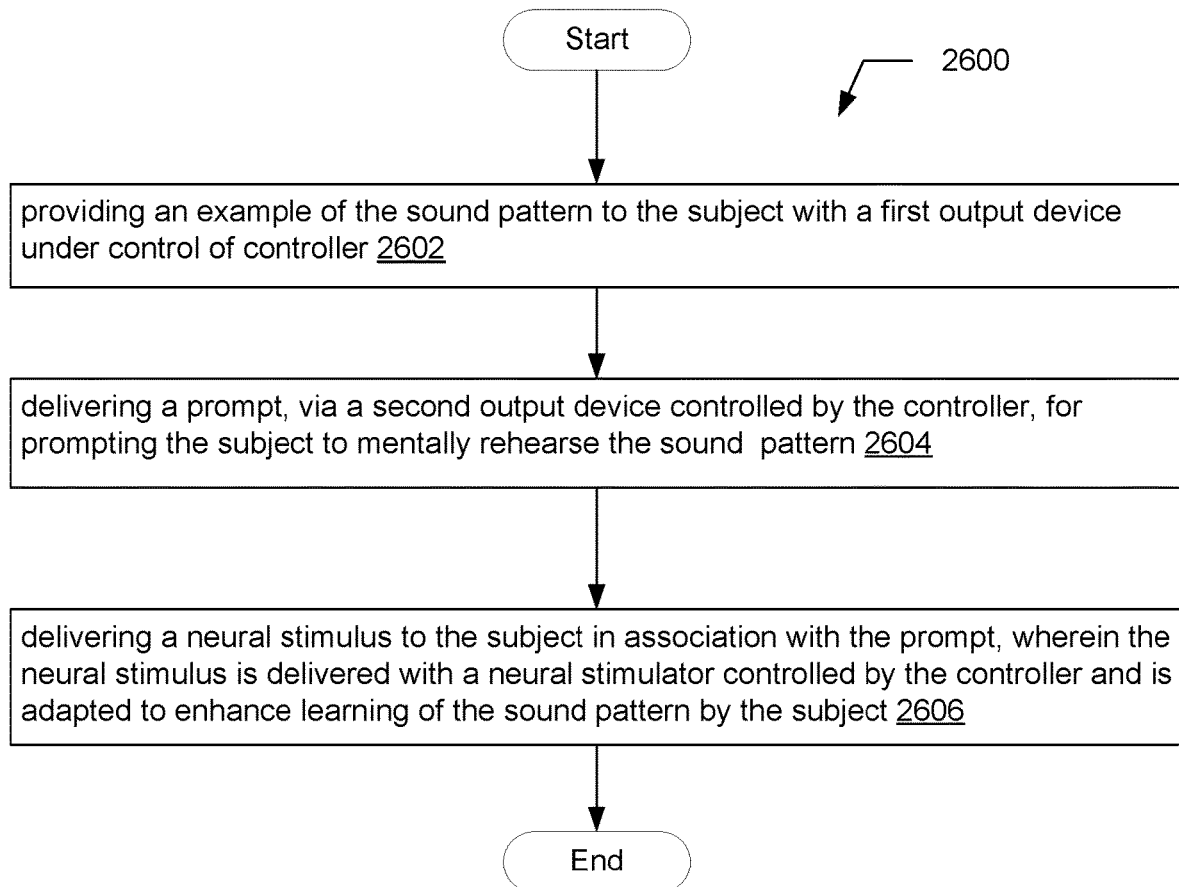
FIG. 26 is a block diagram of a method of enhancing learning of a sound pattern.

FIG. 26 is a flow diagram of enhancing learning of a sound pattern by a subject. Method 2600 includes providing an example of the sound pattern to the subject with a first output device under control of controller, at 2602; delivering a prompt, via a second output device controlled by the controller, for prompting the subject to mentally rehearse the sound pattern, at 2604; and delivering a neural stimulus to the subject in association with the prompt, wherein the neural stimulus is delivered with a neural stimulator controlled by the controller and is adapted to enhance learning of the sound pattern by the subject, at 2606.

Figure 27:
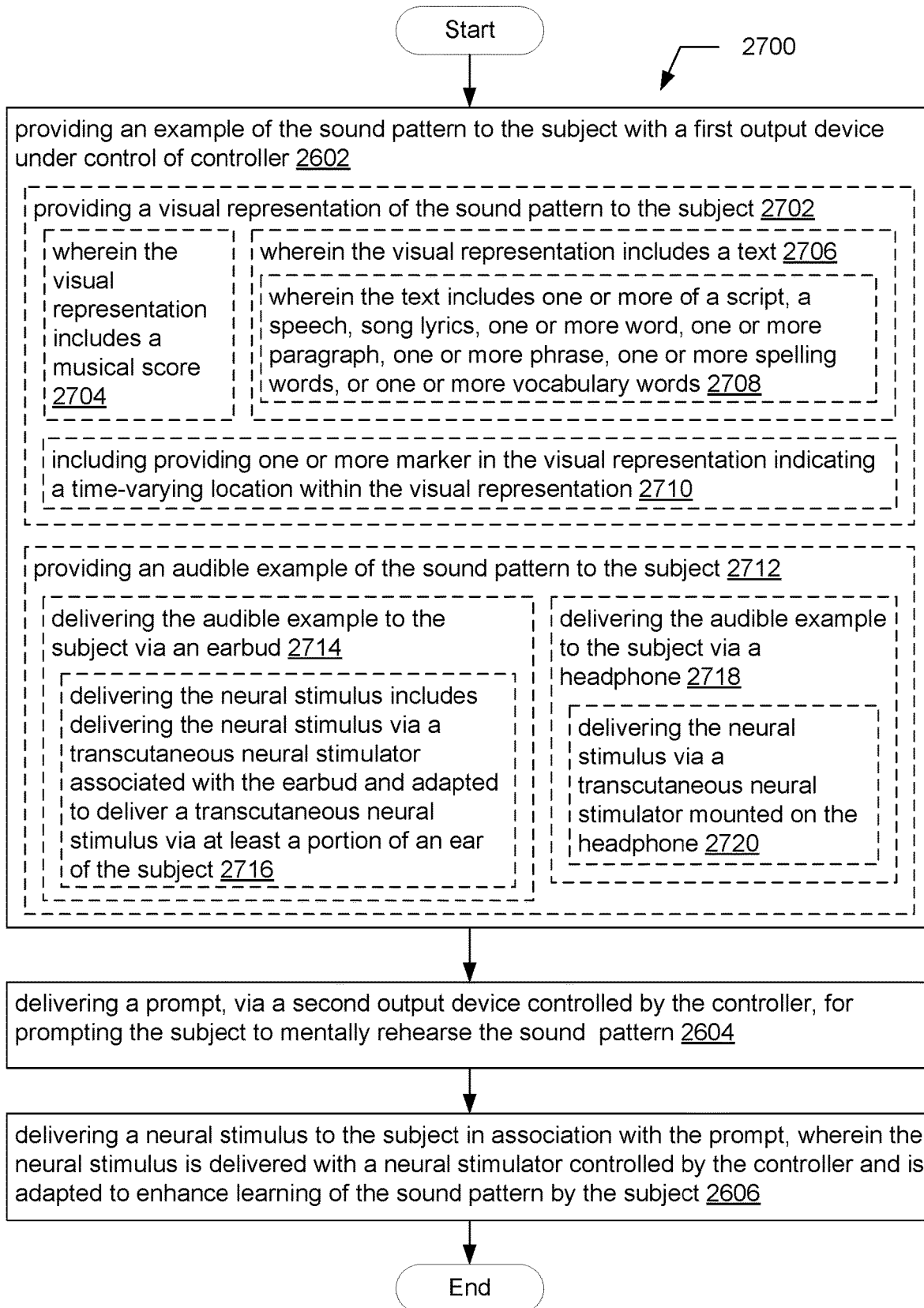
FIG. 27 is a flow diagram of a method.

FIG. 27 shows a method 2700 including further aspects relating to providing an example of the sound pattern to the subject with a first output device under control of controller, at 2602.

In an aspect, providing the example includes providing a visual representation of the sound pattern to the subject, at 2702. For example, the visual representation can include one or more of a musical score, as indicated at 2704, or a text, as indicated at 2706. In various aspects, the text includes one or more of a script, a speech, song lyrics, one or more word, one or more paragraph, one or more phrase, one or more spelling words, or one or more vocabulary words, as indicated at 2708. In an aspect, method 2700 also includes providing one or more marker in the visual representation indicating a time-varying location within the visual representation, as indicated at 2710.

In an aspect, providing the example includes providing an audible example of the sound pattern to the subject, at 2712. For example, providing the audible example includes delivering the audible example to the subject via an earbud, at 2714. In an aspect, delivering the neural stimulus includes delivering the neural stimulus via a transcutaneous neural stimulator associated with the earbud and adapted to deliver a transcutaneous neural stimulus via at least a portion of an ear of the subject, as indicated at 2716. In an aspect, providing the audible example includes delivering the audible example via a headphone, as indicated at 2718. In connection therewith, in an aspect delivering the neural stimulus includes delivering the neural stimulus via a transcutaneous neural stimulator mounted on the headphone, as indicated at 2720.

Figure 28:
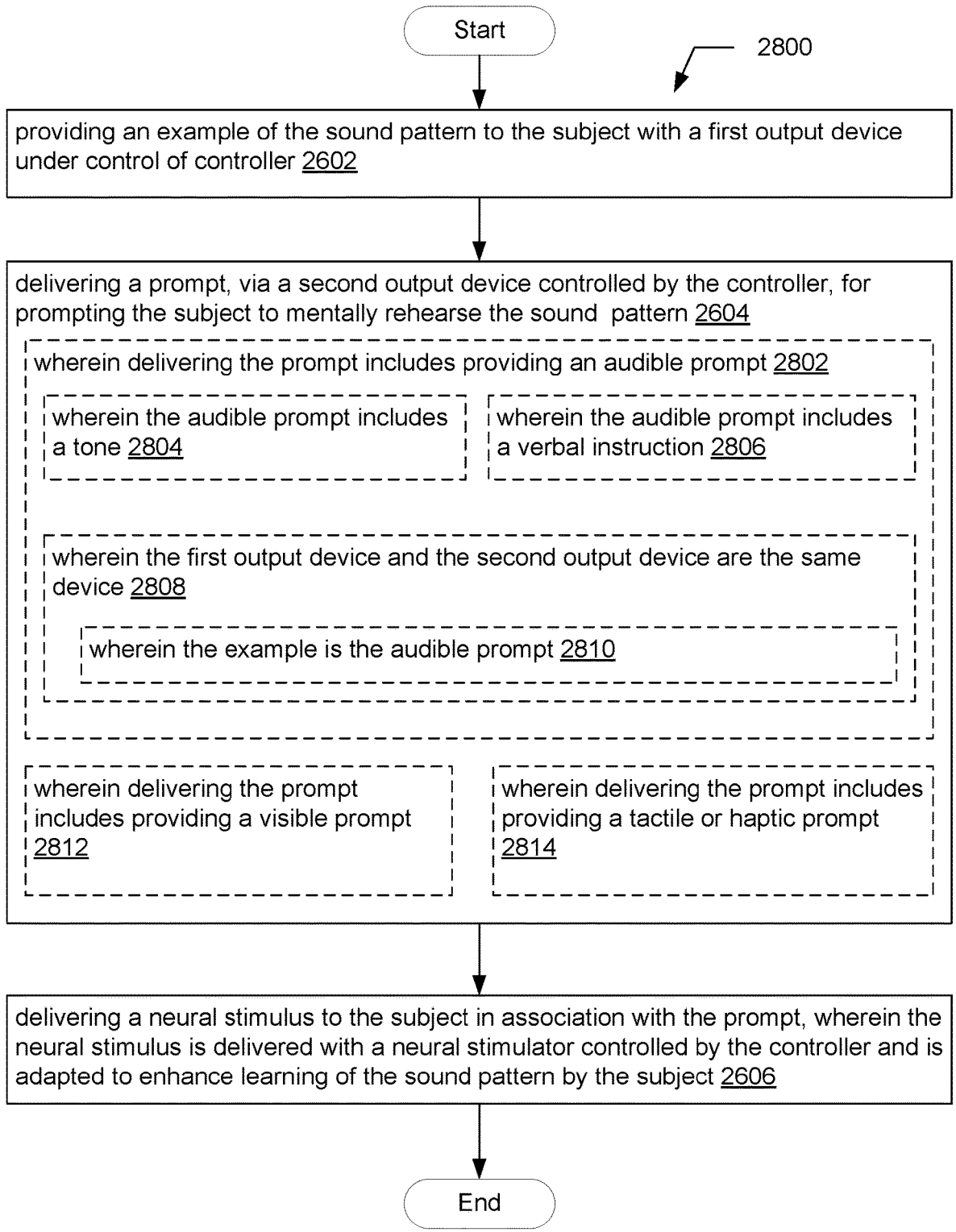
FIG. 28 is a flow diagram of a method.

FIG. 28 depicts a method 2800 illustrating various aspects relating to delivering a prompt, via a second output device controlled by the controller, for prompting the subject to mentally rehearse the sound pattern, at 2604. In an aspect, delivering the prompt includes providing an audible prompt, at 2802, which may include, for example, a tone, as indicated at 2804, or a verbal instruction, as indicated at 2806. In an aspect, the first output device and the second output device are the same device, as indicated at 2808. In an aspect, the example is the audible prompt, as indicated at 2810. In other aspects, delivering the prompt includes providing a visible prompt, as indicated at 2812, or providing a tactile or haptic prompt, as indicated at 2814.

Figure 29:
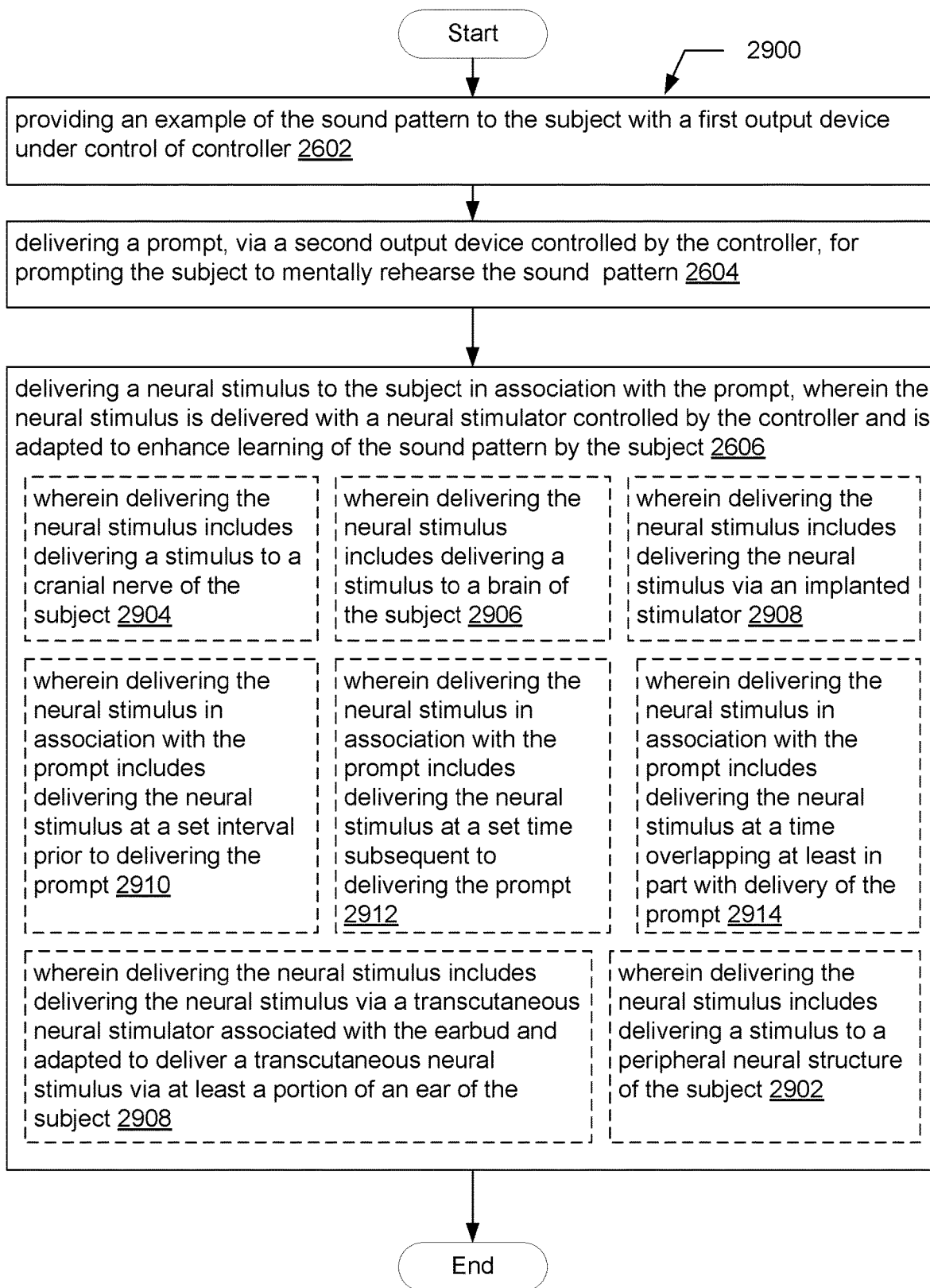
FIG. 29 is a flow diagram of a method.

FIG. 29 depicts a method 2900 illustrating variants of delivering a neural stimulus to the subject in association with the prompt, wherein the neural stimulus is delivered with a neural stimulator controlled by the controller and is adapted to enhance learning of the sound pattern by the subject at 2606. For example, in various aspects, delivering the neural stimulus includes one or more of delivering a stimulus to a peripheral neural structure of the subject, at 2902; delivering a stimulus to a cranial nerve of the subject, at 2904; or delivering a stimulus to a brain of the subject, at 2906. In an aspect, delivering the neural stimulus includes delivering the neural stimulus via an implanted stimulator, at 2908.

In various aspects, delivering the neural stimulus in association with the prompt includes delivering the neural stimulus at a set interval prior to delivering the prompt, as indicated at 2910; delivering the neural stimulus at a set time subsequent to delivering the prompt, as indicated at 2912; or delivering the neural stimulus at a time overlapping at least in part with delivery of the prompt, as indicated at 2914.

FIG. 30 depicts a method 3000 depicting other method aspects. For example, in an aspect, method 3000 includes retrieving data representing the example of the sound pattern from a data storage location associated with the controller, as indicated at 3002. In another aspect, method 3000 includes receiving data representing the example of the sound pattern from a remote location via a communication or computing network, as indicated at 3004. In various other aspects, method 3000 includes one or more of storing information relating to at least one of the example, the prompt, and the neural stimulus in a data storage location associated with the controller, as indicated at 3006; transmitting information relating to at least one of the example, the prompt, and the neural stimulus to a remote location via a communication or computing network, as indicated at 3008; and including receiving information relating to at least one of the example, the prompt, and the neural stimulus from the subject via a user input device, as indicated at 3010.

FIG. 31 depicts a computer program product 3100, including at least one non-transitory computer-readable medium 3102 bearing one or more instructions relating to a method a shown in FIG. 26. Non-transitory computer-readable medium 3102 bears one or more instructions for providing an example of the sound pattern to the subject with a first output device under control of controller; one or more instructions for delivering a prompt, via a second output device controlled by the controller, for prompting the subject to mentally rehearse the sound pattern; and one or more instructions for delivering a neural stimulus to the subj ect in association with the prompt, wherein the neural stimulus is delivered with a neural stimulator controlled by the controller and is adapted to enhance learning of the sound pattern by the subject, as indicated at 3104. In an aspect, non-transitory computer-readable medium 3102 is a recordable medium 3106, for example.

Figure 32:
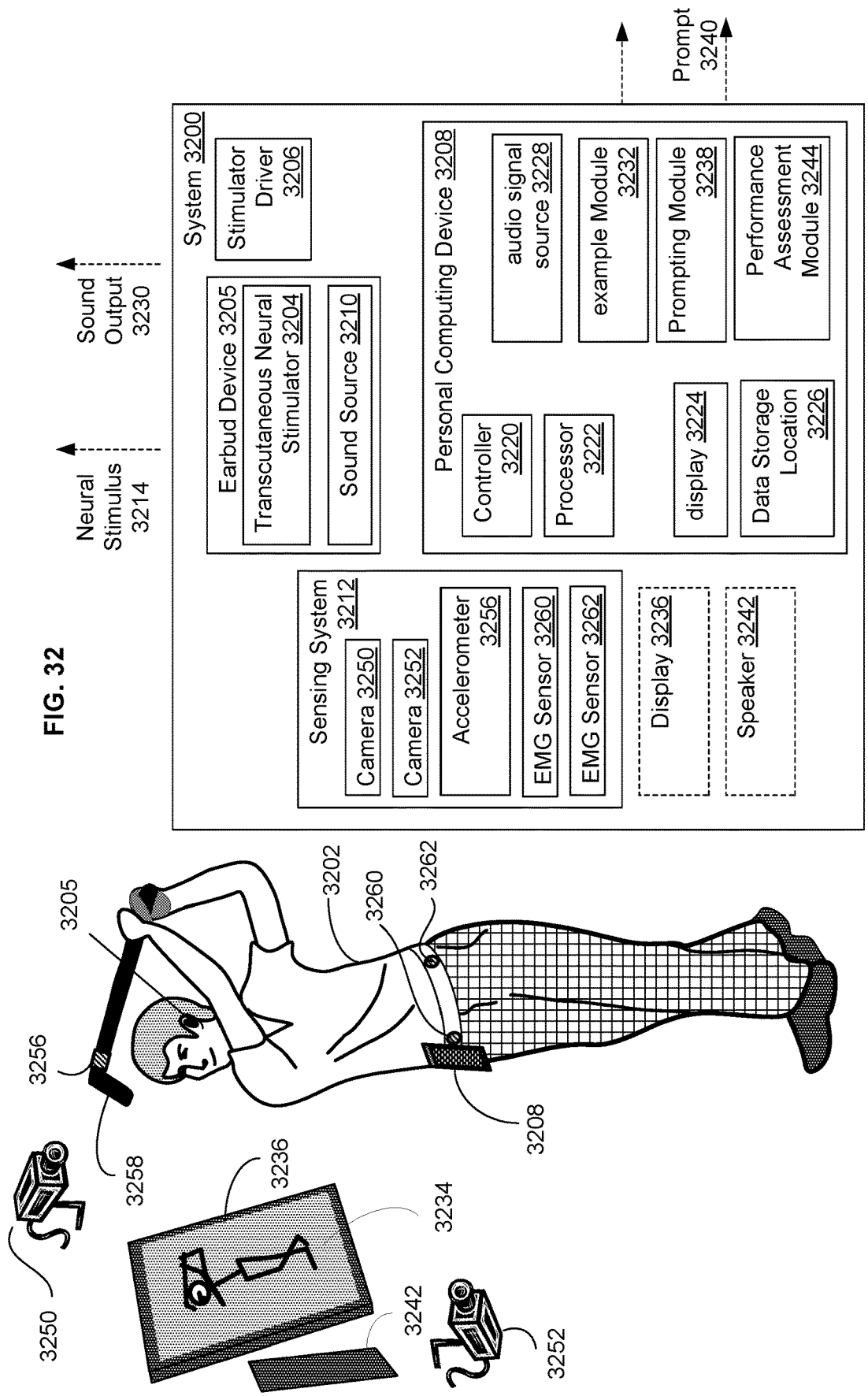
FIG. 32 is an illustration of a system for enhancing learning of a motor task.

FIG. 32 illustrates a system 3200 for enhancing learning of a motor task by a subject 3202. In the example of FIG. 32, the task learned by subject 3202 is a proper swing of a golf club. System 3200 includes a transcutaneous neural stimulator 3204 (in the form of an earbud device 3205) to deliver audible swing instructions in conjunction with transcutaneous stimulation of the vagus nerve to enhance learning. Although a single earbud is depicted in FIG. 32, it will be appreciated that the system typically includes a pair of earbuds such that audible instructions and transcutaneous stimulation can be delivered to both ears. System 3200 includes a stimulator driver 3206 used in combination with personal computing device 3208, a sound source 3210, and sensing system 3212. Transcutaneous neural stimulator 3204 is used for delivering a neural stimulus 3214 adapted to enhance learning of a motor task by subject 3202. Stimulator driver 3206 is adapted to drive delivery of neural stimulus 3214 by transcutaneous neural stimulator 3204. Sensing system 3212 is used for sensing at least one parameter indicative of performance of the motor task by subject 3202. Personal computing device 3208 includes controller 3220, processor 3222, display 3224, data storage location 3226, and audio signal source 3228, which is adapted to drive delivery of a sound output 3230 by sound source 3210. System 3200 includes microcircuitry and software to provide visual instruction, and feedback on performance, and to coordinate timing of swing prompts and nerve stimulation. In particular, example module 3232 is used for controlling delivery of an example 3234 of the motor task to subject 3202 via sound source 3210, display 3224, and one or more additional output device, here illustrated as display 3236. In addition, prompting module 3238 is used for driving delivery of a prompt 3240 via sound source 3210, display 3224, or an additional output device (such as speaker 3242 associated with display 3236), in association with delivery of neural stimulus 3214 by neural stimulator 3204, for prompting subject 3202 to perform the motor task. System 3200 also includes performance assessment module 3244 for processing the at least one parameter sensed by sensing system 3212.

In the example of FIG. 32, transcutaneous neural stimulator 3204 is a piezoelectric speaker (e.g., piezoelectric speakers are available from Digi-Key Corporation, Thief River Falls, Minn. 56701 USA) controlled by stimulator driver 3206 under control of controller 3220. Transcutaneous neural stimulator 3204 is located within the earbuds such that it can be positioned inside the tragus of the ear to provide stimulation to the auricular branch of the vagus nerve (see e.g., U.S. Pat. No. 7,797,042 issued to Dietrich et al. on Sep. 14, 2010 which is incorporated herein by reference). Sensing system 3212 includes remote cameras 3250, 3252 which provide feedback to system 3200, which analyzes the student's performance of the swing and the flight of the ball using performance assessment module 3242. Sensing system 3212 also includes accelerometer 3256 attached to the head of golf club 3258 to measure swing parameters. Sensing system 3212 also includes electromyographic (EMG) sensors 3260 and 3262 which are attached at either hip of subject 3202, contacting the skin, to monitor hip rotation and initiation of the downswing. EMG recording is timed to follow the swing prompts and EMG data is transmitted wirelessly to the learning system processors and processed to evaluate timing and movement during swing performance (see e.g., Buchanan et al., *J. Applied Biomechanics* 20: 367-395, 2004 which is incorporated by reference herein). Swing performance is evaluated by comparison of swing data to ideal swing parameters stored in data storage location 3226 and by analysis of golf ball flight path. System includes personal computing device 3208 (here, the subject's cell phone) to provide network access and inductive power to the earbud device. System 3200 orchestrates training sessions composed of multiple swing sets with instruction, feedback, cues and prompts. Stimulation of the vagus nerve is coordinately timed with the swing prompts to enhance learning of the evolving swing as the training session proceeds.

Subject 3202 begins a training session at a practice tee with the learning system earbuds 3205 inserted in his ear canals and with remote video cameras 3250 and 3252 directed at the practice tee from the rear and side. Accelerometer 3256 is attached to the head of golf club 3258, and system 3200 plays an introductory video which provides instructions, including a preview of the training session format, prompting, and feedback format and an example swing video, on display 3236 (alternatively, or in addition, the training video may be presented on display 3224 of personal computing device 3208). Example swing video provides example 3234, an illustration (in the form of a stick figure animation) of a good golf swing. The introductory video describes the audible prompts and replicate swing sets that will follow. Audible prompts are delivered by via sound source 3210 in earbud device 3205, or alternatively/in addition, via an additional output device, speaker 2340 associated with display 3236. For example, the swing elements are demonstrated, and a swing set of 5 replicate swings with an audible prompt for each swing is described. An example swing video is displayed and neural stimulation is initiated immediately afterward. Then, when prompted, the student takes a swing at a golf ball and repeats the procedure for 4 additional swings. After the first swing set, the enhanced learning system analyzes the swing performance data from the video cameras, the accelerometer and EMG sensors by comparison to ideal swing data for a golfer of similar height, weight and skill level (e.g., recreational). The system provides feedback to the student in an updated instructional video. For example, the feedback may emphasize the speed of the backswing (the student's backswing may be too fast) or the plane of the downswing (too steep or too shallow) and provide corrective actions. The system then prompts the student to hit a second swing set, comprised of 5 replicate swings. The second swing set may be accompanied by transcutaneous neural stimulation from the piezoelectric speakers located in the earbuds. However, neural stimulation may be contingent on swing performance. For example, if swing performance is below threshold levels relative to the example swing data then neural stimulation may be withheld until improved performance is detected. Data from the second swing set is compared to the example swing parameters stored in memory and also to the previous swing set. An updated video provides feedback and instructions to the student on their recent swing performance, including any corrective actions to be taken in the next swing set, for example, slowing the backswing, starting hip rotation earlier, or readjusting the backswing plane. A third swing set, consisting of 5 swings is prompted by the learning system and accompanied by neural stimulation from the piezoelectric speakers if swing performance has improved.

The swing data for the training session is analyzed by performance assessment module 3242 in system 3200, and feedback is provided to the student as an instructional video which critiques the swing performance and reinforces progress in achieving improved swing parameters (e.g., swing velocity). Additional swing sets may be taught by the learning system to further improve the student's swing performance with repetition and neural stimulation. A final video at the end of the training session reports progress in improving swing performance parameters. The system may send the feedback videos and the training session video to an instructor and the student, via mobile network access by personal computing device 3208. Swing data is stored on a network computer, locally or remotely, and may be recalled for review prior to another training session or to establish the swing parameters and focus areas for a new training session. The learning system may reward the student with an audio message or a favorite song when an increased number of swing parameters are performed at a particular skill level, e.g., recreational golfer.

Although in the example shown in FIG. 32, system 3200 is used for training subject 3202 in a golf swing, such a system may be used for training a subject to perform various types of motor tasks, which may be related to sports, recreational activities, job-related activities, performing arts, or activities of daily life. Sensing system 3212 may include various types of sensors, not limited to those depicted in FIG. 32, depending upon the type of motor task to be performed. Sensors may be attachable to the subject, e.g. dry electrodes, epidermal electronics, adherent accelerometers, or cameras; built into or attached to a wearable item (such as a garment, an item of clothing, an item of headwear, an item of jewelry, a wristband, a headband, a belt, a harness, an item of footwear, an eyeglass, a goggle, or a helmet), or located in or on an item of athletic equipment. In various aspects, a sensing system includes one or more accelerometer, inclinometer, force sensor, pressure sensor, motion sensor, temperature sensor, optical sensor, or EMG sensor. In various aspects, the sensing system includes one or more remote sensor, such as a camera, a scanner, and a Kinect. In an aspect, sensing system 3212 includes a plurality of sensors (various examples of which are described in connection with FIG. 2) adapted to sense a plurality of parameters indicative of performance of the motor task by subject 3202, and performance assessment module 3242 is configured to process the plurality of parameters to assess performance of the motor task by the subject.

Example module 3232 can be configured to control delivery of the example of the motor task via one or more of sound source 3210, speaker 3240, display 3236 or display 3224. The example can be an audiovisual example that includes both video and sound track (e.g., narration of actions to be performed), or the example can include only audio or only video. In some aspects, the example can be delivered via other types of output devices, for example, a controllable compression garment, an electrical stimulation device, a force applying device, a vibrotactile device, or a haptic device. Examples of garments and other wearable items including capability for sensing and delivery of stimuli, compression, etc. are described in U.S. Published Patent Application 20160058644 to Cheatham, III et al.; U.S. Published Patent Application 20160015280 to Hyde et al.; U.S. Published Patent Application 20160015972 to Hyde et al.; U.S. Published Patent Application 20160120733 to Ishikawa et al.; U.S. Published Patent Application 20160120734 to Ishikawa et al.; and U.S. Published Patent Application 20160220808 to Hyde et al., all of which are incorporated herein by reference. Such devices can be used to move the subject's body, or cause the subject to move his body, so as to a produce a desired pattern of movement. Similarly, such devices can be used to deliver prompts as well as examples to the subject.

Stimulator driver 3206 can be configured to drive delivery of the neural stimulus 3214 responsive to an output of the performance assessment module 3242 based at least in part on a comparison of the at least one parameter with at least one target parameter. For example, in an aspect, the at least one target parameter corresponds to a preferred task performance. In an aspect, a selection module (like selection module 418 in FIG. 3) is adapted to compare parameters corresponding to two or more historical performances of the task by the subject and select at least one parameter corresponding to at least one best performance of the two or more historical performances, wherein the preferred task performance is the at least one best performance. In an aspect, the selection module is adapted to compare two or more portions of two or more historical performances of the task by the subject, select the best two or more portions of the two or more historical performances, and combine the best two or more portions to produce a best combined historical performance. In an aspect, sensing system 3212 is adapted to sense a plurality of parameters indicative of performance of the motor task by the subject, and the performance assessment module 3242 is configured to compare the plurality of parameters with a plurality of target parameters. In connection therewith, stimulator driver 3206 is configured to drive delivery of neural stimulus 3214 responsive to an output of the performance assessment module 3242 based at least in part on a comparison of the plurality of parameters with the plurality of target parameters.

Figure 33:
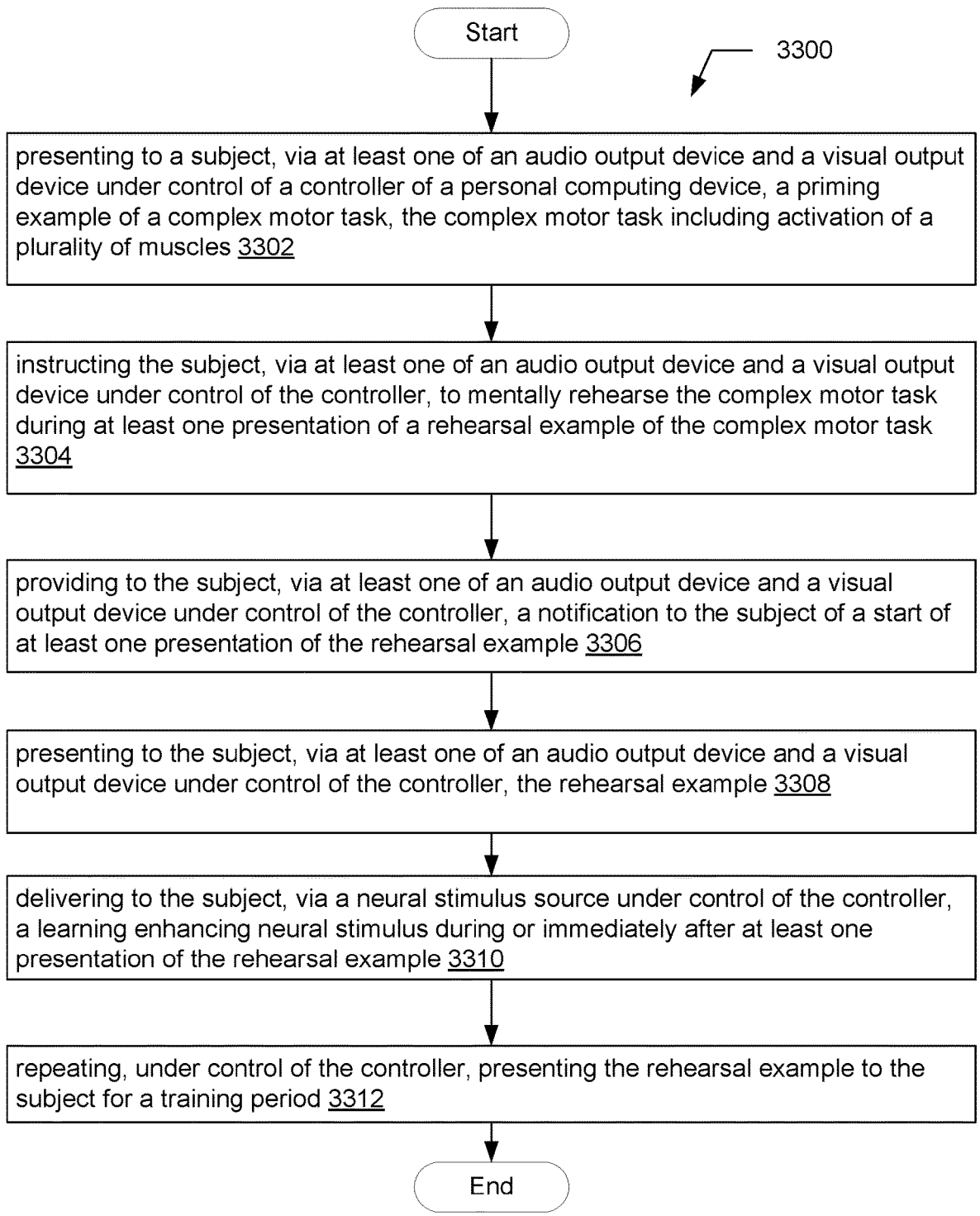
FIG. 33 is a flow diagram of a method of training a subject to perform a complex motor task.

FIG. 33 is a flow diagram of a method of training a subject to perform a complex motor task. Method 3300 includes presenting to a subject, via at least one of an audio output device and a visual output device under control of a controller of a personal computing device, a priming example of a complex motor task, the complex motor task including activation of a plurality of muscles, as indicated at 3302; instructing the subject, via at least one of an audio output device and a visual output device under control of the controller, to mentally rehearse the complex motor task during at least one presentation of a rehearsal example of the complex motor task, as indicated at 3304; providing to the subject, via at least one of an audio output device and a visual output device under control of the controller, a notification to the subject of a start of at least one presentation of the rehearsal example, as indicated at 3306; presenting to the subject, via at least one of an audio output device and a visual output device under control of the controller, the rehearsal example, as indicated at 3308; delivering to the subject, via a neural stimulus source under control of the controller, a learning enhancing neural stimulus during or immediately after at least one presentation of the rehearsal example, as indicated at 3310; and repeating, under control of the controller, presenting the rehearsal example to the subject for a training period, as indicated at 3312.

Figure 34:
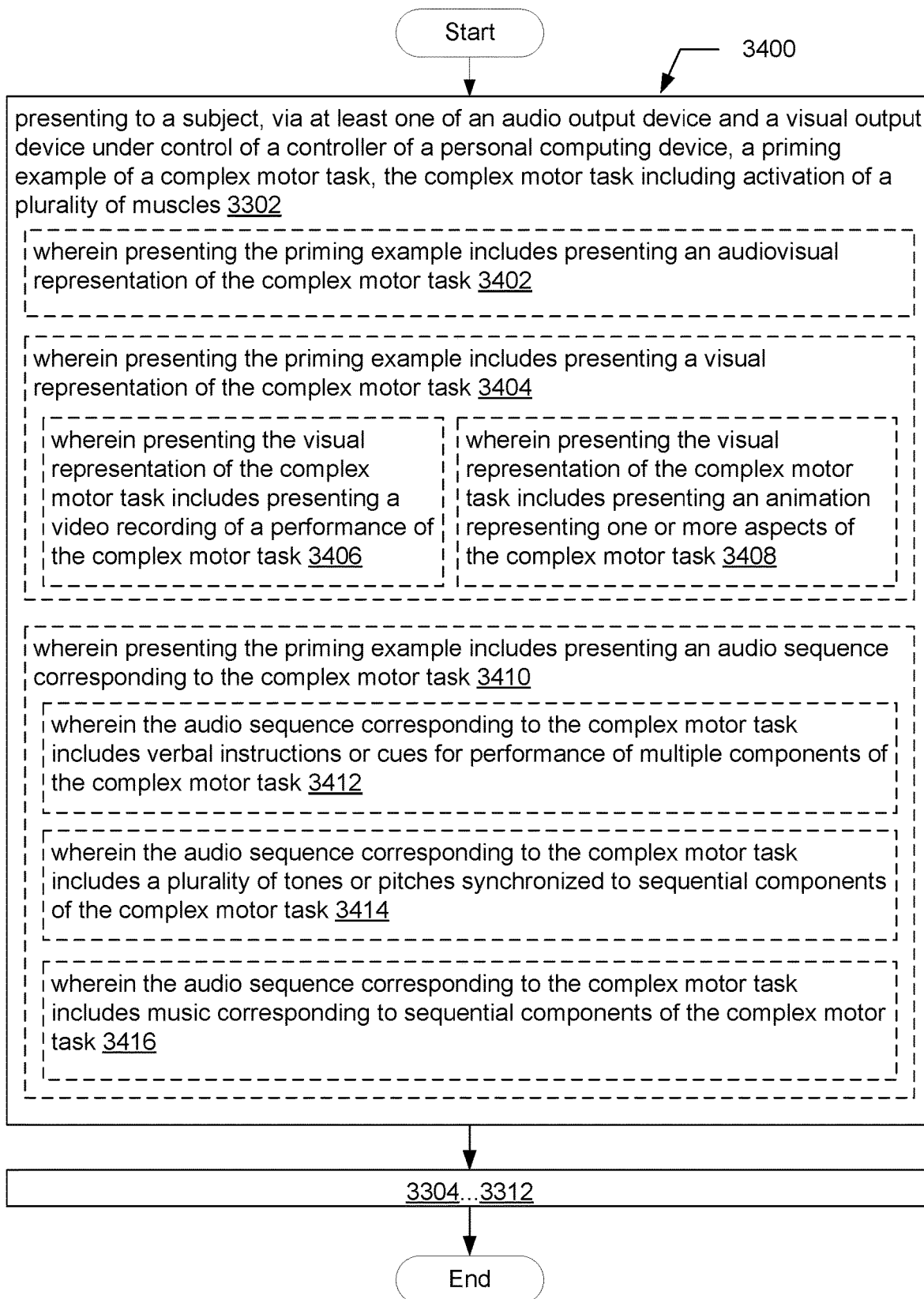
FIG. 34 is a flow diagram of a method.

FIG. 34 depicts a method 3400, including further aspects relating to presenting the priming example to the subject. In one aspect, presenting the priming example includes presenting an audiovisual representation of the complex motor task, as indicated at 3402. In another aspect, presenting the priming example includes presenting a visual representation of the complex motor task, as indicated at 3404. For example, in an aspect, presenting the visual representation of the complex motor task includes presenting a video recording of a performance of the complex motor task, as indicated at 3406. In another aspect, wherein presenting the visual representation of the complex motor task includes presenting an animation representing one or more aspects of the complex motor task, as indicated at 3408.

In yet another aspect, presenting the priming example includes presenting an audio sequence corresponding to the complex motor task, as indicated at 3410, wherein the audio sequence corresponding to the complex motor task includes, for example, verbal instructions or cues for performance of multiple components of multiple components of the complex motor task, as indicated at 3412; a plurality of tones or pitches synchronized to sequential components of the complex motor task, as indicated at 3414, or music corresponding to sequential components of the complex motor task, as indicated at 3416.

Figure 35:
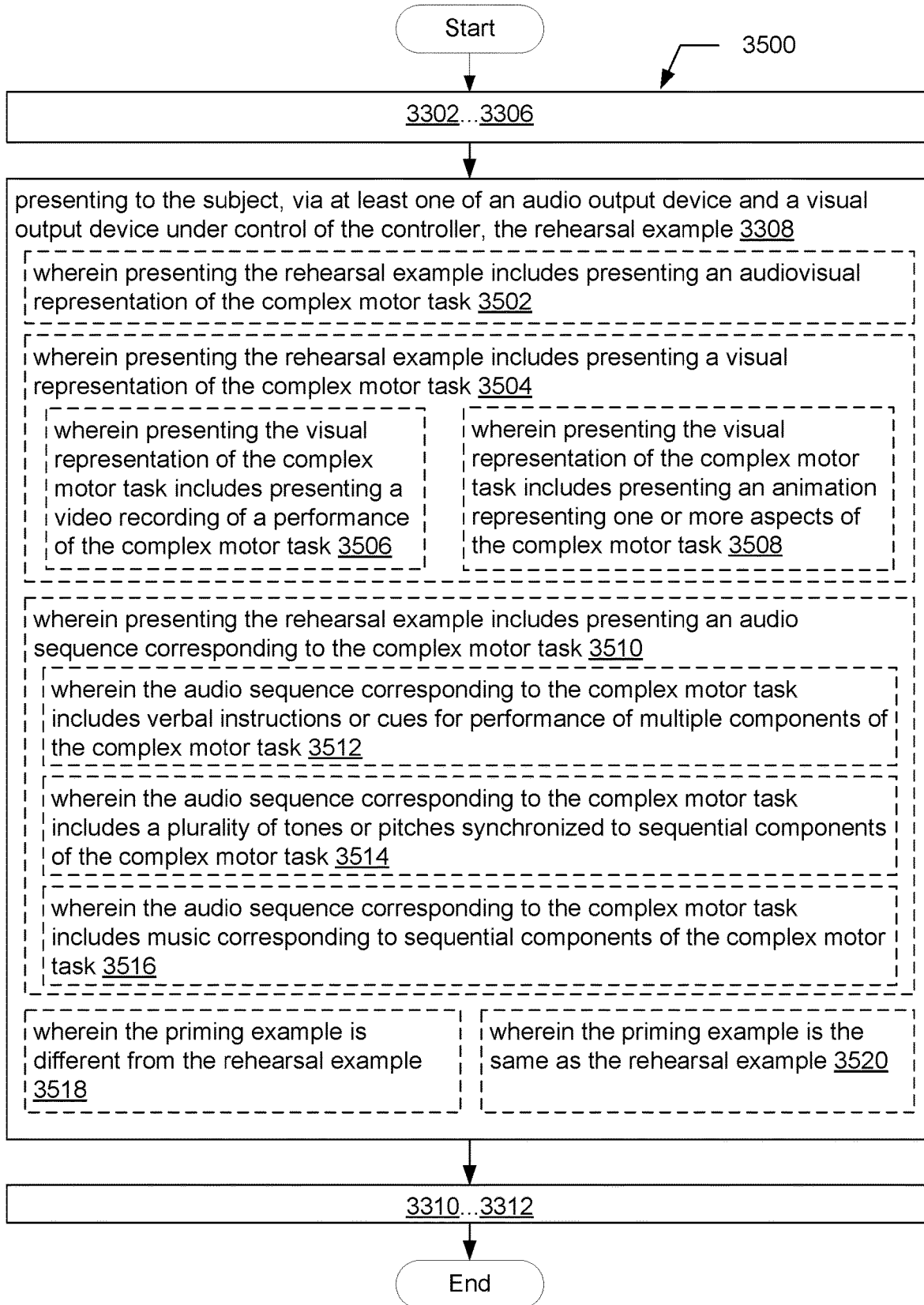
FIG. 35 is a flow diagram of a method.

FIG. 35 depicts a method 3500, including further details relating to presenting the rehearsal example to the subject. In one aspect, presenting the rehearsal example includes presenting an audiovisual representation of the complex motor task, as indicated at 3502. In another aspect, presenting the rehearsal example includes presenting a visual representation of the complex motor task, as indicated at 3504, e.g. a video recording of a performance of the complex motor task, as indicated at 3506, or an animation representing one or more aspects of the complex motor task, as indicated at 3508.

In another aspect, presenting the rehearsal example includes presenting an audio sequence corresponding to the complex motor task, as indicated at 3510. For example, in various aspects, the audio sequence corresponding to the complex motor task includes verbal instructions or cues for performance of multiple components of the complex motor task, as indicated at 3512; a plurality of tones or pitches synchronized to sequential components of the complex motor task, as indicated at 3514; or music corresponding to sequential components of the complex motor task, as indicated at 3516. The priming example can be different from the rehearsal example, as indicated at 3518, or the same as the rehearsal example, as indicated at 3520.

Figure 36:
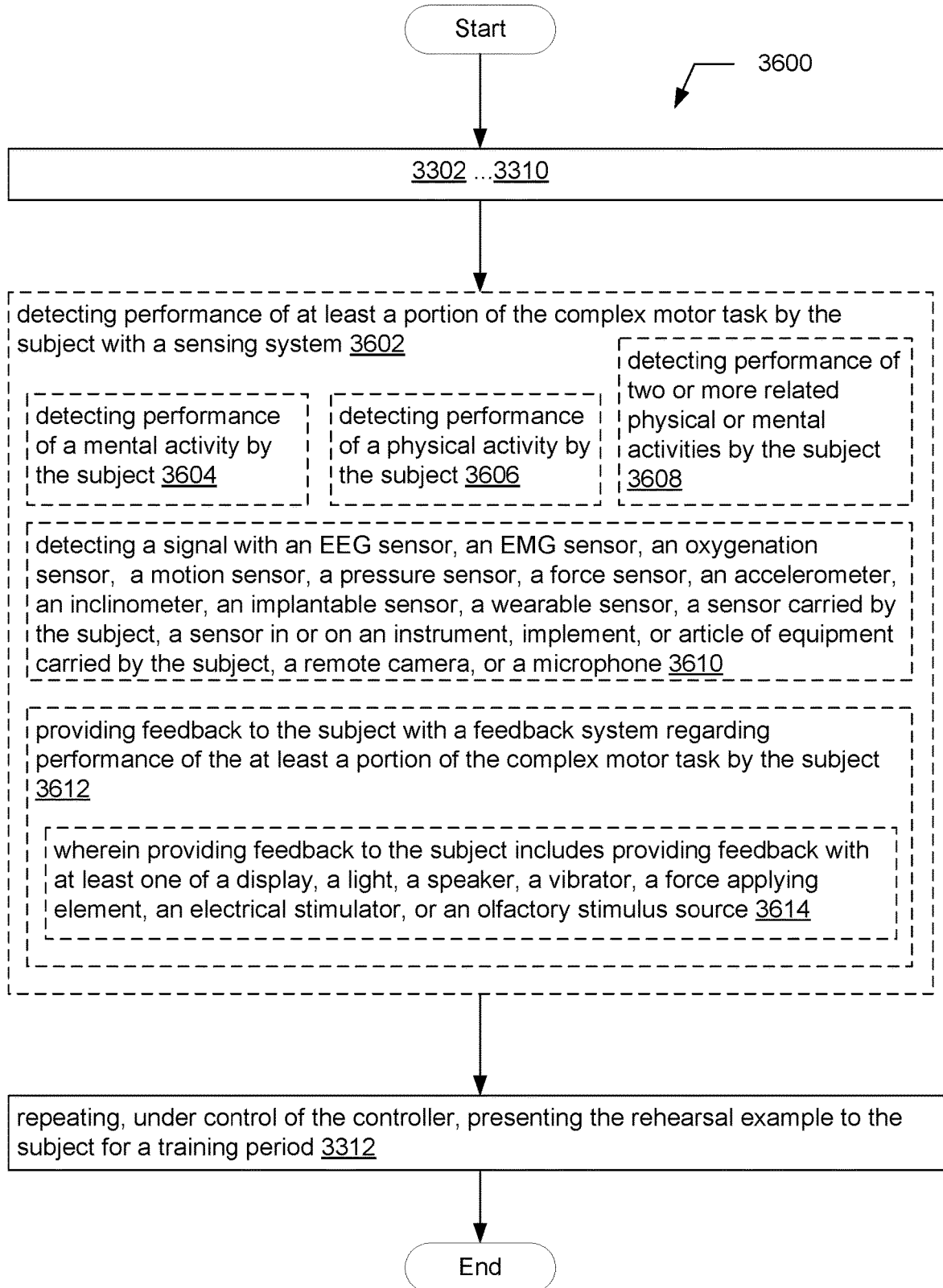
FIG. 36 is a flow diagram of a method.

FIG. 36 depicts method 3600, which includes detecting performance of at least a portion of the complex motor task by the subject with a sensing system, as indicated at 3602. In various aspects, detecting performance of the at least a portion of the complex motor task includes one or more of detecting performance of a mental activity by the subject, at 3604; detecting performance of a physical activity by the subject, at 3606; detecting performance of two or more related physical or mental activities by the subject, at 3608; and detecting a signal with an EEG sensor, an EMG sensor, a motion sensor, a pressure sensor, a force sensor, an accelerometer, an inclinometer, an implantable sensor, a wearable sensor, a sensor carried by the subject, a sensor in or on an instrument, implement, or article of equipment carried by the subject, a remote camera, or a microphone, at 3610.

In an aspect, method 3600 further includes providing feedback to the subject with a feedback system regarding performance of the at least a portion of the complex motor task by the subject, at 3612. For example, in various aspects, providing feedback to the subject includes providing feedback with at least one of a display, a light, a speaker, a vibrator, a force applying element, an electrical stimulator, or an olfactory stimulus source, at 3614.

Figure 37:
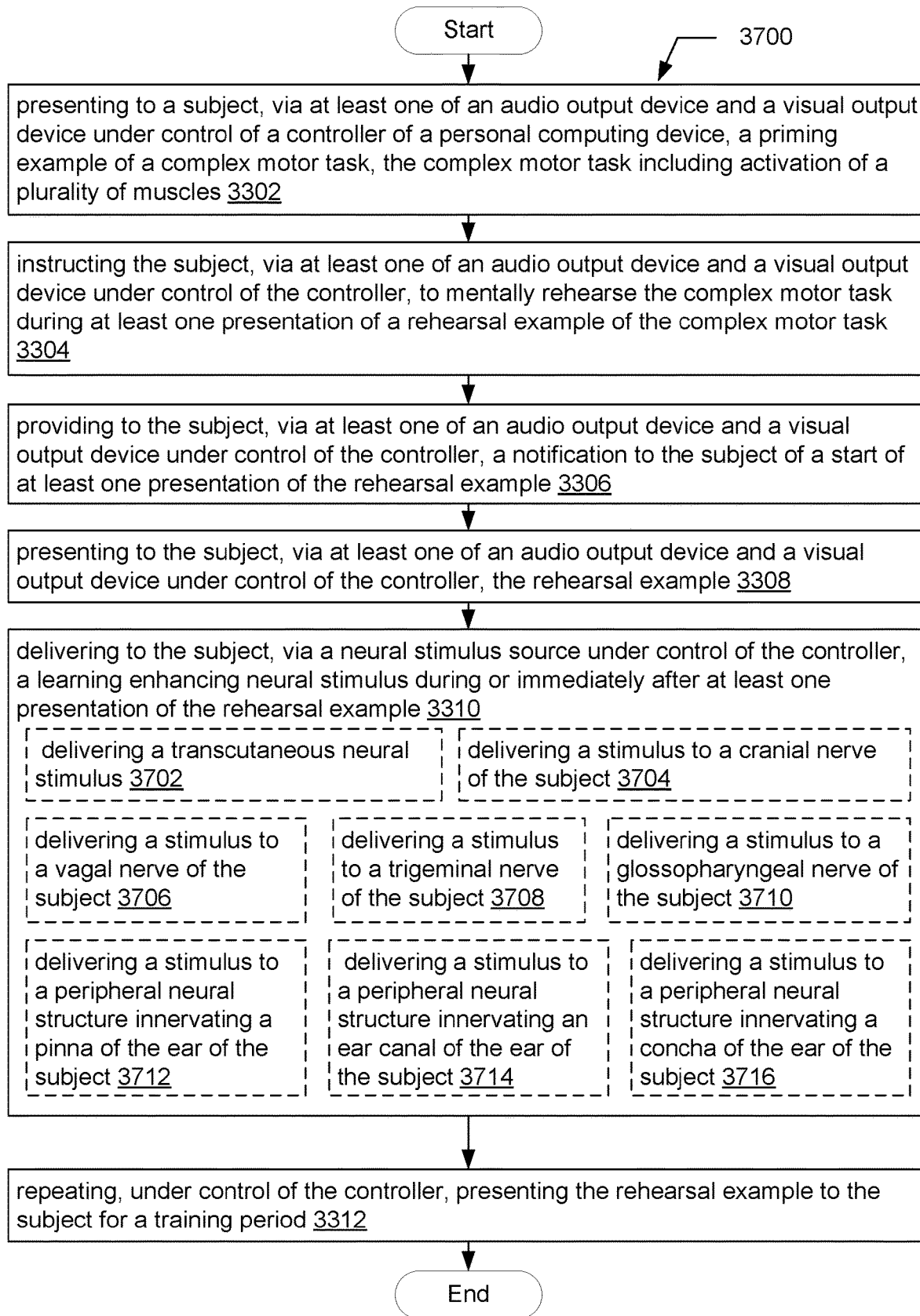
FIG. 37 is a flow diagram of a method.

FIG. 37 depicts method 3700, which includes further aspects relating delivery of the learning enhancing stimulus. In an aspect, delivering the learning enhancing neural stimulus includes delivering a transcutaneous neural stimulus, at 3702. In various aspects, delivering the learning enhancing neural stimulus includes delivering a stimulus to a cranial nerve of the subject, at 3704; a vagal nerve of the subject, at 3706; a trigeminal nerve of the subject, at 3708; or a glossopharyngeal nerve of the subject, at 3710. For example, delivering the learning enhancing neural stimulus includes delivering a stimulus to a peripheral neural structure innervating a pinna of the ear of the subject, at 3712; an ear canal of the ear of the subject, at 3714; or a concha of the ear of the subject, at 3716.

Figure 38:
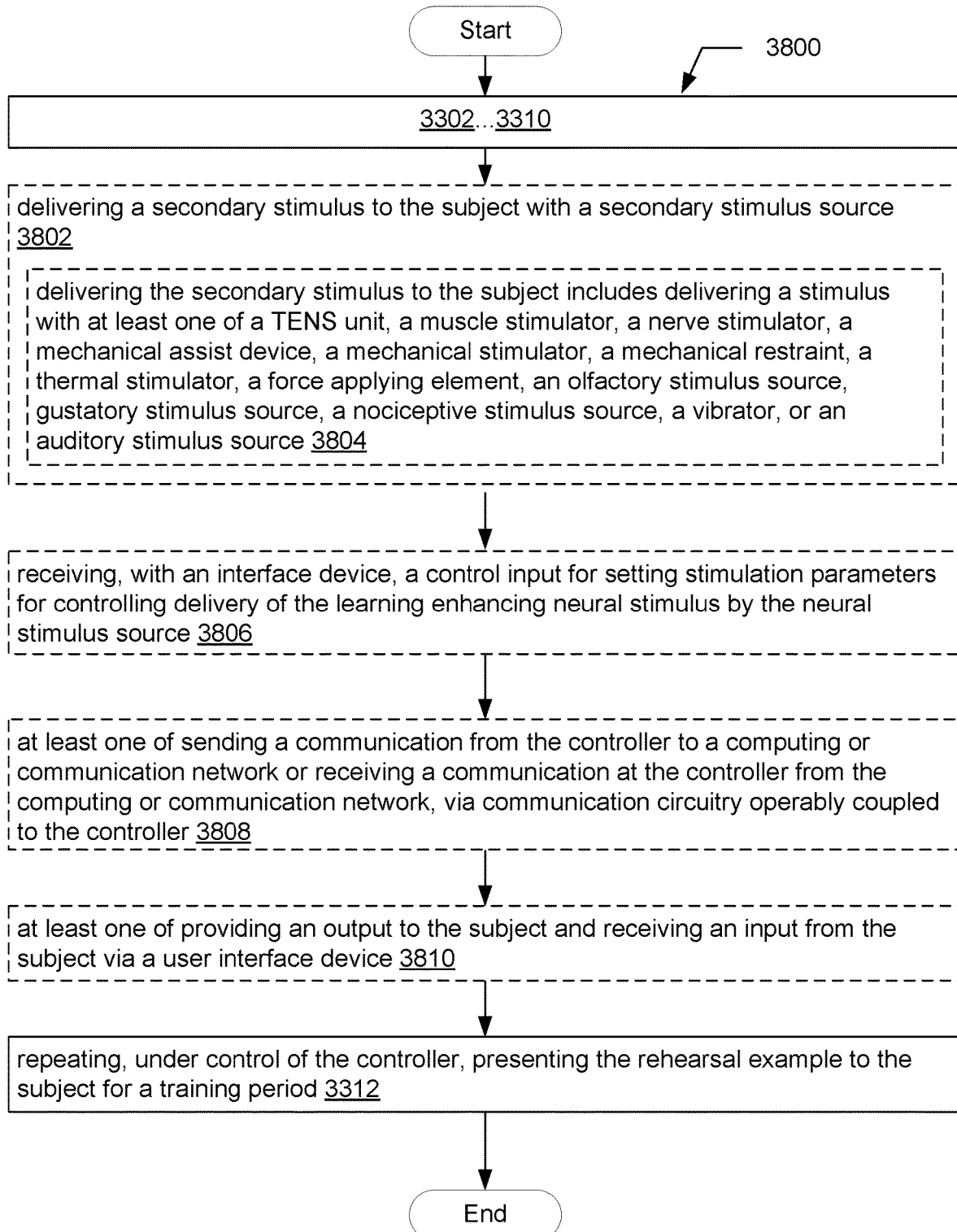
FIG. 38 is a flow diagram of a method.

FIG. 38 depicts method 3800, which includes additional method variations. In an aspect, method 3800 includes delivering a secondary stimulus to the subject with a secondary stimulus source, at 3802, e.g. delivering a stimulus with at least one of a TENS unit, a muscle stimulator, a nerve stimulator, a mechanical assist device, a mechanical stimulator, a mechanical restraint, a thermal stimulator, a force applying element, an olfactory stimulus source, gustatory stimulus source, a nociceptive stimulus source, a vibrator, or an auditory stimulus source, as indicated at 3804.

In another aspect, method 3800 includes receiving, with an interface device, a control input for setting stimulation parameters for controlling delivery of the learning enhancing neural stimulus by the neural stimulus source, at 3806. In other aspects, method 3800 includes at least one of sending a communication from the controller to a computing or communication network or receiving a communication at the controller from the computing or communication network, via communication circuitry operably coupled to the controller, at 3808. In still other aspects, method 3800 includes at least one of providing an output to the subject and receiving an input from the subject via a user interface device, at 3810.

Figure 39:
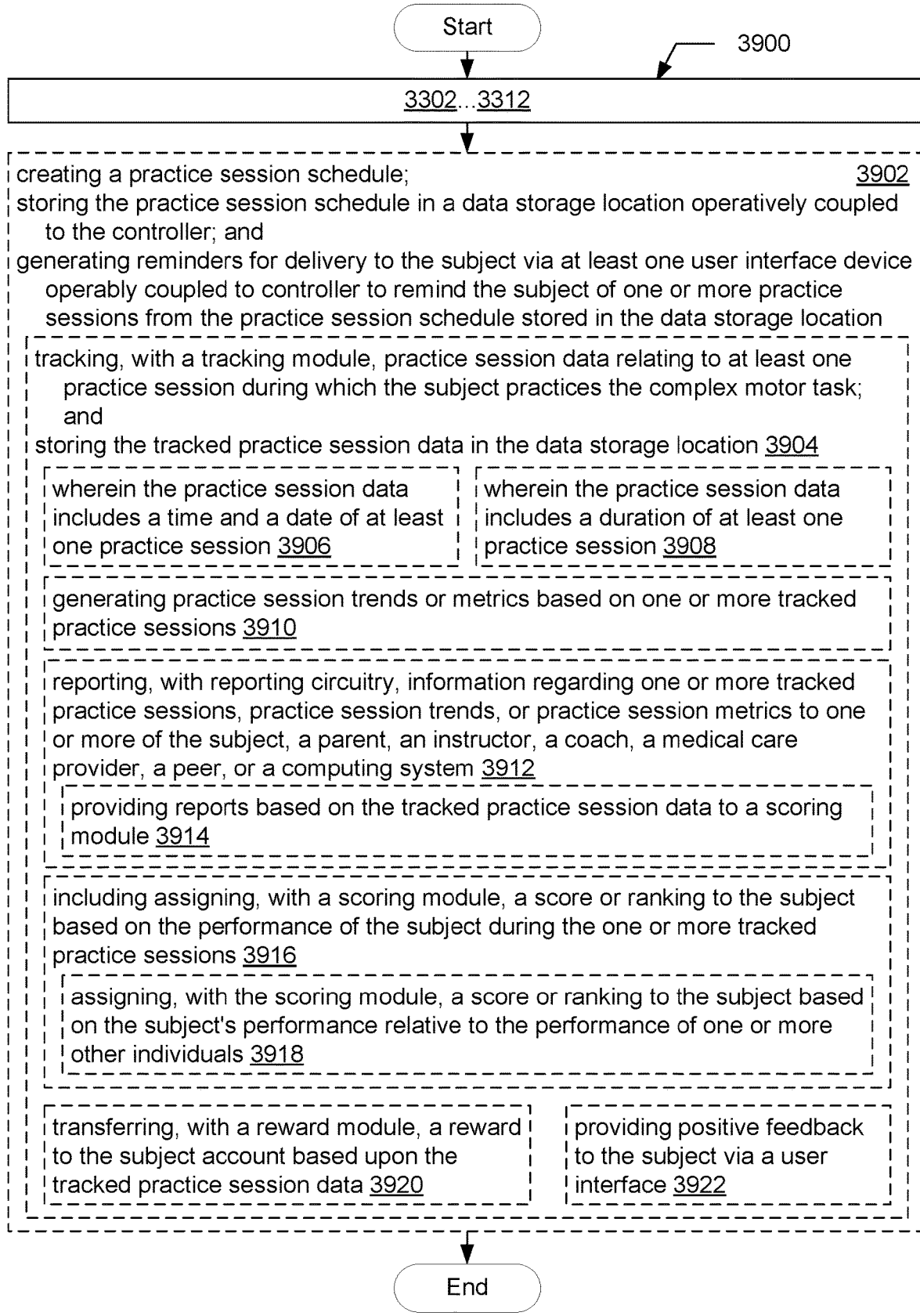
FIG. 39 is a flow diagram of a method.

FIG. 39 depicts method 3900 including various method aspects relating to scheduling and tracking of practices sessions. In an aspect, method 3900 includes creating a practice session schedule; storing the practice session schedule in a data storage location operatively coupled to the controller; and generating reminders for delivery to the subject via at least one user interface device operably coupled to controller to remind the subject of one or more practice sessions from the practice session schedule stored in the data storage location, as indicated at 3902. In a further aspect, method 3900 includes tracking, with a tracking module, practice session data relating to at least one practice session during which the subject practices the complex motor task; and storing the tracked practice session data in the data storage location, as indicated at 3904. In an aspect, the practice session data includes a time and a date of at least one practice session, as indicated at 3906, or a duration of at least one practice session, as indicated at 3908.

In other aspects, method 3900 includes one or more of generating practice session trends or metrics based on one or more tracked practice sessions, as indicated at 3910, and reporting, with reporting circuitry, information regarding one or more tracked practice sessions, practice session trends, or practice session metrics to one or more of the subject, a parent, an instructor, a coach, a medical care provider, or a peer, as indicated at 3912. For example, reporting with the reporting circuitry includes providing reports based on the tracked practice session data to a scoring module, as indicated at 3914.

In an aspect, method 3900 includes assigning, with a scoring module, a score or ranking to the subject based on the performance of the subject during the one or more tracked practice sessions, at 3916. This may include, for example, assigning, with the scoring module, a score or ranking to subject based on subject's performance relative to the performance of one or more other individuals, at 3918.

In some aspects, method 3900 includes transferring, with a reward module, a reward to the subject account based upon the tracked practice session data, at 3920, and/or providing positive feedback to the subject via a user interface, at 3922.

FIG. 40 depicts method 4000, which includes sensing, with an attention sensor, at least one parameter indicative of attentiveness of the subject, at 4002. For example, sensing the at least one parameter indicative of attentiveness of the subject includes sensing a signal with at least one of an EEG sensor, at 4004; an eye tracking sensor, at 4006; an EMG sensor, at 4008; a motion sensor, at 4010; a force sensor, at 4012; a pressure sensor, at 4014; an accelerometer, at 4016; a wearable sensor 4018; a remote sensor, 4020; and a camera 4022.

In addition, in a further aspect, method 4000 includes determining, with an attention tracking module operatively connected to the attention sensor, attentiveness of the subject based on the at least one parameter indicative of attentiveness of the subject, as indicated at 4024. In addition, method 4000 may include generating a notification if the subject is not attentive, at 4026, for example including generating one or more of an audio alarm tone, a verbal notification, a visible notification, a tactile notification, an electronic notification for storage in a data storage location or an electronic notification for transmission to at least one additional location, as indicated at 4028.

FIG. 41 shows a computer program product 4100, including at least one non-transitory computer-readable medium 4102 bearing one or more instructions relating to a method as shown in FIG. 33. Non-transitory computer-readable medium 4102 bears one or more instructions for presenting to a subject, via at least one of an audio output device and a visual output device under control of a controller of a personal computing device, a priming example of a complex motor task, the complex motor task including activation of a plurality of muscles; one or more instructions for instructing the subject, via at least one of an audio output device and a visual output device under control of the controller, to mentally rehearse the complex motor task during at least one presentation of a rehearsal example of the complex motor task; one or more instructions for providing to the subject, via at least one of an audio output device and a visual output device under control of the controller, a notification to the subject of a start of at least one presentation of the rehearsal example; one or more instructions for presenting to the subject, via at least one of an audio output device and a visual output device under control of the controller, the rehearsal example; one or more instructions for delivering to the subject, via a neural stimulus source under control of the controller, a learning enhancing neural stimulus during or immediately after at least one presentation of the rehearsal example; and one or more instructions for repeating, under control of the controller, presenting the rehearsal example to the subject for a training period, as indicated at 4104. Non-transitory computer-readable medium may be, for example, a recordable medium 4106.

For example, in some aspects, non-transitory computer-readable medium 4102 bears one or more instructions for creating a practice session schedule; one or more instructions for storing the practice session schedule in a data storage location operatively coupled to the controller; and one or more instructions for generating reminders for delivery to the subject via at least one user interface device operably coupled to controller to remind the subject of one or more practice sessions from the practice session schedule stored in the data storage location, corresponding to aspects of method 3900 in FIG. 39.

In some aspects, non-transitory computer-readable medium 4102 bears one or more instructions for tracking, with a tracking module, practice session data relating to at least one practice session during which the subject practices the complex motor task; and one or more instructions for storing the tracked practice session data in a data storage location, also corresponding to aspects of method 3900 in FIG. 39.

In other aspects, non-transitory computer-readable medium 4102 bears instructions pertaining to various of the method steps depicted in FIGS. 33-40.

In a general sense, the various embodiments described herein can be implemented, individually and/or collectively, by various types of electrical circuitry having a wide range of electrical components such as hardware, software, firmware, and/or virtually any combination thereof. Electrical circuitry (including electrical control circuitry 208 in FIGS. 2 and 3, for example) includes electrical circuitry having at least one discrete electrical circuit, electrical circuitry having at least one integrated circuit, electrical circuitry having at least one application specific integrated circuit, electrical circuitry forming a computing device configured by a computer program (e.g., a computer configured by a computer program which at least partially carries out processes and/or devices described herein, or a microprocessor configured by a computer program which at least partially carries out processes and/or devices described herein), electrical circuitry forming a memory device (e.g. data storage location 244 in FIG. 3), which may include various types of memory (e.g., random access, flash, read only, etc.)), electrical circuitry forming a communications device (e.g., communication circuitry 430 in FIG. 3) (e.g., a modem, communications switch, optical-electrical equipment, etc.), and/or any non-electrical analog thereto, such as optical or other analogs (e.g., graphene based circuitry). In an embodiment, the system is integrated in such a manner that the system operates as a unique system configured specifically for function of the neural stimulation system described herein. In an embodiment, one or more associated computing devices of the system operate as specific use computers for purposes of the claimed system, and not general use computers. In an embodiment, one or more of the associated computing devices of the system are hardwired with a specific ROM to instruct the one or more computing devices.

In a general sense, the various aspects described herein which can be implemented, individually and/or collectively, by a wide range of hardware, software, firmware, and/or any combination thereof can be viewed as being composed of various types of "electrical circuitry."

At least a portion of the devices and/or processes described herein can be integrated into a data processing system. A data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

In various embodiments, methods as described herein may be performed according to instructions implementable in hardware, software, and/or firmware. Such instructions may be stored in non-transitory machine-readable data storage media, for example. The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit).

This detailed description sets forth various embodiments of devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of computer-readable medium used to actually carry out the distribution. Examples of a computer-readable medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for enhancing learning of an activity, comprising:
    a housing configured to fit in or on at least a portion of an ear of a subject;
    a neural stimulator located in or on the housing and configured to deliver a transcutaneous neural stimulus to a peripheral neural structure located at least in part in or on the ear of the subject;
    a prompting system configured to deliver at least one prompt for prompting the subject to repeatedly perform a specific activity to be learned, wherein the prompting system is located at least in part in the housing, is located at least in part on the housing, is configured as a wearable item, is configured for attachment to an instrument, is configured for attachment to an implement, is configured for attachment to an article of equipment, is configured for attachment to an article of clothing, is configured for mounting in an instrument, is configured for mounting on an instrument, is configured for mounting in an implement, is configured for mounting on an implement, is configured for mounting in an article of equipment, is configured for mounting on an article of equipment, is configured for mounting in an article of clothing, or is configured for a mounting on an article of clothing; and
    electrical control circuitry including
        stimulator control circuitry adapted to generate at least one stimulus control signal for controlling delivery of the transcutaneous neural stimulus to the peripheral neural structure with the neural stimulator;
        prompter control circuitry adapted to generate at least one prompt control signal for controlling delivery of the prompt by the prompting system; and
        timing control circuitry is configured to control a number of repetitions of the specific activity that the subject is prompted to perform by the at least one prompt and timing of delivery of the transcutaneous neural stimulus with respect to the at least one prompt.

2. The system of claim 1, including a sensing system for detecting performance of the activity by the subject.

3. The system of claim 2, wherein the sensing system includes at least one of an EEG sensor, and EMG sensor, an oxygenation sensor, a motion sensor, a pressure sensor, a force sensor, an accelerometer, an inclinometer, an implantable sensor, a wearable sensor, a sensor carried by the subject, a sensor in or on an instrument, implement, or article of equipment carried by the subject, a remote camera, and a microphone.

4. The system of claim 2, wherein the sensing system is adapted to detect performance of a mental activity, a physical activity, or two or more related physical or mental activities by the subject.

5. The system of claim 2, including at least one of a performance assessment module configured to evaluate performance of the activity by the subject or a performance feedback system configured to provide feedback to the subject regarding performance of the activity by the subject.

6. The system of claim 1, wherein the prompting system includes two or more of a display, a light, a speaker, a vibrator, a force-applying element, a mechanical stimulator, an electrical stimulator, an electromagnetic stimulator, a thermal stimulator or an olfactory stimulus source.

7. The system of claim 1, wherein the housing and the neural stimulator are configured to a deliver a transcutaneous neural stimulus to a cranial nerve of the subject.

8. The system of claim 1, further comprising a secondary stimulus source.

9. The system of claim 1, wherein the prompting system includes at least one of a visible signal source, a speaker, a display, personal computing device, an electrical stimulator, an electromagnetic stimulator, a thermal stimulator, a mechanical stimulator, a vibrator, a force-applying element, or an olfactory stimulus source.

10. The system of claim 1, wherein the housing is configured to fit at least in part on a pinna of the ear of the subject, into an ear canal of the ear of the subject, or into a concha of the ear of the subject.

11. The system of claim 1, further comprising at least one of a secondary stimulus source; communication circuitry for providing communication between the electrical control circuitry and a computing or communication network; at least one user interface device for at least one of providing an output to the subject and receiving an input from the subject; a scheduling module for creating a practice session schedule and generating reminders to remind the subject of one or more practice sessions from the practice session schedule stored; a tracking module configured to track practice sessions during which the subject practices the activity and to store tracked practice session data in a data storage location; reporting circuitry for reporting information regarding one or more tracked practice sessions, practice session trends, or practice session metrics to one or more of the subject, a parent, an instructor, a coach, a medical care provider, a peer, or a computing system; or a reward module for transferring a reward to the subject account based upon one or more tracked practice session.

12. A method of enhancing learning, comprising:
delivering, with a neural stimulator housed in a housing fitted in or on at least a portion of an ear of a subject, a transcutaneous neural stimulus to a peripheral neural structure located at least in part in or on the ear of a subject, wherein the neural stimulator is controlled by electrical control circuitry operably coupled to the neural stimulator;
delivering, with a prompting system under control of the electrical control circuitry, at least one prompt to the subject for prompting the subject to repeatedly perform a specific activity to be learned, wherein the electrical control circuitry is operably coupled to the prompting system, and wherein the prompting system is located at least in part in the housing, is located at least in part on the housing, is configured as a wearable item, is configured for attachment to an instrument, is configured for attachment to an implement, is configured for attachment to an article of equipment, is configured for attachment to an article of clothing, is configured for mounting in an instrument, is configured for mounting on an instrument, is configured for mounting in an implement, is configured for mounting on an implement, is configured for mounting in an article of equipment, is configured for mounting on an article of equipment, is configured for mounting in an article of clothing, or is configured for a mounting on an article of clothing;
controlling, with the electrical control circuitry
a timing of delivery of the transcutaneous neural stimulus with respect to the at least one prompt; and
a number of repetitions of the specific activity that the subject is prompted to perform by the at least one prompt.

13. The method of claim 12, including detecting performance of the activity by the subject with a sensing system.

14. The method of claim 13, including providing feedback to the subject with a feedback system regarding performance of the activity by the subject.

15. The method of claim 13, wherein detecting performance of the activity includes at least one of detecting performance of a mental activity by the subject; detecting performance of a physical activity by the subject; detecting performance of two or more related physical or mental activities by the subject; detecting a signal with an EEG sensor; detecting a signal with an EMG sensor; detecting a signal with an oxygenation sensor; detecting a signal with a motion sensor; detecting a signal with a pressure sensor; detecting a signal with a force sensor; detecting a signal with an accelerometer; detecting a signal with an inclinometer; detecting a signal with an implantable sensor; detecting a signal with a wearable sensor; detecting a signal with a sensor carried by the subject; or detecting a signal with a sensor in or on an instrument, implement, or article of equipment carried by the subject; detecting a signal with a remote camera, or detecting a signal with a microphone.

16. The method of claim 12, including
tracking, with a tracking module, practice session data relating to at least one practice session during which the subject practices the activity; and
storing the tracked practice session data in a data storage location.

17. The method of claim 16, including at least one of generating practice session trends or metrics based on one or more tracked practice sessions; reporting, with reporting circuitry, information regarding one or more tracked practice sessions, practice session trends, or practice session metrics to one or more of the subject, a parent, an instructor, a coach, a medical care provider, a peer, or a computing system; providing reports based on the tracked practice session data to a scoring module; assigning, with the scoring module, a score or ranking to the subject based on the performance of the subject during the one or more tracked practice sessions; assigning, with the scoring module, a score or ranking to the subject based on the subject's performance relative to the performance of one or more other individuals; or transferring, with a reward module, a reward to the subject account based upon the tracked practice session data.

18. The method of claim 12, including delivering a secondary stimulus to the subject with a secondary stimulus source.

19. The method of claim 12, including controlling the timing of delivery of the transcutaneous neural stimulus with respect to the at least one prompt to deliver the transcutaneous neural stimulus prior to the at least one prompt, deliver the transcutaneous neural stimulus subsequent to the at least one prompt, or deliver the transcutaneous neural stimulus to overlap at least partially in time with delivery of the at least one prompt.

20. The method of claim 12, wherein controlling the number of repetitions of the specific activity that the subject is prompted to perform includes controlling delivery of one prompt for each of the number of repetitions; controlling delivery of a first prompt that informs the subject of the number of repetitions and a second prompt that is repeated once for each of the number of repetitions; controlling delivery of a first prompt that informs the subject of the specific activity that is to be performed and a second prompt that is repeated once for each of the number of repetitions; or controlling delivery of the at least one prompt at a fixed rate for a fixed period of time.

21. The method of claim 12, wherein delivering the at least one prompt includes at least one of delivering an audible prompt, delivering a visible prompt, delivering an audio-visual prompt, delivering a tactile prompt, delivering a haptic prompt, delivering an electrical stimulus, delivering the at least one prompt via a speaker, or delivering the at least one prompt via a display.

22. The method of claim 12, wherein delivering the at least one prompt includes at least one of delivering the at least one prompt via a personal computing device; delivering the at least one prompt via a wearable item;
  delivering the at least one prompt via a prompting system attached to or mounted in or on an instrument, implement, article of equipment, or article of clothing; or
  delivering the at least one prompt via two or more of a display, a light, a speaker, a vibrator, an electrical stimulator, and an olfactory stimulus source.

23. The method of claim 12, wherein the transcutaneous neural stimulus is a learning-enhancing stimulus or a memory-blocking stimulus.

24. The method of claim 12, including delivering the transcutaneous neural stimulus to at least one of a cranial nerve of the subject, a vagal nerve of the subject, a trigeminal nerve of the subject, a glossopharyngeal nerve of the subject, a peripheral neural structure innervating a pinna of the ear of the subject, a peripheral neural structure innervating an ear canal of the ear of the subject, or a peripheral neural structure innervating a concha of the ear of the subject.

25. The method of claim 12, including at least one of receiving, with an interface device, a control input for setting stimulation parameters; sending a communication from the electrical control circuitry to a computing or communication network via communication circuitry operably coupled to the electrical control circuitry; receiving a communication at the electrical control circuitry from the computing or communication network via communication circuitry operably coupled to the electrical control circuitry; providing an output to the subject via a user interface device; and receiving an input from the subject via a user interface device.

26. The method of claim 12, including
  creating a practice session schedule;
  storing the practice session schedule in a data storage location operatively coupled to the electrical control circuitry; and
  generating reminders for delivery to the subject via at least one user interface device operably coupled to the control circuitry to remind the subject of one or more practice sessions from the practice session schedule stored in the data storage location.

27. A computer program product, comprising:
  at least one non-transitory computer-readable medium bearing
  one or more instructions for generating, under control of electrical control circuitry, a least one stimulus control signal for controlling delivery of a transcutaneous neural stimulus to a peripheral neural structure located at least in part in or on an ear of a subject via a neural stimulator fitted in or on at least a portion of the ear of a subject;
  one or more instructions for delivering, via a prompting system under control of the electrical control circuitry, at least one prompt for prompting the subject to repeatedly perform a specific activity to be learned, wherein the prompting system is located at least in part in the housing, is located at least in part on the housing, is configured as a wearable item, is configured for attachment to an instrument, is configured for attachment to an implement, is configured for attachment to an article of equipment, is configured for attachment to an article of clothing, is configured for mounting in an instrument, is configured for mounting on an instrument, is configured for mounting in an implement, is configured for mounting on an implement, is configured for mounting in an article of equipment, is configured for mounting on an article of equipment, is configured for mounting in an article of clothing, or is configured for a mounting on an article of clothing;
  one or more instructions for controlling a timing of delivery of the transcutaneous neural stimulus with respect to the at least one prompt; and
  one or more instructions for controlling a number of repetitions of the specific activity that the subject is prompted to perform by the at least one prompt.

28. The computer program product of claim 27, wherein the at least one non-transitory computer-readable medium bears
  one or more instructions for tracking, with a tracking module, practice session data relating to at least one practice session during which the subject practices the activity; and
  one or more instructions for storing the tracked practice session data in a data storage location.

29. The computer program product claim 28, wherein the at least one non-transitory computer-readable medium bears one or more instructions for reporting, with reporting circuitry, information regarding one or more tracked practice sessions, practice session trends, or practice session metrics to one or more of the subject, a parent, an instructor, a coach, a medical care provider, a peer, or a computing system.

30. The computer program product of claim 29, wherein the one or more instructions for reporting with the reporting circuitry include one or more instructions for providing reports based on the tracked practice session data to a scoring module; wherein the at least one non-transitory computer-readable medium bears one or more instructions for assigning, with the scoring module, a score or ranking to the subject based on the performance of the subject during the one or more tracked practice sessions; or wherein the at least one non-transitory computer-readable medium bears one or more instructions for assigning, with the scoring module, a score or ranking to the subject based on the subject's performance relative to the performance of one or more other individuals.

31. The computer program product of claim 28, wherein the one or more instructions for storing the tracked practice session data in the data storage location include one or more instructions for storing at least one of a time, a date, or a duration of at least one practice session; wherein the at least one non-transitory computer-readable medium bears one or more instructions for generating practice session trends or metrics based on one or more tracked practice sessions; or wherein the at least one non-transitory computer-readable medium bears one or more instructions for transferring, with a reward module, a reward to the subject account based upon the tracked practice session data.

32. The computer program product of claim 27, wherein the at least one non-transitory computer-readable medium bears
- one or more instructions for creating a practice session schedule;
- one or more instructions storing the practice session schedule in a data storage location operatively coupled to the electrical control circuitry; and
- one or more instructions for generating reminders for delivery to the subject via at least one user interface device operably coupled to the control circuitry to remind the subject of one or more practice sessions from the practice session schedule stored in the data storage location.

33. The computer program product of claim 27, wherein the at least one non-transitory computer-readable medium bears at least one of one or more instructions for receiving, with an interface device, a control input for setting stimulation parameters; one or more instructions for sending a communication from the electrical control circuitry to a computing or communication network, via communication circuitry operably coupled to the electrical control circuitry; one or more instructions for receiving a communication at the electrical control circuitry from a computing or communication network, via communication circuitry operably coupled to the electrical control circuitry; or one or more instructions for providing an output to the subject or receiving an input from the subject via a user interface device.

* * * * *